(12) United States Patent
Natale et al.

(10) Patent No.: US 10,934,277 B2
(45) Date of Patent: Mar. 2, 2021

(54) ENANTIOMERICALLY PURIFIED GPER AGONIST FOR USE IN TREATING DISEASE STATES AND CONDITIONS

(71) Applicant: Linnaeus Therapeutics, Inc., Haddonfield, NJ (US)

(72) Inventors: Christopher Natale, Philadelphia, PA (US); Patrick T. Mooney, Haddonfield, NJ (US); Tina Garyantes, Warren, NJ (US); Wayne Luke, West Lafayette, IN (US)

(73) Assignee: LINNAEUS THERAPEUTICS, INC., Haddonfield, NJ (US)

( * ) Notice: Subject to any disclaimer, the term of this patent is extended or adjusted under 35 U.S.C. 154(b) by 0 days.

(21) Appl. No.: 16/682,821

(22) Filed: Nov. 13, 2019

(65) Prior Publication Data

US 2020/0140417 A1    May 7, 2020

Related U.S. Application Data

(63) Continuation of application No. 16/518,516, filed on Jul. 22, 2019.

(60) Provisional application No. 62/701,726, filed on Jul. 21, 2018.

(51) Int. Cl.
*C07D 405/04* (2006.01)

(52) U.S. Cl.
CPC ........ *C07D 405/04* (2013.01); *C07B 2200/07* (2013.01); *C07B 2200/13* (2013.01)

(58) Field of Classification Search
CPC .................................. C07D 405/04
USPC ......................................... 546/79
See application file for complete search history.

(56) References Cited

U.S. PATENT DOCUMENTS

| 7,875,721 | B2 | 1/2011 | Prossnitz et al. |
| 8,487,100 | B2 * | 7/2013 | Prossnitz ............. C07D 221/16 |
| | | | 546/79 |
| 10,251,870 | B2 * | 4/2019 | Prossnitz ............. A61K 31/435 |
| 2010/0204204 | A1 * | 8/2010 | Zaworotko ............ A61K 31/20 |
| | | | 514/212.03 |
| 2012/0149687 | A1 * | 6/2012 | Lee ...................... A61K 31/541 |
| | | | 514/211.15 |
| 2018/0055826 | A1 | 3/2018 | Prossnitz et al. |
| 2018/0273482 | A1 | 9/2018 | Ridky et al. |
| 2018/0354935 | A1 | 12/2018 | Ridky et al. |
| 2019/0160047 | A1 | 5/2019 | Prossnitz et al. |

FOREIGN PATENT DOCUMENTS

WO    2017218191 A1    12/2017

OTHER PUBLICATIONS

Abu, Adv. Drug Del. Rev. (2007), 59, pp. 603-616.*

(Continued)

*Primary Examiner* — Taofiq A Solola
(74) *Attorney, Agent, or Firm* — McDonnell Boehnen Hulbert & Berghoff LLP

(57) ABSTRACT

The present disclosure provides 1) an enantiomerically purified compound SRR G-1, or a derivative thereof, including specific crystal forms, salts and co-crystals that modulates G protein-coupled estrogen receptor activity, 2) pharmaceutical and cosmetic compositions comprising an enantiomerically purified SRR G-1, or a derivative thereof, and 3) methods of treating or preventing disease states and conditions and cosmetic conditions mediated through these receptors and related methods thereof in humans and animals.

11 Claims, 38 Drawing Sheets

(56) References Cited

OTHER PUBLICATIONS

Pharmaceutical Technology, (2006) vol. 30(10), pp. 1-17, [PharmTech].*
Berge et al. "Pharmaceutical Salts" Jan. 1977, J. Pharm. Sci. 66(1):1-19.
Burai et al. "Highly Efficient Synthesis and Characterization of the GPR30-Selective Agonist G-1 and Related Tetrahydroquinoline Analogs" 2010, Org. Biomol. Chem. 8:2252-2259.
International Search Report and Written Opinion for PCT/US2019/042827 dated Oct. 4, 2019.
Prossnitz et al. "The G Protein-Coupled Estrogen Receptor GPER in Health and Disease" Dec. 1, 2012, Nat. Rev. Endocrinol. 7(12):715-726.
Bernstein, J., "Exploring the crystal form landscape," Polymorphism in Molecular Crystals, Second Edition, Oxford University Press, 2020, Chapter 3.
Betnstein, J., "Introduction and historical background," Polymorphism in Molecular Crystals, Second Edition, Oxford University Press, 2020, Chapter 1.
Bernstein. J., "Polymorphism and patents," Polymorphism in Molecular Crystals, Second Edition, Oxford University Press, 2020, Chapter 10.
Bowker, M. J., "A Procedure for Salt Selection and Optimization," Handbook of Pharmaceutical Salts, P. Heinrich Stahl, Camille G. Wermuth, Eds., Wiley-VCH, 2008, Chapter 7, p. 162-189.
Byrn et al., "Solubility and Dissolution Testing," Solid-State Chemistry of Drugs, Second Edition, SSCI, Inc., West Lafayette, IN, USA, 1999, Chapter 6.
Byrn, et al., "Miscellaneous Topics," Solid-State Chemistry of Drugs, Second Edition, SSCI, Inc., West Lafayette, IN, USA, 1999, Chapter 22.
Kumar, L., et al. "Salt Selection in Drug Development," Pharmaceutical Technology, 2008; 3(32).
Stahl, P. H. "Appendix," Handbook of Pharmaceutical Salts, P. Heinrich Stahl, Camille G. Wermuth, Eds., Wiley-VCH, 2008, p. 329-350.
Stahly, G. P., "Diversity in Single- and Multiple-Component Crystals. The Search for and Prevalence of Polymorphs and Cocrystals," Crystal Growth & Design, 2007, vol. 7, No. 6, 1007-1026.

* cited by examiner

Atomic displacement ellipsoid diagram of SRR G-1 dichloromethane solvate.

Non-hydrogen atoms are represented by 50% probability anisotropic thermal ellipsoids.

Packing diagram viewed along the crystallographic *a* axis

Packing diagram viewed along the crystallographic *b* axis

Packing diagram viewed along the crystallographic *c* axis.

One-dimensional hydrogen bond network

Labeled chiral centers

Calculated X-ray powder pattern of SRR G-1 dichloromethane solvate

Atomic displacement ellipsoid diagram of SRR G-1 Form A

SRR G-1 Form A is anhydrous. Non-hydrogen atoms are represented by 50% probability anisotropic thermal ellipsoids. This structure contains three chiral centers located at C114 (C214), C113 (C213), and C19 (C29) which bond in the *R, S,* and *R* configuration, respectively.

Calculated and experimental XRPD patterns for SRR G-1 Form A

From top to bottom:

Experimental pattern of SRR G-1 Form A

Calculated powder pattern from anhydrous crystal SRR G-1 Form A

XRPD patterns for SRR G-1 Forms A, B, and C

From top to bottom:

SRR G-1 Form A, stable anhydrous form

SRR G-1 Form B, mono DCM solvate

SRR G-1 Form C, metastable desolvate

Atomic displacement ellipsoid diagram of SRR G-1 Form B

SRR G-1 Form B is a monodichloromethane solvate. Non-hydrogen atoms are represented by 50% probability anisotropic thermal ellipsoids. The structure contains three chiral centers located at C8, C9, and C13 which bond in the *R, S,* and *R* configuration, respectively.

Calculated and experimental XRPD patterns for SRR G-1 Form B

From top to bottom:

Experimental pattern of SRR G-1 Form B

Calculated pattern from monoDCM solvate crystal

XRPD indexing results for SRR G-1 Form C

XRPD overlay of residual solids after pH solubility test (II/II)

Solubility of SRR G-1 freebase in bio-relevant media

XRPD overlay of SRR G-1 after solubility test in SGF

XRPD overlay of SRR G-1 after solubility test in FaSSIF

XRPD patterns of SRR G-1 salts.

Top to bottom:

File 938621, LNS8801 Besylate Form A

File 940610, LNS8801 Camsylate Form A

File 939566, LNS8801 Napsylate Form A

File 936114, LNS8801 Batch 3, freebase Form A

Atomic displacement ellipsoid diagram of SRR G-1 Besylate Form A
Non-hydrogen atoms are represented by 50% probability anisotropic thermal ellipsoids. Disorder on the –SO₃ moiety not shown.

Calculated and experimental XRPD patterns for SRR G-1 Besylate Form A

Top to bottom:

Calculated powder pattern from single crystal of SRR G-1 Besylate Form A

Experimental pattern of SRR G-1 Besylate Form A

Indexing results for SRR G-1 Camsylate Form A

XRPD pattern for SRR G-1 Camsylate Form A shown from 5 to 19° (2θ).

Vertical lines represent the allowed peak positions for SRR G-1 Camsylate Form A, as determined from indexing. Extra, unidentified peaks are marked with symbol *.

Indexing results for SRR G-1 Napsylate Form A

Plasma Concentration of SRR G-1 in the Rat Dosed with SRR G-1 Free Base

Plasma Concentration of SRR G-1 in the Rat Dosed with SRR G-1 Besylate

Plasma Concentration of SRR G-1 in the Rat Dosed with SRR G-1 Napsylate

Comparison of Plasma Concentrations of SRR G-1 in the Rat Dosed with SRR G-1 Free Base, SRR G-1 Besylate, and SRR G-1 Napsylate

ENANTIOMERICALLY PURIFIED GPER AGONIST FOR USE IN TREATING DISEASE STATES AND CONDITIONS

CROSS-REFERENCE TO RELATED APPLICATIONS

This application is a continuation application of U.S. application Ser. No. 16/518,516 filed Jul. 22, 2019 which claims priority from U.S. Provisional Application No. 62/701,726 filed Jul. 21, 2018, each of which are hereby incorporated by reference in its entirety.

GOVERNMENT INTERESTS

This invention was made with United States Government support under Grant No. 2R44CA228695-02 awarded by the National Cancer Institute of the National Institutes of Health. The United States Government has certain rights in the invention.

SUMMARY

Embodiments of the present invention relate to an enantiomerically purified agonist of the G-protein coupled estrogen receptor (GPER), pharmaceutical compositions comprising an enantiomerically purified SRR G-1, or a derivative thereof, and methods of treating disease states and conditions in subjects in need thereof, and methods of treating disease states and conditions mediated through GPER receptors.

Estrogens mediate multiple complex physiological responses throughout the body. The responses are in turn mediated through the binding of estrogen to receptors. The classical receptors bind steroids, such as estrogen, and are soluble cytoplasmic/nuclear proteins that function as transcription factors. These receptors are known as estrogen receptor alpha and beta (two closely related proteins) that mediate transcriptional activity. GPER is a 7-transmembrane G protein-coupled receptor that also binds to estrogen with high affinity ($K_d$~6 nM) and mediates rapid cellular responses including cyclic adenosine monophosphate signaling, calcium mobilization and phosphatidylinositol 3,4,5 trisphosphate production.

Diseases whose development, progression, and or response to therapy, may be influenced by endogenous, and/or pharmacologic activation of GPER signaling include cancer (including the prevention of cancer, prevention of the reoccurrence of cancer, and the inhibition of the progression of cancer; and particularly melanoma, pancreatic, lymphomas, uveal melanoma, non-small cell lung cancer, breast, reproductive and other hormone-dependent cancers, leukemia, colon cancer, prostate, bladder cancer), reproductive (genito-urological) including endometritis, prostatitis, polycystic ovarian syndrome, bladder control, hormone-related disorders, hearing disorders, cardiovascular conditions including hot flashes and profuse sweating, hypertension, stroke, obesity, diabetes, osteoporosis, hematologic diseases, vascular diseases or conditions such as venous thrombosis, atherosclerosis, among numerous others and disorders of the central and peripheral nervous system, including depression, insomnia, anxiety, neuropathy, multiple sclerosis, neurodegenerative disorders such as Parkinson's disease and Alzheimer's disease, as well as inflammatory bowel disease, Crohn's disease, coeliac (celiac) disease and related disorders of the intestine.

DETAILED DESCRIPTION

Definitions

Figure 1:
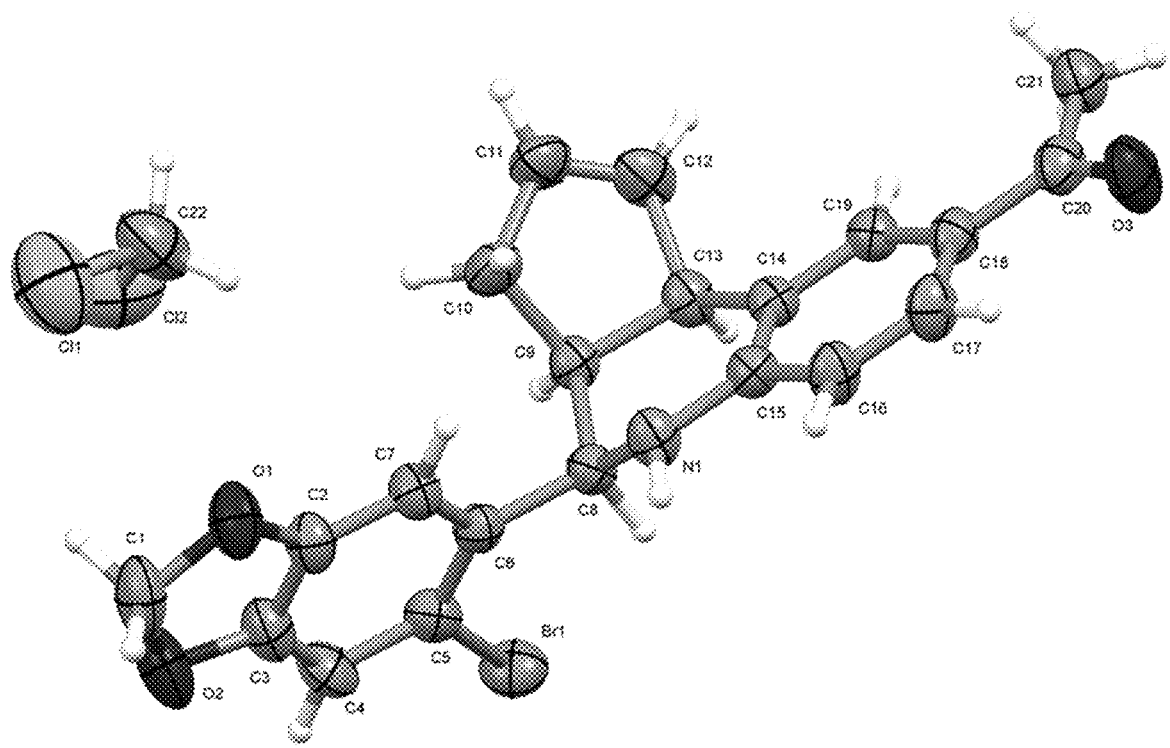
FIG. 1 shows an atomic displacement ellipsoid drawing of SSR G-1 dichloromethane solvate.

As used herein, the terms below have the meanings indicated.

Before the present compounds, compositions and methods are described, it is to be understood that this invention is not limited to the particular processes, formulations, compound, compositions, or methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

It must also be noted that as used herein and in the appended claims, the singular forms "a," "an," and "the" include plural reference unless the context clearly dictates otherwise.

As used herein, the term "about" means plus or minus 20% of the numerical value of the number with which it is being used. Therefore, about 50% means in the range of 40%-60%.

In embodiments or claims where the term "comprising" is used as the transition phrase, such embodiments can also be envisioned with replacement of the term "comprising" with the terms "consisting of" or "consisting essentially of."

As used herein, the term "consists of" or "consisting of" means that the compound, composition, formulation or the method includes only the elements, steps, or ingredients specifically recited in the particular claimed embodiment or claim.

As used herein, the term "consisting essentially of" or "consists essentially of" means that the compound, composition, formulation or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the formulation or method that treats the specified condition (e.g., cancer and/or obesity) is the specifically recited therapeutic(s) in the particular embodiment or claim.

As used herein, the term "a derivative thereof" refers to any molecular form of the compound it references, including, but not limited to, a salt thereof, a pharmaceutically acceptable salt thereof, an ester thereof, a free base thereof, a solvate thereof, a hydrate thereof, an N-oxide thereof, a clathrate thereof, a prodrug thereof, an isotope thereof (e.g., tritium, deuterium), a co-crystal thereof, and any combination of the foregoing.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein may exist in unsolvated as well as solvated forms with pharmaceutically acceptable solvents such as water, ethanol, and the like. In general, the solvated forms are considered equivalent to the unsolvated forms.

As used herein, the term "chiral purity" and "enantiomeric excess" (ee) are interchangeable and may refer to the measurement of the absolute difference between the mole fraction of each enantiomer and is most often expressed as a percentage. % Enantiomeric excess may be determined by the formula:

$$\% \ ee = |A-B| \times 100$$

Where A and B are the respective mole fractions of the enantiomers in a mixture such that A+B=1. A racemic mixture has an enantiomeric excess of 0%, while a single completely pure enantiomer has an enantiomeric excess of 100%. As an example, a sample with 70% of R isomer and 30% of S will have an enantiomeric excess of 40%. This can also be thought of as a mixture of 40% pure R with 60% of a racemic mixture (which contributes 30% R and 30% S to the overall composition).

The term "substantially free" as used herein, alone or in combination, refers to the absence of isomers within the limits of quantitation of analytical methods such as nuclear magnetic resonance (NMR), gas chromatography/mass spectroscopy (GC/MS), high performance liquid chromatography (HPLC), circular dichroism (CD), or other methods of chemical analysis.

"Pharmaceutically acceptable salt" is meant to indicate those salts or co-crystals which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol. 6, 1-19, describes representative pharmaceutically acceptable salts in detail. A pharmaceutical acceptable "salt" is any acid addition salt or co-crystal, preferably a pharmaceutically acceptable acid addition salt or co-crystal, including, but not limited to, halogenic acid salts such as hydrobromic, hydrochloric, hydrofloric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesufonic), acetic, malic, fumaric, succinic, citric, benzonic gluconic, lactic, mandelic, mucic, pamoic, pantothenic, oxalic and maleic acid salts; and an amino acid salt such as aspartic or glutamic acid salt, benzenesulfonic, (+)-(1S)-camphor-10-sulfonic, ethane-1,2-disulfonic, hydrochloric, methanesulfonic, naphthalene-2-sulfonic, naphthalene-1,5-disulfonic, sulfuric, and p-toluenesulfonic acid. The pharmaceutically acceptable salt may be a mono- or di-acid addition salt, such as a di-hydrohalogic, di-sulfuric, di-phosphoric or di-organic acid salt. The pharmaceutically acceptable salt is used as a chiral or achiral reagent which is not required to be selected on the basis of any expected or known preference for the interaction with or precipitation of a specific optical isomer of the products of this disclosure.

The term "therapeutically acceptable salt," as used herein, represents salts or co-crystals or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid or by substituting one salt for an therapeutic acceptable salt. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Hence, the present invention contemplates sodium, potassium, magnesium, and calcium salts of the compounds disclosed herein, and the like.

As used herein, the term "patient" and "subject" are interchangeable and may be taken to mean any living organism, which may be treated with compounds of the present invention. As such, the terms "patient" and "subject" may include, but is not limited to, any non-human mammal, primate or human. In some embodiments, the "patient" or "subject" is an adult, child, infant, or fetus. In some embodiments, the "patient" or "subject" is a human. In some embodiments, the "patient" or "subject" is a mammal, such as mice, rats, other rodents, rabbits, dogs, cats, swine, cattle, sheep, horses, primates, or humans.

The terms "therapeutically effective amount" or "therapeutic dose" is used herein are interchangeable and may refer to the amount of an active agent or pharmaceutical compound or composition that elicits a clinical, biological or medicinal response in a tissue, system, animal, individual or human that is being sought by a researcher, veterinarian, medical doctor or other clinical professional. A clinical, biological or medical response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experienced or exhibited by the individual.

The terms "administer," "administering" or "administration" as used herein refer to either directly administering a compound or pharmaceutically acceptable salt of the compound or a composition to a subject.

The term "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to alleviating the symptoms associated with the specific disorder, disease or condition. In some embodiments, the term refers to alleviating the symptoms associated with the specific disorder, disease or condition. In some embodiments, the term refers to restoring function which was impaired or lost due to a specific disorder, disorder or condition.

The term "preventing" may be taken to mean to prevent a specific disorder, disease or condition and/or prevent the reoccurrence of a specific disorder, disease or condition.

The term "unit dosage form" refers to physically discrete units suitable as a unitary dosage for human subjects and other animals, each unit containing a predetermined quantity of active material calculated to produce the desired therapeutic effect, in association with a suitable pharmaceutical excipient.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a medical condition or disorder described in the present disclosure. Such administration encompasses co-administration of these therapeutic agents in a substantially simultaneous manner, such as in a single capsule, or dosage presentation, having a fixed ratio of active ingredients or in multiple, separate capsules for each active ingredient. In addition, such administration also encompasses use of each type of therapeutic agent in a sequential manner in the same patient, with delivery of the individual therapeutics separated by 1-24 hours, 1-7 days, or 1 or more weeks. In either case, the treatment regimen will provide beneficial effects of the drug combination in treating the conditions or disorders described herein.

Compounds

Many organic compounds exist in optically active forms, i.e. they have the ability to rotate the plane of plane polarized light. In describing an optically active compound, the prefixes R and S are used to denote the absolute configuration of the molecule about its chiral center(s). For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 8 of the 10 most prescribed drugs exhibit chirality. A case in point is provided by the S-enantiomer of the β-adrenergic blocking agent, propranolol, which is known to be 100 times more potent than the R-enantiomer.

Embodiments of the present invention encompass compounds comprising enantiomerically purified G-1 and methods of use in the treatment of diseases. G-1 is a racemic mixture of the enantiomers 1-((3 aS,4R,9bR)-4-(6-bromobenzo[d][1,3]dioxol-5-yl)-3a,4,5,9b-tetrahydro-3H-cyclopenta[c]quinolin-8-yl)ethan-1-one (henceforth referred to as "SRR G-1" or "LNS 8801") and 1-((3aR,4S,9bS)-4-(6-bromobenzo[d][1,3]dioxol-5-yl)-3a,4,5,9b-tetrahydro-3H-cyclopenta[c]quinolin-8-yl)ethan-1-one (henceforth referred to as "RSS G-1" or "LNS8812").

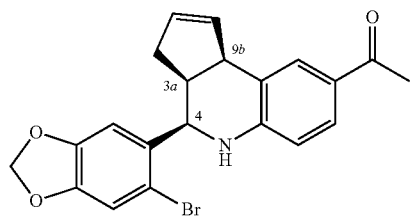

1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one

SRR G-1

G-1

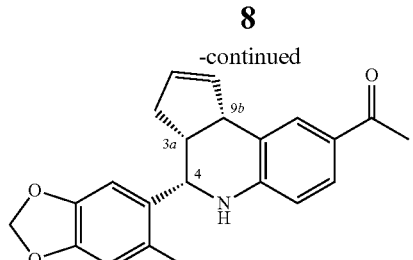

1-((3aR,4S,9bS)-4-(6-bromobenzo[d][1,3]dioxol-5-yl)-3a,4,5,9b-tetrahydro-3H-cyclopenta[c]quinolin-8-yl)ethan-1-one

RSS G-1

Enantiomerically purified G-1 has been purified in favor of its 1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one enantiomer over the corresponding 1-((3aR,4S,9bS)-4-(6-bromobenzo[d][1,3]dioxol-5-yl)-3a,4,5,9b-tetrahydro-3H-cyclopenta[c]quinolin-8-yl)ethan-1-one enantiomer. Unless specifically described, SRR G1, or a derivative thereof includes, any physical form, including an amorphous form or any crystalline solid forms such as A, B, C or combinations thereof.

In certain embodiments, the compound of 1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one (also referred to as "SRR G-1"), or a derivative thereof, has a chiral purity of about 90% or greater. In certain embodiments SRR G-1, or a derivative thereof, has a chiral purity of about 91% or greater. In certain embodiments SRR G-1, or a derivative thereof, has a chiral purity of about 92% or greater. In certain embodiments SRR G-1, or a derivative thereof, has a chiral purity of about 93% or greater. In certain embodiments SRR G-1, or a derivative thereof, has a chiral purity of about 94% or greater. In certain embodiments SRR G-1, or a derivative thereof, has a chiral purity of about 95% or greater. In certain embodiments SRR G-1, or a derivative thereof, has a chiral purity of about 96% or greater. In certain embodiments SRR G-1, or a derivative thereof, has a chiral purity of about 97% or greater. In certain embodiments SRR G-1, or a derivative thereof, has a chiral purity of about 97.5% or greater. In certain embodiments SRR G-1, or a derivative thereof, has a chiral purity of about 98% or greater. In certain embodiments SRR G-1, or a derivative thereof, has a chiral purity of about 99% or greater. In certain embodiments SRR G-1, or a derivative thereof, has a chiral purity of about 99.1% or greater. In certain embodiments SRR G-1, or a derivative thereof, has a chiral purity of about 99.2% or greater. In certain embodiments SRR G-1, or a derivative thereof, has a chiral purity of about 99.3% or greater. In certain embodiments SRR G-1, or a derivative thereof, has a chiral purity of about 99.4% or greater. In certain embodiments SRR G-1, or a derivative thereof, has a chiral purity of about 99.5% or greater. In certain embodiments SRR G-1, or a derivative thereof, has a chiral purity of about 99.6% or greater. In certain embodiments SRR G-1, or a derivative thereof, has a chiral purity of about 99.7% or greater. In certain embodiments SRR G-1, or a derivative thereof, has a chiral purity of about 99.75% or greater. In certain embodiments SRR G-1, or a derivative thereof, has a chiral purity of about 99.8% or greater. In certain embodiments SRR G-1, or a derivative thereof, has a chiral purity of about 99.9% or greater. In certain embodiments SRR G-1, or a derivative thereof, has a chiral purity of about 99.91% or greater. In certain embodiments SRR G-1, or a derivative thereof, has a chiral purity of about 99.92% or greater. In certain embodiments SRR G-1, or a derivative thereof, has a chiral purity of about 99.93% or greater. In certain embodiments SRR G-1, or a derivative thereof, has a chiral purity of about 99.94% or greater. In certain embodiments SRR G-1, or a derivative thereof, has a chiral purity of about 99.95% or greater. In certain embodiments SRR G-1, or a derivative thereof, has a chiral purity of about 99.96% or greater. In certain embodiments SRR G-1, or a derivative thereof, has a chiral purity of about 99.97% or greater. In certain embodiments SRR G-1, or a derivative thereof, has a chiral purity of about 99.98% or greater. In certain embodiments SRR G-1, or a derivative thereof, has a chiral purity of about 99.99% or greater. In certain embodiments SRR G-1, or a derivative thereof, is free of its opposite enantiomer within the limits of quantification. In certain embodiments SRR G-1, or a derivative thereof, is substantially free of its opposite enantiomer.

In any of the embodiments of SRR G-1 described herein, wherein the compound is crystalline as evidenced by XRPD analysis or amorphous as evidenced by XRPD analysis or a mixture of crystalline and amorphous material.

Figure 10:
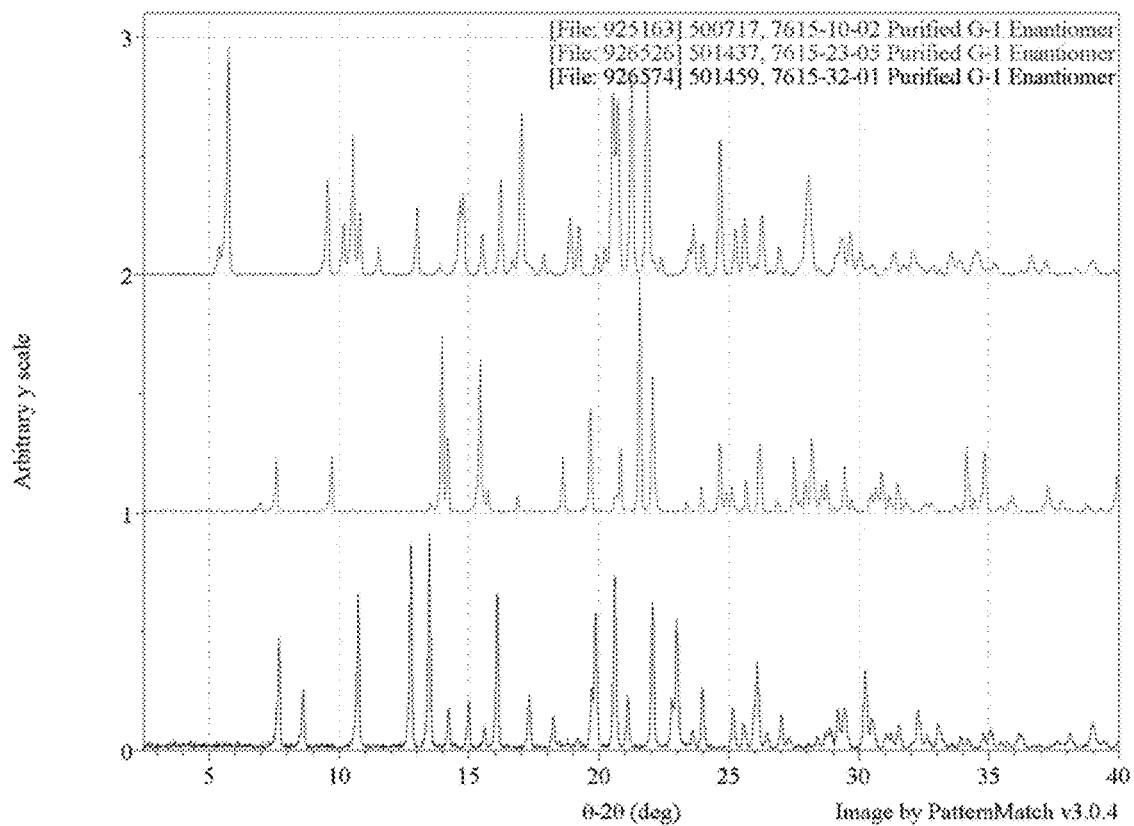
FIG. 10 shows the XRPD patterns for SRR G-1 Forms A, B, and C.

In any of the embodiments of SRR G-1 described herein, the form of 1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one, is selected from crystalline Form A that is characterized by an XRPD pattern of FIG. 10, crystalline Form B that is characterized by an XRPD pattern of FIG. 10, crystalline Form C that is characterized by an XRPD pattern of FIG. 10, amorphous, or combinations thereof.

In any of the embodiments of SRR G-1 described herein, the crystalline form of 1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one, is selected from crystalline Form A that is characterized by an XRPD pattern of FIG. 10, crystalline Form B that is characterized by an XRPD pattern of FIG. 10, crystalline Form C that is characterized by an XRPD pattern of FIG. 10, or combinations thereof.

In certain embodiments, the crystalline form of 1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one, is crystalline Form A that is characterized by an XRPD pattern of FIG. 10.

In any of the embodiments of SRR G-1 described herein, wherein the form of 1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one, is selected from crystalline Form A that is characterized by an XRPD pattern having peaks expressed in degrees 2θ (±0.20) at about 5.75, about 20.54, about 20.71, about 21.25, and about 21.86; crystalline Form B that is characterized by an XRPD pattern having peaks expressed in degrees 2θ (±0.20) at about 13.98, about 15.44, about 19.67, about 21.55, and about 22.05; crystalline Form C that is characterized by an XRPD pattern having peaks expressed in degrees 2θ (±0.20) at about 10.73, about 12.77, about 13.49, about 16.09, and about 20.60; amorphous; or combinations thereof.

In any of the embodiments of SRR G-1 described herein, wherein the crystalline form of 1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one, is selected from crystalline Form A that is characterized by an XRPD pattern having peaks expressed in degrees 2θ (±0.20) at about 5.75, about 20.54, about 20.71, about 21.25, and about 21.86; crystalline Form B that is characterized by an XRPD pattern having peaks expressed in degrees 2θ (±0.20) at about 13.98, about 15.44, about 19.67, about 21.55, and about 22.05; crystalline Form C that is characterized by an XRPD pattern having peaks expressed in degrees 2θ (±0.20) at about 10.73, about 12.77, about 13.49, about 16.09, and about 20.60; or combinations thereof.

In certain embodiments, the crystalline form of 1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one, is crystalline Form A that is characterized by an XRPD pattern having peaks expressed in degrees 2θ (±0.20) at about 5.75, about 20.54, about 20.71, about 21.25, and about 21.86. In certain embodiments, crystalline Form A that is further characterized by an XRPD pattern having peaks expressed in degrees 2θ (±0.20) at about 5.75, about, 9.56, about 10.53, about 17.03, about 20.54, about 20.71, about 21.25, about 21.86, about 24.67, and about 28.06. In certain embodiments, crystalline Form A that is further characterized by an XRPD pattern having peaks expressed in degrees 2θ (±0.20) at about 5.75, about, 9.56, about 10.53, about 10.81, about 13.02, about 14.66, about 14.79, about 16.23, about 17.03, about 20.54, about 20.71, about 21.25, about 21.86, about 24.67, and about 28.06.

In certain embodiments, the crystalline form of 1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one, is crystalline Form B that is characterized by an XRPD pattern having peaks expressed in degrees 2θ (±0.20) at about 13.98, about 15.44, about 19.67, about 21.55, and about 22.05. In certain embodiments, crystalline Form B that is further characterized by an XRPD pattern having peaks expressed in degrees 2θ (±0.20) at about 13.98, about 14.19, about 15.44, about 19.67, about 20.82, about 21.55, about 22.05, about 24.65, about 26.18, and about 28.18. In certain embodiments, crystalline Form B that is further characterized by an XRPD pattern having peaks expressed in degrees 2θ (±0.20) at about 7.60, about 9.71, about 13.98, about 14.19, about 15.44, about 18.61, about 19.67, about 20.82, about 21.55, about 22.05, about 24.65, about 26.18, and about 28.18.

In certain embodiments, the crystalline form of 1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one, is crystalline Form C that is characterized by an XRPD pattern having peaks expressed in degrees 2θ (±0.20) at about 10.73, about 12.77, about 13.49, about 16.09, and about 20.60. In certain embodiments, crystalline Form C the is further characterized by an XRPD pattern having peaks expressed in degrees 2θ (±0.20) at about 7.69, about 8.62, about 10.73, about 12.77, about 13.49, about 16.09, about 19.86, about 20.60, about 22.05, and about 22.98.

In any of the embodiments of SRR G-1 described herein, or a derivative thereof, the derivative thereof is a salt or co-crystal.

In any of the embodiments of SRR G-1 described herein, or a derivative thereof, the derivative thereof is selected from salts or co-crystals formed with benzenesulfonic acid, with (+)-(1S)-camphor-10-sulfonic acid, with ethane-1,2-disulfonic acid, with hydrochloric acid, with methanesulfonic acid, with naphthalene-2-sulfonic acid, with naphthalene-1,5-disulfonic acid, with sulfuric acid, with p-toluenesulfonic acid, or combinations thereof.

In certain embodiments, the derivative thereof is a salt or co-crystal formed with benzenesulfonic acid.

In certain embodiments, the derivative thereof is a salt or co-crystal formed with (+)-(1S)-camphor-10-sulfonic acid.

In certain embodiments, the derivative thereof is a salt or co-crystal formed with naphthalene-2-sulfonic acid.

In certain embodiments, the derivative thereof is a salt or co-crystal formed with benzenesulfonic acid and is characterized by an XRPD pattern having peaks expressed in degrees 2θ (±0.20) at about 4.26, about 6.51, about 6.71, about 16.86, about 18.92, about 19.99, about 20.29, about 20.75, about 21.46, about 22.06, about 22.12, and about 23.99.

In certain embodiments, the derivative thereof is a salt or co-crystal formed with (+)-(1S)-camphor-10-sulfonic acid and is characterized by an XRPD pattern having peaks expressed in degrees 2θ (±0.20) at about 5.97, about 11.98, about 12.69, about 13.41, about 16.23, about 17.79, about 18.03, about 18.77, and about 19.69.

In certain embodiments, the derivative thereof is a salt or co-crystal formed with naphthalene-2-sulfonic acid and is characterized by an XRPD pattern having peaks expressed in degrees 2θ (±0.20) at about 6.17, about 12.63, about 12.84, about 13.75, about 14.39, about 16.79, about 17.07, about 17.64, about 19.22, about 19.44, about 20.43, about 21.26, about 21.78, about 22.60, about 23.38, about 26.07, and about 27.63.

In any of the embodiments of SRR G-1 described herein, SRR G-1, or a derivative thereof, and at a concentration of 500 nM has about a 2.5 fold or greater increase in inhibition of cell growth in a YUMM1.7 4 day growth assay as compared to a racemic mixture of SRR G-1 and its opposite enantiomer. In certain embodiments, SRR G-1, or a derivative thereof, has about a 3 fold or greater increase in inhibition of cell growth. In certain embodiments, SRR G-1, or a derivative thereof, has about a 3.5 fold or greater increase in inhibition of cell growth. In certain embodiments, SRR G-1, or a derivative thereof, has about a 4 fold or greater increase in inhibition of cell growth. In certain embodiments, SRR G-1, or a derivative thereof, has about a 4.5 fold or greater increase in inhibition of cell growth. In certain embodiments, SRR G-1, or a derivative thereof, has about a 5 fold or greater increase in inhibition of cell growth. In certain embodiments, SRR G-1, or a derivative thereof, has about a 5.5 fold or greater increase in inhibition of cell growth. In certain embodiments, SRR G-1, or a derivative thereof, has about a 6 fold or greater increase in inhibition of cell growth. In certain embodiments, SRR G-1, or a derivative thereof, has about a 6.5 fold or greater increase in inhibition of cell growth. In certain embodiments, SRR G-1, or a derivative thereof, has about a 7 fold or greater increase in inhibition of cell growth. In certain embodiments, SRR G-1, or a derivative thereof, has about a 7.5 fold or greater increase in inhibition of cell growth. In certain embodiments, SRR G-1, or a derivative thereof, has about a 8 fold or greater increase in inhibition of cell growth. In certain embodiments, SRR G-1, or a derivative thereof, has about a 8.5 fold or greater increase in inhibition of cell growth. In certain embodiments, SRR G-1, or a derivative thereof, has about a 9 fold or greater increase in inhibition of cell growth. In certain embodiments, SRR G-1, or a derivative thereof, has about a 9.5 fold or greater increase in inhibition of cell growth. In certain embodiments, SRR G-1, or a derivative thereof, has about a 10 fold or greater increase in inhibition of cell growth. Or a range between any two of these values.

In certain embodiments the compound of SRR G-1, or a derivative thereof, substantially free of its opposite enantiomer and at a concentration of 500 nM has about a 7.8 fold or greater increase in inhibition of cell growth in a YUMM1.7 4 day growth assay as compared to a racemic mixture of SRR G-1 and its opposite enantiomer.

In any of the embodiments of SRR G-1 described herein, SRR G-1, or a derivative thereof, and at a concentration of 500 nM has about a 5 fold or greater increase in inhibition of cell growth in a YUMM1.7 4 day growth assay as compared the opposite enantiomer of SRR G-1, or a derivative thereof. In certain embodiments, SRR G-1, or a derivative thereof, has about a 10 fold or greater increase in inhibition of cell growth. In certain embodiments, SRR G-1, or a derivative thereof, has about a 15 fold or greater increase in inhibition of cell growth. In certain embodiments, SRR G-1, or a derivative thereof, has about a 20 fold or greater increase in inhibition of cell growth. In certain embodiments, SRR G-1, or a derivative thereof, has about a 25 fold or greater increase in inhibition of cell growth. In certain embodiments, SRR G-1, or a derivative thereof, has about a 30 fold or greater increase in inhibition of cell growth. In certain embodiments, SRR G-1, or a derivative thereof, has about a 35 fold or greater increase in inhibition of cell growth. In certain embodiments, SRR G-1, or a derivative thereof, has about a 40 fold or greater increase in inhibition of cell growth. In certain embodiments, SRR G-1, or a derivative thereof, has about a 45 fold or greater increase in inhibition of cell growth. In certain embodiments, SRR G-1, or a derivative thereof, has about a 50 fold or greater increase in inhibition of cell growth. In certain embodiments, SRR G-1, or a derivative thereof, has about a 55 fold or greater increase in inhibition of cell growth. In certain embodiments, SRR G-1, or a derivative thereof, has about a 60 fold or greater increase in inhibition of cell growth. In certain embodiments, SRR G-1, or a derivative thereof, has about a 65 fold or greater increase in inhibition of cell growth. In certain embodiments, SRR G-1, or a derivative thereof, has about a 70 fold or greater increase in inhibition of cell growth. In certain embodiments, SRR G-1, or a derivative thereof, has about a 75 fold or greater increase in inhibition of cell growth. Or a range between any two of these values.

In certain embodiments the compound of SRR G-1, or a derivative thereof, substantially free of its opposite enantiomer and at a concentration of 500 nM has about a 39.5 fold or greater increase in inhibition of cell growth in a YUMM1.7 4 day growth assay as compared to the opposite enantiomer of SRR G-1, or a derivative thereof.

In any of the embodiments described herein, SRR G-1, or a derivative thereof, possess greater desired pharmacological activity as compared to RSS G-1, or a derivative thereof. In any of the embodiments described herein, the presence of RSS G-1, or a derivative thereof, would add to the undesired pharmacological activity of a combination therapy with SRR G-1.

Pharmaceutical Compositions

Some embodiments herein are directed to a pharmaceutical or cosmetic composition comprising an enantiomerically purified SRR G-1, or a derivative thereof, of embodiments herein and a pharmaceutically or cosmetically acceptable carrier, adjuvant, or vehicle.

In some embodiments, the pharmaceutical or cosmetic compositions comprising an enantiomerically purified SRR G-1, or a derivative thereof, for use in accordance with embodiments herein can be formulated in conventional manner using one or more pharmaceutical or cosmetically acceptable carriers or excipients.

The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical or cosmetic compositions comprising an enantiomerically purified SRR G-1, or a derivative thereof, disclosed herein may be manufactured in any manner known in the art, e.g., by means of conventional mixing, dissolving, suspending, granulating, dragee-making, levigating, emulsifying, encapsulating, entrapping or compression processes.

Pharmaceutical or cosmetic compositions comprising an enantiomerically purified SRR G-1, or a derivative thereof, include those suitable for oral, rectal, nasal, topical (including dermal, buccal, sublingual and intraocular), vaginal or parenteral (including intramuscular, sub-cutaneous and intravenous) administration. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods well-known in the art.

In the pharmaceutical composition comprising an enantiomerically purified SRR G-1, or a derivative thereof, embodiments of the present invention, the compound(s) according to the present invention is formulated preferably in admixture with a pharmaceutically acceptable carrier. In general, it is preferable to administer the pharmaceutical composition comprising an enantiomerically purified SRR G-1, or a derivative thereof, orally, but certain pharmaceutical compositions comprising an enantiomerically purified SRR G-1, or a derivative thereof, may be preferably administered parenterally and in particular, in intravenous or intramuscular dosage form, as well as via other parenteral routes, such as transdermal, buccal, subcutaneous, suppository or other route, including via inhalation or intranasally. Oral dosage forms are preferably administered in tablet or capsule (preferably, hard or soft gelatin or other protein or polymer capsule) form. Intravenous and intramuscular pharmaceutical compositions comprising an enantiomerically purified SRR G-1, or a derivative thereof, are preferably administered in sterile saline. Of course, one of ordinary skill in the art may modify the formulations within the teachings of the specification to provide numerous pharmaceutical compositions comprising an enantiomerically purified SRR G-1, or a derivative thereof, for a particular route of administration without rendering the compositions of the present invention unstable or compromising their therapeutic activity.

Pharmaceutical compositions comprising an enantiomerically purified SRR G-1, or a derivative thereof, suitable for parenteral injection may comprise physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants.

These pharmaceutical or cosmetic compositions comprising an enantiomerically purified SRR G-1, or a derivative thereof, may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical or cosmetic compositions comprising an enantiomerically purified SRR G-1, or a derivative thereof, can be brought about by the use of agents capable of delaying absorption, for example, aluminum monostearate and/or gelatin.

Solid dosage forms of pharmaceutical compositions comprising an enantiomerically purified SRR G-1, or a derivative thereof, for oral administration include capsules, tablets, powders, granules, stabilization in a polymer glass, dissolution in a lipid type liquid, dissolution in a solidified liquid, and dissolution in a self-emulsifying lipid. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid pharmaceutical compositions comprising an enantiomerically purified SRR G-1, or a derivative thereof, of a similar type may also be used as fillers in soft or hard filled gelatin capsules using such excipients as lactose or milk sugar, as well as high molecular weight polyethylene glycols, and the like.

Solid dosage forms of pharmaceutical compositions comprising an enantiomerically purified SRR G-1, or a derivative thereof, such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Liquid dosage forms of pharmaceutical compositions comprising an enantiomerically purified SRR G-1, or a derivative thereof, for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame seed oil, glycerol, tetrahydrofurfuryl alcohol, polyethylene glycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Pharmaceutical compositions comprising an enantiomerically purified SRR G-1, or a derivative thereof, for rectal or vaginal administration, where applicable, can be prepared by mixing an active agent and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active.

Dosage forms of pharmaceutical or cosmetic compositions comprising an enantiomerically purified SRR G-1, or a derivative thereof, for topical administration include ointments, powders, sprays inhalants, and drops suitable for administration to the eye, ear or nose. The compound(s) are admixed under sterile conditions with a physiologically acceptable carrier, and any preservatives, buffers, and/or propellants that may be required. Opthalmic formulations, eye ointments, powders, and solutions are also contemplated as being within the scope of this invention.

In some embodiments, the pharmaceutical or cosmetic compositions comprising an enantiomerically purified SRR G-1, or a derivative thereof, for use in accordance with embodiments herein additionally include at least one sunblocking agent. In certain embodiments, the pharmaceutical composition further comprises at least sunscreen lotion. In oilier embodiments, the pharmaceutical or cosmetic composition comprises a formulated sunblock or sunscreen lotion and enantiomerically purified SRR G-1, or a derivative thereof.

The active compound or pharmaceutical or cosmetic composition comprising an enantiomerically purified SRR G-1, or a derivative thereof, can be effective over a wide dosage range and can be generally administered in a therapeutically effective amount. It will be understood, however, that the amount of the compound or composition actually administered will usually be determined by a physician, according to the relevant circumstances, including the condition to be treated, the chosen route of administration, the actual compound or composition administered, the age, weight, and response of the individual patient, the severity of the patient's symptoms, and the like.

In some embodiments, the pharmaceutical or cosmetic composition comprising an enantiomerically purified SRR G-1, or a derivative thereof, may comprise about 0.001% to about 50% of one or more compounds or compositions disclosed herein. In some embodiments, the one or more compounds or compositions is in an amount of about 0.001% to about 50%, about 0.001% to about 45%, about 0.001% to about 40%, about 0.001% to about 30%, about 0.001% to about 20%, about 0.001% to about 10%, about 0.001% to about 5%, about 0.01% to about 50%, about 0.01% to about 45%, about 0.01% to about 40%, about 0.01% to about 30%, about 0.01% to about 20%, about 0.01% to about 10%, about 0.01% to about 5%, about 0.05% to about 50%, about 0.05% to about 45%, about 0.05% to about 40%, about 0.05% to about 30%, about 0.05% to about 20%, about 0.05% to about 10%, about 0.1% to about 50%, about 0.1% to about 45%, about 0.1% to about 40%, about 0.1% to about 30%, about 0.1% to about 20%, about 0.1% to about 10%, about 0.1% to about 5%, about 0.5% to about 50%, about 0.5% to about 45%, about 0.5% to about 40%, about 0.5% to about 30%, about 0.5% to about 20%, about 0.5% to about 10%, about 0.5% to about 5%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.001%, about 0.01%, about 0.05%, about 0.1%, about 0.25%, about 0.5%, about 0.75%, about 1%, about 5%, about 10%, about 15%, about 20%, about 25%, about 30%, about 35%, about 40%, about 45%, about 50%, about 60%, about 70%, about 80%, about 90%, or a range between any two of these values. The foregoing all representing weight percentages of the composition. In some embodiments, the composition is suitable for topical administration. In some embodiments, the composition is suitable for oral administration. In some embodiments, the composition is suitable for oral, parenteral (including subcutaneous, intradermal, intramuscular, intravenous, intraarticular, and intramedullary), intraperitoneal, transmucosal, transdermal, rectal, intranasal, topical (including dermal, buccal, sublingual and intraocular), or intravaginal administration.

In some embodiments, the compound or pharmaceutical or cosmetic compositions comprising an enantiomerically purified SRR G-1, or a derivative thereof, is in a therapeutically effective amount. In some embodiments, the therapeutically effective amount may be about 0.01 mg to about 1000 mg, about 0.01 mg to about 900 mg, about 0.01 mg to about 800 mg, about 0.01 mg to about 700 mg, about 0.01 mg to about 600 mg, about 0.01 mg to about 500 mg, about 0.01 mg to about 400 mg, about 0.01 mg to about 300 mg, about 0.01 mg to about 200 mg, about 0.01 mg to about 100 mg, 0.1 mg to about 1000 mg, about 0.1 mg to about 900 mg, about 0.1 mg to about 800 mg, about 0.1 mg to about 700 mg, about 0.1 mg to about 600 mg, about 0.1 mg to about 500 mg, about 0.1 mg to about 400 mg, about 0.1 mg to about 300 mg, about 0.1 mg to about 200 mg, about 0.1 mg to about 100 mg, about 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values. Specific examples include, for example, about 1000 mg, about 900 mg, about 800 mg, about 700 mg, about 750 mg, about 600 mg, about 500 mg, about 400 mg, about 450 mg, about 300 mg, about 250 mg, about 200 mg, about 175 mg, about 150 mg, about 125 mg, about 120 mg, about 110 mg, about 100 mg, about 90 mg, about 80 mg, about 70 mg, about 60 mg, about 50 mg, about 30 mg, about 20 mg, about 10 mg, about 5 mg, about 1 mg, about 0.1 mg, about 0.01 mg, or any value between the ranges disclosed above.

In some embodiments, the therapeutically effective amount can vary according to, for example, the particular use for which the treatment is made, the manner of administration of the compound or composition, the health and condition of the patient, and the judgment of the prescribing physician. The proportion or concentration of a compound or composition in a pharmaceutical or cosmetic composition comprising an enantiomerically purified SRR G-1, or a derivative thereof, can vary depending upon a number of factors including dosage, chemical characteristics (e.g., hydrophobicity), and the route of administration. For example, the compounds or compositions can be provided in an aqueous physiological buffer solution containing about 0.1 to about 10% w/v of the compound or composition for parenteral administration. Some typical dose ranges for the compounds or compositions are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound or composition selected, formulation of the excipient, and its route of administration. Effective doses can be extrapolated from dose-response curves derived from in vitro or animal model test systems.

The amount of compound or pharmaceutical or cosmetic composition comprising an enantiomerically purified SRR G-1, or a derivative thereof, administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

In any of the pharmaceutical compositions comprising an enantiomerically purified SRR G-1, or a derivative thereof, described herein may have one or more additional therapeutic agents.

The additional therapeutic agents may be selected from the group, but is not limited to, consisting of a weight loss drug, an antihyperglycemic drug, an insulin sensitizer, a glucagon-like peptide 1 (GLP1) receptor agonist, a sodium glucose cotransporter 2 (SGLT2) inhibitor, insulin, an insulin analogue, sulfonylureas, a dipeptidyl peptidase 4 (DPP4) inhibitor, an alphaglucosidase inhibitor (AGI), a bile acid sequestrant (BAS), sympatholytic dopamine receptor agonist, incretins, a hypertension drug, a lipid-modifying agent, an anti-obesity agent, an immunotherapy agent, a chemotherapy agent, a targeted kinase inhibitor, a histone deacetylase inhibitor, an anti-infective agent, a bromodomain inhibitor, and combinations thereof.

The immunotherapy agent may be selected from the group, but is not limited to, consisting of PD-1 inhibitors (Pembrolizumab, Nivolumab, anti-PD-1), PD-L1 inhibitors (i.e. Atezolizumab, Avelumab, Durvalumab, anti-PD-L1), CTLA-4 inhibitors (i.e. Ipilimumab, anti-B7-1/B7-2, anti-CTLA-4), IL-2, IL-7, IL-12, Oncolytic Viruses (Talimogene Laherparepvec), cytosine phosphate-guanosine, oligodeoxynucleotides, Imiquimod, Resiquimod, and antibodies targeting T cell immunoreceptor with Ig and ITIM domains (TIGIT), inducible co-stimulator (ICOS), Lymphocyte activation gene 3 (LAG-3), T-cell immunoglobulin and Mucin domain containing molecule 3 (TIM3), V-domain containing IG supressor of T cella ctivation (VISTA), OX40, Glucocorticoid-induced TNF receptor (GITR), CD40, CD47, CD94/NKG2A, Killer immunoglobulin receptor (KIR), and combinations thereof.

The chemotherapy agent may be selected from the group, but is not limited to, consisting of Cyclophosphamide, methotrexate, 5-fluorouracil, Doxorubicin, Docetaxel, bleomycin, vinblastine, dacarbazine, Mustine, vincristine, procarbazine, etoposide, cisplatin, Epirubicin, capecitabine, folinic acid, oxaliplatin, temozolomide, taxanes, and combinations thereof.

The targeted kinase inhibitor may be selected from the group, but is not limited to, consisting of Vemurafenib, Dabrafenib, Trametinib, Vandetanib, SU6656, Sunitinib, Sorafenib, Selumetinib, Ruxolitinib, Pegaptanib, Pazopanib, Nilotinib, Mubritinib, Lenvatinib, Lapatinib, Imatinib, Ibrutinib, Gefitinib, Fostamatinib, Erlotinib, Erdafitinib, Dasatinib, Cabozantinib, Crizotinib, Cobimetinib, Cetuximab, Bosutinib, Binimetinib, Axitinib, Afatinib, Adavosertib, and combinations thereof.

The histone deacetylase inhibitor may be selected from the group, but is not limited to, consisting of Vorinostat, Romidepsin, Chidamide, Panobinostat, Belinostat, Valproic acid, Givinostat, and combinations thereof.

The anti-infective agent may be selected from the group, but is not limited to, consisting of oritavancin (Orbactiv), dalvavancin (Dalvance), tedizolid phosphate, (Sivextro), clindamycin, linezolid (Zyvox), mupirocin (Bactroban), trimethoprim, sulfamethoxazole, trimethoprim-sulfamethoxazole (Septra or Bactrim), a tetracycline, vancomycin, daptomycin, fluoroquinolines, and combinations thereof.

The bromodomain inhibitor may be selected from the group, but is not limited to, consisting of OTX015/MK-8628, CPI-0610, BMS-986158, ZEN003694, GSK2820151, GSK525762, INCB054329, INCB057643, ODM-207, RO6870810, BAY1238097, CC-90010, AZD5153, FT-1101, ABBV-744, RVX-000222, and combinations thereof.

Methods of Use

Provided herein is a method of treating or preventing a disease or disorder in a subject in need thereof comprising administering to a subject a therapeutically effective amount of a compound or pharmaceutical composition comprising enantiomerically purified SRR G-1, or a derivative thereof, according to any embodiment disclosed herein.

Methods of treating or preventing a disease or disorder in a subject in need thereof comprising administering to a subject a therapeutically effective amount of a compound or pharmaceutical composition comprising enantiomerically purified SRR G-1, or a derivative thereof, described herein where treatment with SRR G-1 is acting as an adjuvant prior to, with, or after one or more additional therapies selected from surgical therapy, chemotherapy, anti-PD-1 therapy, targeted molecular or anti-proliferative therapy or radiofrequency ablation therapy.

Some embodiments describe a method wherein the cancer or cells causing or involved in the disease or disorder expresses GPER.

In any embodiments described herein the subject is a human or an animal.

In some embodiments, said disease or disorder is selected from the group consisting of cancer, endometritis, prostatitis, polycystic ovarian syndrome, urinary incontinence, hormone-related disorders, hearing disorders, hot flashes, profuse sweating, hypertension, stroke, ischemia, myocardial infarction, dilated cardiomyopathy, obesity, insulin resistance, osteoporosis, atherosclerosis, symptoms of menopause, inflammation, rheumatoid arthritis, osteoarthritis, lymphoproliferative disorders, myeloproliferative disorders, eosinophilia, histiocytosis, paroxysmal nocturnal hemoglobinuria, systemic mastocytosis, venous thrombosis, embolisms, depression, insomnia, anxiety, neuropathy, multiple sclerosis, Parkinson's disease, Alzheimer's disease, inflammatory bowel disease, Crohn's disease, celiac disease, proteinuric renal disease, vascular disease, and thymic atrophy.

Some embodiments describe a method of preventing or reducing the likelihood of pregnancy after intercourse comprising administering to a subject a therapeutically effective amount of a compound or composition, or a derivative thereof, according to any embodiment disclosed herein.

Some embodiments describe a method of restoring the lipid profile in a subject in need thereof comprising administering to a subject a therapeutically effective amount of a compound or composition, or a derivative thereof, according to any embodiment disclosed herein.

Some embodiments describe a method of treating or preventing type 2 diabetes in a subject in need thereof comprising administering to a subject a therapeutically effective amount of a compound or composition, or a derivative thereof, according to any embodiment disclosed herein.

Type 2 diabetes is a disease diagnosed by a set of characteristics selected from the group consisting of an A1C level of greater than or equal to 6.5%, a fasting plasma glucose (FPG) amount of greater than 126 mg/dL, and an oral glucose tolerance test (OGTT) amount of greater than 200 mg/dL. Subjects with type 2 diabetes are at higher risk of developing dyslipidemia, hypertension, and artherosclerotic cardiovascular disease (ASCVD). In embodiments, the subject is treated by the administration of compound or composition, or a derivative thereof, according to any embodiment disclosed herein wherein the symptoms of diabetes is treated. In embodiments, the subject is treated by the administration of a compound or composition, or a derivative thereof, according to any embodiment disclosed herein wherein the A1C level is reduced to less than 6.5%, between 6.4% and 5.7%, or less than 5.7%. In embodiments, the subject is treated by the administration of a compound or composition, or a derivative thereof, according to any embodiment disclosed herein wherein the fasting plasma glucose (FPG) is reduced to less than 126 mg/dL, between 125 mg/dL to 110 mg/dL, less than 110 mg/dL, or less than 100 mg/dL. In embodiments, the subject is treated by the administration of a compound or composition, or a derivative thereof, according to any embodiment disclosed herein wherein the oral glucose tolerance test (OGTT) is reduced to less than 200 mg/dL, between 199 mg/dL and 140 mg/dL, or less than 140 mg/dL. In embodiments, the subject is treated by the administration of a compound or composition, or a derivative thereof, according to any embodiment disclosed herein wherein the blood pressure is reduced to less than 130/80 mmHg, less than 120/80 mmHg, less than 110/80 mmHg, or less than 100/80 mmHg. In embodiments, the subject is treated by the administration of a compound or composition, or a derivative thereof, according to any embodiment disclosed herein wherein the blood glucose level is reduced to less than 70 mg/dL, or less than 50 mg/dL. In embodiments, the subject is treated by the administration of a compound or composition, or a derivative thereof, according to any embodiment disclosed herein wherein the risk of developing dyslipidemia, hypertension, or artherosclerotic cardiovascular disease (ASCVD) is reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Pre-diabetes is diagnosed based upon a set of characteristics selected from the group consisting of an A1C level of about 5.7% to about 6.4%, a fasting plasma glucose (FPG) amount of about 100 mg/dL to about 125 mg/dL, and an oral glucose tolerance test (OGTT) amount of about 140 mg/dL to about 200 mg/dL. A pre-diabetic subject can also be diagnosed with impaired glucose tolerance, impaired fasting glucose, or insulin resistance. Subjects with pre-diabetes are at higher risk of developing hyperglycemia, dyslipidemia, hypertension, artherosclerotic cardiovascular disease (ASCVD), cardiometabolic disease, chronic kidney disease, early nephropathy, retinopathy, cardiovascular disease and biomechanical complications. In embodiments, the subject is treated by the administration of a compound or composition, or a derivative thereof, according to any embodiment disclosed herein wherein the symptoms of pre-diabetes is treated. In embodiments, the subject is treated by the administration of a compound or composition, or a derivative thereof, according to any embodiment disclosed herein wherein the A1C level is reduced to less than 6.4%, or less than 5.7%. In embodiments, the subject is treated by the administration of a compound or composition, or a derivative thereof, according to any embodiment disclosed herein wherein the fasting plasma glucose (FPG) is reduced to less than 125 mg/dL, less than 110 mg/dL, or less than 100 mg/dL. In embodiments, the subject is treated by the administration of a compound or composition, or a derivative thereof, according to any embodiment disclosed herein wherein the oral glucose tolerance test (OGTT) is reduced to less than 199 mg/dL, or less than 140 mg/dL. In embodiments, the subject is treated by the administration of a compound or composition, or a derivative thereof, according to any embodiment disclosed herein wherein the blood pressure is reduced to less than 130/80 mmHg, less than 120/80 mmHg, less than 110/80 mmHg, or less than 100/80 mmHg. In embodiments, the subject is treated by the administration of a compound or composition, or a derivative thereof, according to any embodiment disclosed herein wherein the blood glucose level is reduced to less than 70 mg/dL, or less than 50 mg/dL. In embodiments, the subject is treated by the administration of a compound or composition, or a derivative thereof, according to any embodiment disclosed herein wherein the risk of developing hyperglycemia, dyslipidemia, hypertension, artherosclerotic cardiovascular disease (ASCVD), cardiometabolic disease, chronic kidney disease, early nephropathy, retinopathy, cardiovascular disease or biomechanical complications is reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Conditions characterized by an increase in the levels of A1C, glucose, insulin, homeostasis model of assessment of insulin resistance (HOMA-IR), urinary 8-iso-PGF2a, oxidative stress in adipose tissue, and carbonylation of GLUT4 lead to a diagnosis of impaired glucose tolerance, impaired fasting glucose, insulin resistance, pre-diabetes, or type 2 diabetes. Subjects with a condition as described herein are at higher risk of developing pre-diabetes, type 2 diabetes, hyperglycemia, dyslipidemia, hypertension, artherosclerotic cardiovascular disease (ASCVD), cardiometabolic disease, chronic kidney disease, early nephropathy, retinopathy, cardiovascular disease and biomechanical complications. In embodiments, the subject is treated by the administration of a compound or composition, or a derivative thereof, according to any embodiment disclosed herein wherein the symptoms of the condition is treated. In embodiments, the subject is treated by the administration of a compound or composition, or a derivative thereof, according to any embodiment disclosed herein wherein the A1C level is reduced to less than 6.4%, or less than 5.7%. In embodiments, the subject is treated by the administration of a compound or composition, or a derivative thereof, according to any embodiment disclosed herein wherein the fasting plasma glucose (FPG) is reduced to less than 125 mg/dL, less than 110 mg/dL, or less than 100 mg/dL. In embodiments, the subject is treated by the administration of a compound or composition, or a derivative thereof, according to any embodiment disclosed herein wherein the oral glucose tolerance test (OGTT) is reduced to less than 199 mg/dL, or less than 140 mg/dL. In embodiments, the subject is treated by the administration of a compound or composition, or a derivative thereof, according to any embodiment disclosed herein wherein the blood pressure is reduced to less than 130/80 mmHg, less than 120/80 mmHg, less than 110/80 mmHg, or less than 100/80 mmHg. In embodiments, the subject is treated by the administration of a compound or composition, or a derivative thereof, according to any embodiment disclosed herein wherein the blood glucose level is reduced to less than 70 mg/dL, or less than 50 mg/dL. In embodiments, the subject is treated by the administration of a compound or composition, or a derivative thereof, according to any embodiment disclosed herein wherein the risk of developing pre-diabetes, type 2 diabetes, hyperglycemia, dyslipidemia, hypertension, artherosclerotic cardiovascular disease (ASCVD), cardiometabolic disease, chronic kidney disease, early nephropathy, retinopathy, cardiovascular disease and biomechanical complications is reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In embodiments, the one or more additional therapeutic agents may be selected from the group consisting of a weight loss drug, an antihyperglycemic drug, an insulin sensitizer, a glucagon-like peptide 1 (GLP1) receptor agonist, a sodium glucose cotransporter 2 (SGLT2) inhibitor, insulin, an insulin analogue, sulfonylureas, a dipeptidyl peptidase 4 (DPP4) inhibitor, an alphaglucosidase inhibitor (AGI), a bile acid sequestrant (BAS), sympatholytic dopamine receptor agonist, incretins, a hypertension drug, a lipid-modifying agent, and combinations thereof.

In embodiments, the weight loss drug is selected from the group consisting of diethyproprion, phendimetrazine, phentermine, orlistat, phentermine/topiramate extended release (ER), lorcaserin, naltrexone ER/bupropion ER, and liraglutide. In embodiments, diethyproprion is administered at 25 mg. In embodiments, phendimetrazine is administered at 35 mg or 105 mg. In embodiments, phentermine is administered at 8 mg, 15 mg, 30 mg, or 37.5 mg. In embodiments, orlistat is administered at 60 mg or 120 mg. In embodiments, phentermine/topiramate extended release is administered at phentermine 3.75 mg/topiramate 23 mg, phentermine 7.5 mg/topiramate 46 mg daily, or phentermine 15 mg/topiramate 92 mg. In embodiments, lorascerin is administered at 10 mg or 20 mg. In embodiments, naltrexone ER/bupropion ER is administered at 8 mg naltrexone/90 mg bupropion. In embodiments, liraglutide is administered at 1.2 mg, 1.8 mg, or 3 mg.

In embodiments, the antihyperglycemic drug is selected from the group consisting of metformin and acarbose. In embodiments, metformin is administered at 500 mg, 625 mg, 750 mg, 850 mg, 2000 mg, 2500 mg, or 1 gram. In embodiments, acarbose is administered at 25 mg, 50 mg, or 100 mg.

In embodiments, the insulin sensitizer is selected from the group consisting of thiazolidinediones (TZDs), pioglitazone, and rosiglitazone. In embodiments, pioglitazone is administered at 15 mg, 30 mg, or 45 mg. In embodiments, rosiglitazone is administered at 2 mg, 4 mg, or 8 mg.

In embodiments, the glucagon-like peptide 1 (GLP1) receptor agonist is selected from the group consisting of liraglutide, exenatide, albiglutide, and dulaglutide. In embodiments, liraglutide is administered at 1.2 mg, 1.8 mg, or 3 mg. In embodiments, exenatide is administered at 2 mg. In embodiments, albiglutide is administered at 30 mg or 50 mg. In embodiments, dulaglutide is administered at 0.75 mg or 1.5 mg.

In embodiments, the sodium glucose cotransporter 2 (SGLT2) inhibitor is selected from the group consisting of empagliflozin, canagliflozin, and dapagliflozin. In embodiments, empagliflozin is administered at 5 mg, 10 mg, 12.5 mg, or 25 mg. In embodiments, canagliflozin is administered at 50 mg, 100 mg, 150 mg, or 300 mg.

In embodiments, the insulin is selected from the group consisting of insulin analogues, basal insulin analogues, neutral protamine Hagedorn (NPH), rapid acting insulin analogues, and inhaled insulin.

In embodiments, the insulin analogue is selected from the group consisting of glargine, degludec, and detemir. In embodiments, glargine is administered at 100 units or 300 units. In embodiments, degludec is administered at 30 units, 100 units, 200 units, 300 units, or 600 units. In embodiments, detemir is administered at 100 units or 300 units.

In embodiments, the rapid acting insulin analogue is selected from the group consisting of lispro, aspart, and glulisine. In embodiments, lispro is administered at 50 units, 75 units, 100 units, 300 units, or 1000 units. In embodiments, aspart is administered at 50 units, 90 units, 210 units, 300 units, 700 units, or 1000 units. In embodiments, glulisine is administered at 300 units or 1000 units.

In embodiments, the sulfonylureas is selected from the group consisting of acetohexamide, carbutamide, chlorpropamide, glycyclamide (tolhexamide), metahexamide, tolazamide, tolbutamide, glibenclamide (glyburide), glibornuride, gliclazide, glipizide, gliquidone, glisoxepide, glyclopyramide, and glimepiride. In embodiments, acetohexamide is administered at 250 mg or 500 mg. In embodiments, carbutamide is administered at 250 mg or 500 mg. In embodiments, chlorpropamide is administered at 100 mg or 250 mg. In embodiments, tolazamide is administered at 100 mg, 250 mg, or 500 mg. In embodiments, tolbutamide is administered at 250 mg or 500 mg. In embodiments, glibenclamide is administered at 5 mg. In embodiments, glipizide is administered at 2.5 mg, 5 mg, or 10 mg. In embodiments, glimepiride is administered at 1 mg, 2 mg, 3 mg, 4 mg, 6 mg, or 8 mg.

In embodiments, the dipeptidyl peptidase 4 (DPP4) inhibitor is selected from the group consisting of linagliptin, saxagliptin, and alogliptin. In embodiments, linagliptin is administered at 2.5 mg, 5 mg, 10 mg, or 25 mg. In embodiments, saxagliptin is administered at 2.5 mg or 5 mg. In embodiments, alogliptin is administered at 6.25 mg, 12.5 mg, or 25 mg.

In embodiments, the alpha glucosidase inhibitor (AGI) is selected from the group consisting of acarbose, miglitol, and voglibose. In embodiments, acarbose is administered at 25 mg, 50 mg, or 100 mg. In embodiments, miglitol is administered at 25 mg, 50 mg, or 100 mg. in embodiments, voglibose is administered at 0.2 mg or 0.3 mg.

In embodiments, the bile acid sequestrant (BAS) is selected from the group consisting of cholestyramine, colestipol, and colesevelam. In embodiments, cholestyramine is administered at 800 mg, 1 gram, or 4 grams. In embodiments, colestipol is administered at 1 gram or 5 grams. In embodiments, colesevelam is administered at 375 mg, 625 mg, 1.875 grams, or 3.75 grams.

In embodiments, the sympatholytic dopamine receptor agonist is bromocriptine mesylate. In embodiments, bromocriptine mesylate is administered at 0.8 mg, 2.5 mg, or 5 mg.

In embodiments, the hypertension drug is selected from the group consisting of angiotensin-converting enzyme inhibitors (ACEIs), angiotensin II receptor blockers (ARBs), beta blockers, calcium channel blockers (CCBs), and thiazide diuretics.

In embodiments, the lipid-modifying agent is selected from the group consisting of ezetimibe, simvastatin, monoclonal antibody inhibitors of proprotein convertase subtilisin-kexin type 9 serine protease (PCSK9), evolocumab, alirocumab, fibrates, niacin, eicosapentaenoic acid (EPA), docosahexaenoic acid (DHA) and omega-3 fatty acids. In embodiments, ezetimibe is administered at 10 mg. In embodiments, simvastatin is administered at 5 mg, 10 mg, 20 mg, 40 mg, or 80 mg. In embodiments, evolocumab is administered at 140 mg or 420 mg. In embodiments, alirocumab is administered at 75 mg, 150 mg, or 300 mg. In embodiments, niacin is administered at 375 mg, 500 mg, 750 mg, or 1 gram.

Treatment efficacy may be assessed by measuring the level of insulin in the blood. A normal fasting insulin level is below 5. A fasting insulin level around 8.0 results in twice the risk of pre-diabetes, and a fasting insulin of about 25 results in about a five times the risk of prediabetes. In embodiments, administration of a compound or composition, or a derivative thereof, according to any embodiment disclosed herein to a subject in need thereof decreases the fasting insulin level is less than 5, less than 8, or less than 25.

Urinary 8-iso-PGF2α is a well-established marker of oxidative stress-induced lipid peroxidation. A rise in urinary 8-iso-PGF2α indicates the development of systemic oxidative stress. Treatment efficacy may be assessed by measuring the level of urinary 8-iso-PGF2α in adipose tissue. In embodiments, administration of a compound or composition, or a derivative thereof, according to any embodiment disclosed herein to a subject in need thereof decreases the level of urinary 8-iso-PGF2α.

Treatment efficacy may be assessed by measuring the level of oxidative stress in adipose tissue. Oxidative stress is measured by an increase in any one of the following enzymes: superoxide dismutase 2 (SOD2), catalase, glutathione peroxidase, peroxiredoxin, aldehyde dehydrogenase, aldo-keto reductase, and glutathione S-transferase. In embodiments, administration of a compound or composition, or a derivative thereof, according to any embodiment disclosed herein to a subject in need thereof decreases the level of one or more of the following enzymes: superoxide dismutase 2 (SOD2), catalase, glutathione peroxidase, peroxiredoxin, aldehyde dehydrogenase, aldo-keto reductase, and glutathione S-transferase.

Treatment efficacy may be assessed by measuring the level of carbonylation of GLUT4. In adipose tissue during overnutrition, oxidative stress results in extensive oxidation and carbonylation of numerous proteins, including carbonylation of GLUT4 near the glucose transport channel, which results in the loss of GLUT4 activity. The carbonylation and oxidation-induced inactivation of GLUT4 may result in insulin resistance. In embodiments, administration of a compound or composition, or a derivative thereof, according to any embodiment disclosed herein to a subject in need thereof decreases the level of GLUT4 carbonylation.

Some embodiments describe a method of treating or preventing cancer, preventing the reoccurrence of cancer, inhibiting the progression of cancer, shrinking a cancer prior to additional therapy, or reducing circulating tumor cells or metastases prior to additional therapy in a subject in need thereof comprising administering to a subject a therapeutically effective amount of a compound or composition, or a derivative thereof, according to any embodiment disclosed herein.

In some embodiments, said cancer is selected from the group consisting of reproductive cancers, hormone-dependent cancers, leukemia, colorectal cancer, prostate cancer, breast cancer, ovarian carcinoma, endometrial cancer, uterine carcinosarcoma, stomach cancer, rectal cancer, liver cancer, pancreatic cancer, lung cancer, uterine cancer, cervical cancer, cervix uteri cancer, corpus uteri cancer, ovary cancer, testicular cancer, bladder cancer, renal cancer, brain/CNS cancer, head and neck cancer, throat cancer, Hodgkin's disease, non-Hodgkin's lymphoma, multiple myeloma, melanoma, acute leukemia, lymphocytic leukemia, hairy cell leukemia, acute myelogenous leukemia, Ewing's sarcoma, small cell lung cancer, non-small cell lung cancer, choriocarcinoma, rhabdomyosarcoma, Wilms's Tumor, neuroblastoma, cancer of the mouth/pharynx, cancer of the esophagus, cancer of the larynx, kidney cancer, lymphoma, Burkitt lymphoma, sarcoma, angiosarcoma, glioblastoma, medulloblastoma, astrocytoma, and Merkel cell carcinoma.

In particular embodiment, the cancer is selected from the group consisting of melanoma, colorectal cancer, non-small cell lung cancer, and pancreatic cancer.

Some embodiments describe a method increasing, or preventing or reversing loss of, skin pigmentation in a subject in need thereof comprising administering to a subject a therapeutically effective amount of a compound or composition, or a derivative thereof, according to any embodiment disclosed herein.

Some embodiments describe a method of skin protection in a subject in need thereof comprising administering to a subject a therapeutically effective amount of a compound or composition, or a derivative thereof, according to any embodiment disclosed herein.

Some embodiments describe a method of skin protection comprising increasing skin pigmentation in a subject in need thereof comprising administering to a subject a therapeutically effective amount of a compound or composition, or a derivative thereof, according to any embodiment disclosed herein.

Some embodiments describe a method of protection of skin from skin cancer in a subject in need thereof comprising administering to a subject a therapeutically effective amount of a compound or composition, or a derivative thereof, according to any embodiment disclosed herein.

Some embodiments describe a method of protection of skin from skin cancer comprising increasing skin pigmentation in a subject in need thereof comprising administering to a subject a therapeutically effective amount of a compound or composition, or a derivative thereof, according to any embodiment disclosed herein.

In embodiments, the methods may include the co-administration of one or more additional therapeutic agents. In embodiments, co-administration may be part of the same pharmaceutical composition comprising an enantiomerically purified SRR G-1, or a derivative thereof, or separate pharmaceutical compositions comprising an enantiomerically purified SRR G-1, or a derivative thereof, described herein. In embodiments, co-administration may be at the same time, substantially the same time, before or after administration of the compositions described herein.

The additional therapeutic agents may be selected from the group consisting of a weight loss drug, an antihyperglycemic drug, an insulin sensitizer, a glucagon-like peptide 1 (GLP1) receptor agonist, a sodium glucose cotransporter 2 (SGLT2) inhibitor, insulin, an insulin analogue, sulfonylureas, a dipeptidyl peptidase 4 (DPP4) inhibitor, an alpha-glucosidase inhibitor (AGI), a bile acid sequestrant (BAS), sympatholytic dopamine receptor agonist, incretins, a hypertension drug, a lipid-modifying agent, an anti-obesity agent, an immunotherapy agent, a chemotherapy agent, a targeted kinase inhibitor, a histone deacetylase inhibitor, an anti-infective agent, a bromodomain inhibitor, and combinations thereof.

The immunotherapy agent may be selected from the group consisting of PD-1 inhibitors (Pembrolizumab, Nivolumab, anti-PD-1), PD-L1 inhibitors (i.e. Atezolizumab, Avelumab, Durvalumab, anti-PD-L1), CTLA-4 inhibitors (i.e. Ipilimumab, anti-B7-1/B7-2, anti-CTLA-4), IL-2, IL-7, IL-12, Oncolytic Viruses (Talimogene Laherparepvec), cytosine phosphate-guanosine, oligodeoxynucleotides, Imiquimod, Resiquimod, and antibodies targeting T cell immunoreceptor with Ig and ITIM domains (TIGIT), inducible co-stimulator (ICOS), Lymphocyte activation gene 3 (LAG-3), T-cell immunoglobulin and Mucin domain containing molecule 3 (TIM3), V-domain containing IG supressor of T cella ctivation (VISTA), OX40, Glucocorticoid-induced TNF receptor (GITR), CD40, CD47, CD94/NKG2A, Killer immunoglobulin receptor (KIR), and combinations thereof.

The chemotherapy agent may be selected from the group consisting of Cyclophosphamide, methotrexate, 5-fluorouracil, Doxorubicin, Docetaxel, bleomycin, vinblastine, dacarbazine, Mustine, vincristine, procarbazine, etoposide, cisplatin, Epirubicin, capecitabine, folinic acid, oxaliplatin, temozolomide, taxanes, and combinations thereof.

The targeted kinase inhibitor may be selected from the group consisting of Vemurafenib, Dabrafenib, Trametinib, Vandetanib, SU6656, Sunitinib, Sorafenib, Selumetinib, Ruxolitinib, Pegaptanib, Pazopanib, Nilotinib, Mubritinib, Lenvatinib, Lapatinib, Imatinib, Ibrutinib, Gefitinib, Fostamatinib, Erlotinib, Erdafitinib, Dasatinib, Cabozantinib, Crizotinib, Cobimetinib, Cetuximab, Bosutinib, Binimetinib, Axitinib, Afatinib, Adavosertib, and combinations thereof.

The histone deacetylase inhibitor may be selected from the group consisting of Vorinostat, Romidepsin, Chidamide, Panobinostat, Belinostat, Valproic acid, Givinostat, and combinations thereof.

The anti-infective agent may be selected from the group consisting of oritavancin (Orbactiv), dalvavancin (Dalvance), tedizolid phosphate, (Sivextro), clindamycin, linezolid (Zyvox), mupirocin (Bactroban), trimethoprim, sulfamethoxazole, trimethoprim-sulfamethoxazole (Septra or Bactrim), a tetracycline, vancomycin, daptomycin, fluoroquinolines, and combinations thereof.

The bromodomain inhibitor may be selected from the group consisting of OTX015/MK-8628, CPI-0610, BMS-986158, ZEN003694, GSK2820151, GSK525762, INCB054329, INCB057643, ODM-207, RO6870810, BAY1238097, CC-90010, AZD5153, FT-1101, ABBV-744, RVX-000222, and combinations thereof.

Experimental Section

Scheme 1

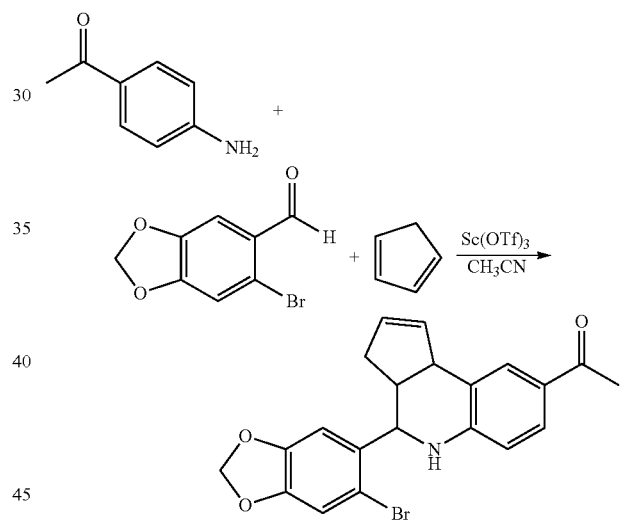

A synthesis of G-1 is described in *Org. Biomol. Chem.*, 2010, 8, 2252-2259, which is hereby incorporated by reference, and depicted in Scheme 1. A catalytic amount of Sc(OTf)$_3$ (0.492 g, 1.0 mmol) in anhydrous acetonitrile (2.0 cm$^3$) was added to the mixture of 6-bromopiperonal (2.30 g, 10.0 mmol), p-aminoacetophenone (1.30 g, 10.0 mmol) and cyclopentadiene (3.30 g, 50.0 mmol) in acetonitrile (25 cm$^3$). The reaction mixture was stirred at ambient temperature (~23° C.) for 2.0 h. The volatiles were removed in vacuo. The residue was purified by preparative silica gel column chromatography using ethyl acetate-hexanes (10:90) to provide G-1 (4.03 g, 98%, d.r.=94:6) as a white solid. The minor diastereomer was substantially removed by recrystallization to yield a racemic mixture of SRR G-1 and RSS G-1.

Example 1: Isolation of the SRR G-1 and RSS G-1 Enantiomers

Starting with a highly purified sample of G-1, (±)1-(4-(6-bromobenzo[d][1,3]dioxol-5-yl)-(3 aS*,4R*,9bR*)-tetrahydro-3H-cyclopenta[c]quinolin-8-yl)ethan-1-one, (99.4% purity) purchased from Tocris Bioscience, the material was dissolved in 90:10:0.1(v/v/v) methyl tert-butyl ether/ethanol/diethyl amine and subjected to preparative chromatography using a column packed with Chrialpak 1A resin. Elution was conducted with 90:10:0.1(v/v/v) methyl tert-butyl ether/ethanol/diethyl amine and the fractions corresponding to each enantiomer were collected and connected to a solid. The early eluting enantiomer was determined to be the SRR G-1 enantiomer by single crystal x-ray structural analysis.

Example 2: SRR G-1 Polymorph Screen

Starting with SRR G-1 prepared according to Example 1, a polymorph screening study was conducted analyzing the solids isolated from slurry of the solid, or from fast and slow evaporation and cooling of solutions (Table 1). Two crystal forms were identified, an anhydrous form designated Form A and mono dichloromethane solvate designated Form B. On exposure to elevated temperature the Form B crystal form desolvates to form the Form C crystal form. Amorphous material was generated from purified SRR G-1 by two different methods; quick evaporating a diethyl ether solution of SRR G-1 or rotary evaporating from a solution of a dichloromethane solution of SRR G-1.

TABLE 1

| Solvent | Method[1] | Observation[2] | Result |
|---|---|---|---|
| acetone | fast evaporation | white, blades and aciculars, B | Form A + peak @ 6.9° |
| | 1. slow evaporation 2. scratched/mixed | 1. crystals in tacky film 2. nucleated, fines, B | Form A |
| | slow cool | fine blades, aciculars, B | Form A |
| ACN | fast evaporation | white, aciculars, B | Form A |
| | slow cool | rosettes of blades, B | Form A |
| | slurry, ambient, 14d | nucleated on stir bar, aciculars, B, left wet | Form A |
| | added 88:12 H$_2$O/ACN | clear, then precipitated | Form A |
| DCM | recrystallization | clear, then precipitated, blades, B | Form B |
| | fast evaporation | blades, B | Form B |
| | 1. rotary evap 2. scraped | 1. foam 2. free flowing, NB | — |
| diethyl ether | fast evaporation evaporation w/N$_2$ | glass, NB fine rosettes | — Form A |
| | fast evaporation | rosettes of aciculars, B | Form A |
| | slurry, ambient,14 days | — | Form A |
| EtOH | fast evaporation | white, fine aciculars, B | Form A |
| | slurry, ambient, 14 days | analyzed as wet cake | Form A |
| | slow cool | aciculars and blades, B analyzed as wet cake | Form A |
| | cooling of solution | — | Form A |
| EtOAc | drop of solvent added to cooled melt | dissolved, fine aciculars and blades, B | — |
| | 1. Fast evaporation 2. scratched | 1. glassy NB 2. aciculars, B | Form A |
| | 1. slow evaporation 2. scratched | 1. glass NB 2. aciculars, B | Form A |
| MeOH | fast evaporation | white, aciculars, B | Form A |
| | slow cool | aggregates blades, B | Form A |
| | slurry, ambient, 14 days | — | Form A |
| | fast evaporation | white, blades, B | Form A |
| IPA | 1. added water, 55:45 IPA/H$_2$O 2. refrigerated, 1 day 4. freezer, 1 day | 1. clear solution 2. lamellae, B 3. blades/tablets, B | Form A |
| | 1. slurry on 100° C. plate 2. seeded w/7615-09-02 3. slow cool | 1. clear (25 mg/ml) 2. seeds remained 3. thin blades, B | Form A |
| THF | 1. fast evaporation 2. scratched | 1. glass, NB 2. opaque | Form A |

TABLE 1-continued

| Solvent | Method[1] | Observation[2] | Result |
|---|---|---|---|
| toluene | 1. fast evaporation 2. scratched | 1. tacky film 2. blades, B | Form A |
| water | slurry, 53° C., 6 days | white | Form A |
| IPA/water 55:45 | filtrate partial evaporation | fine aciculars, B | Form A |
| IPA/H$_2$O 89:11 | filtrate cooling of solution | limited aciculars, B | Form A |
| ACN/H$_2$O 97:03 | filtrate cooling of solution | thin aciculars, B | Form A |

[1]Times and temperatures are approximate unless noted.
[2]B = birefringent and NB = non birefringent when material viewed using polarized light microscopy.

Single Crystal Structure Determination of SRR G-1 (Form B)

Starting with SRR G-1 prepared according to Example 1, a suitable single crystal was grown from dichlormethane solution and analyzed by single-crystal X-ray diffractometry. The structure was determined successfully.

A single crystal was generated from a solution of dichloromethane after an evaporative step. A colorless plate having approximate dimensions of 0.19×0.14×0.03 mm$^3$, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector. Cell constants and an orientation matrix for data collection were obtained from least-squares refinement using the setting angles of 6979 reflections in the range 3.4920°<θ<77.1910°. The space group was determined by the program CRYSALISPRO to be P2$_1$2$_1$2$_1$ (international tables no. 19). The data were collected to a maximum diffraction angle (2θ) of 155.132° at room temperature.

Frames were integrated with CRYSALISPRO. A total of 10119 reflections were collected, of which 4368 were unique. Lorentz and polarization corrections were applied to the data. The linear absorption coefficient is 5.144 mm$^{-1}$ for Cu Kα radiation. An empirical absorption correction using CRYSALISPRO was applied. Transmission coefficients ranged from 0.676 to 1.000. Intensities of equivalent reflections were averaged. The agreement factor for the averaging was 3.4% based on intensity.

The structure was solved by direct methods using S$_{HELXT}$. The remaining atoms were located in succeeding difference Fourier syntheses. The structure was refined using S$_{HELXL}$-2014. Hydrogen atoms on SRR G-1 were refined independently. The dichloromethane hydrogen atoms were included in the refinement but restrained to ride on the atom to which they are bonded. The structure was refined in full-matrix least-squares by minimizing the function:

$$\Sigma w(|F_o|^2 - |F_c|^2)^2$$

where the weight, w, is defined as $1/[\sigma^2(Fo2)+(0.0464 P)^2+(0.1905 P)]$, where $P=(Fo2+2Fc2)/3$. Scattering factors were taken from the "International Tables for Crystallography". Of the 4368 reflections used in the refinements, only the reflections with intensities larger than twice their uncertainty [I>2σ(I)], 4071, were used in calculating the fit residual, R. The final cycle of refinement included 334 variable parameters, 0 restraints, and converged with respective unweighted and weighted agreement factors of:

$$R = \Sigma |F_o - F_c|/\Sigma F_o = 0.0348$$

$$R_w = \sqrt{(\Sigma_w(F_o^2 - F_c^2)^2/\Sigma w(F_o^2)^2)} = 0.0905$$

The standard deviation of an observation of unit weight (goodness of fit) was 1.07. The highest peak in the final difference Fourier had an electron density of 0.398 e/Å$^3$. The minimum negative peak had a value of −0.438 e/Å$^3$.

Calculated X-ray Powder Diffraction (XRPD) Pattern. A calculated XRPD pattern was generated for Cu radiation using MERCURY and the atomic coordinates, space group, and unit cell parameters from the single crystal structure. Atomic Displacement Ellipsoid and Packing Diagrams. The atomic displacement ellipsoid diagram was prepared using MERCURY. Atoms are represented by 50% probability anisotropic thermal ellipsoids. Packing diagrams and additional figures were generated with MERCURY. Hydrogen bonding is represented as dashed lines. Assessment of chiral centers was performed with PLATON. Absolute configuration is evaluated using the specification of molecular chirality rules.

The crystal system is orthorhombic and the space group is P2$_1$2$_1$2$_1$. The cell parameters and calculated volume are: α=6.43156(10) Å, b=13.0752(2) Å, c=25.2941(4) Å, α=90°, β=90°, γ=90°, V=2127.09(6) Å$^3$. Standard uncertainty is written in crystallographic parenthesis notation, e.g. 0.123 (4) is equivalent to 0.123±0.004. The formula weight is 497.20 g mol$^{-1}$ with Z=4, resulting in a calculated density of 1.553 g cm$^{-3}$. Further details of the crystal data and crystallographic data collection parameters are summarized in Table 2. The quality of the structure obtained is high, as indicated by the fit residual, R, of 0.0348 (3.48%). R-factors in the range 2%-6% are quoted to be the most reliably determined structures.

TABLE 2

Crystal Data and Data Collection Parameters SRR G-1 (Form B)

| | |
|---|---|
| Empirical formula | C$_{22}$H$_{20}$BrCl$_2$NO$_3$ |
| Formula weight (g mol$^{-1}$) | 497.20 |
| Temperature (K) | 300.14(10) |
| Wavelength (Å) | 1.54184 |
| Crystal system | orthorhombic |
| Space group | P2$_1$2$_1$2$_1$ |
| Unit cell parameters | |
| a = 6.43156(10) Å | α = 90° |
| b = 13.0752(2) Å | β = 90° |
| c = 25.2941(4) Å | γ = 90° |
| Unit cell volume (Å$^3$) | 2127.09(6) |
| Cell formula units, Z | 4 |
| Calculated density (g cm$^{-3}$) | 1.553 |
| Absorption coefficient (mm$^{-1}$) | 5.144 |
| F(000) | 1008 |
| Crystal size (mm$^3$) | 0.19 × 0.14 × 0.03 |
| Reflections used for cell measurement | 6979 |
| θ range for cell measurement | 3.4920°-77.1910° |
| Total reflections collected | 10119 |
| Index ranges | −8 ≤ h ≤ 7; −13 ≤ k ≤ 16; −31 ≤ l ≤ 29 |
| θ range for data collection | θ$_{min}$ = 3.495°, θ$_{max}$ = 77.566° |
| Completeness to θ$_{max}$ | 97.3% |
| Completeness to θ$_{full}$ = 67.684° | 100% |
| Absorption correction | multi-scan |
| Transmission coefficient range | 0.676-1.000 |
| Refinement method | full matrix least-squares on F$^2$ |
| Independent reflections | 4368 [R$_{int}$ = 0.0340, R$_σ$ = 0.0401] |
| Reflections [1 > 2σ(I)] | 4071 |
| Reflections/restraints/parameters | 4368/0/334 |
| Goodness-of-fit on F$^2$ | S = 1.07 |
| Final residuals [1 > 2σ(I)] | R = 0.0348, R$_w$ = 0.0905 |
| Final residuals [all reflections] | R = 0.0375, R$_w$ = 0.0924 |
| Largest diff. peak and hole (e Å$^{-3}$) | 0.398, −0.438 |
| Max/mean shift/standard uncertainty | 0.001/0.000 |
| Absolute structure determination | Flack parameter: −0.018(13) |
| | Hooft parameter: −0.020(11) |
| | Friedel coverage: 95% |

An atomic displacement ellipsoid drawing of SSR G-1 dichloromethane solvate is shown in FIG. 1. The molecule observed in the asymmetric unit of the single crystal structure is consistent with the proposed molecular structure of the SSR enantiomer. The asymmetric unit shown in FIG. 1 contains one SSR G-1 molecule and one dichloromethane molecule.

Figure 2:
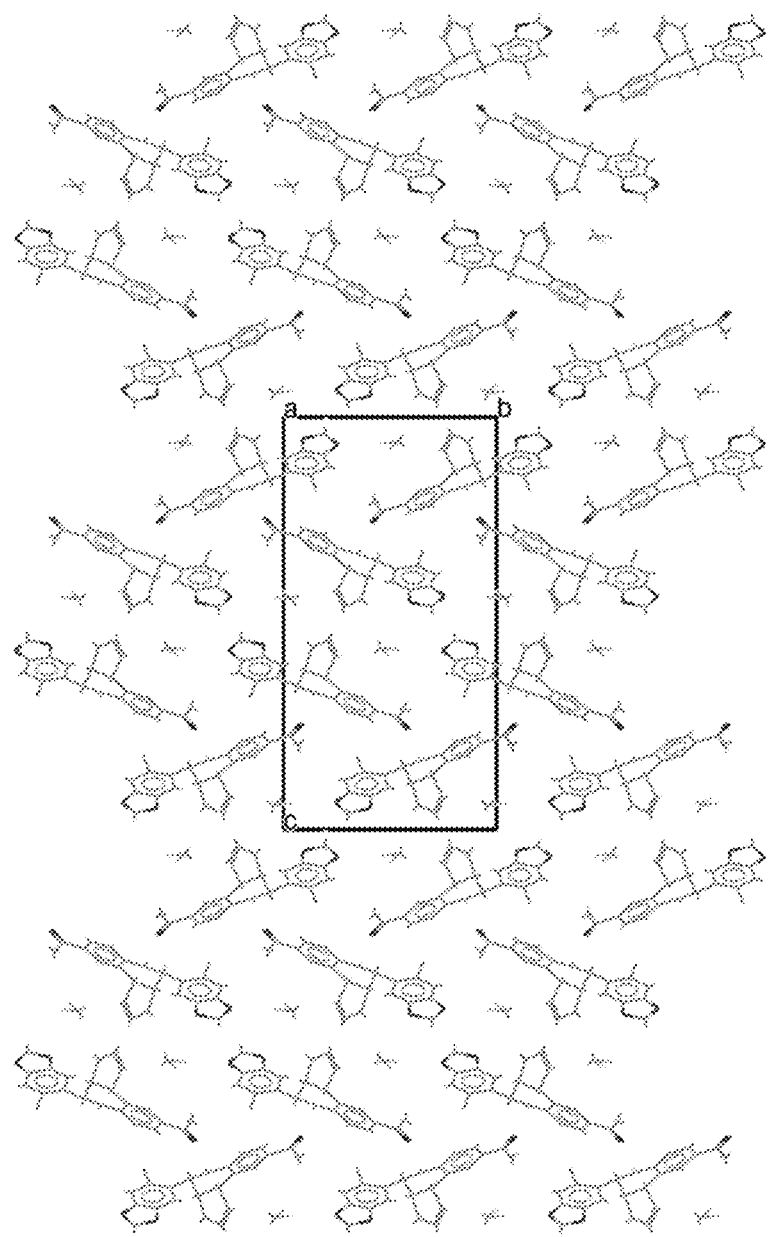
FIG. 2 shows a packing diagram viewed along the crystallographic a axis.
Figure 3:
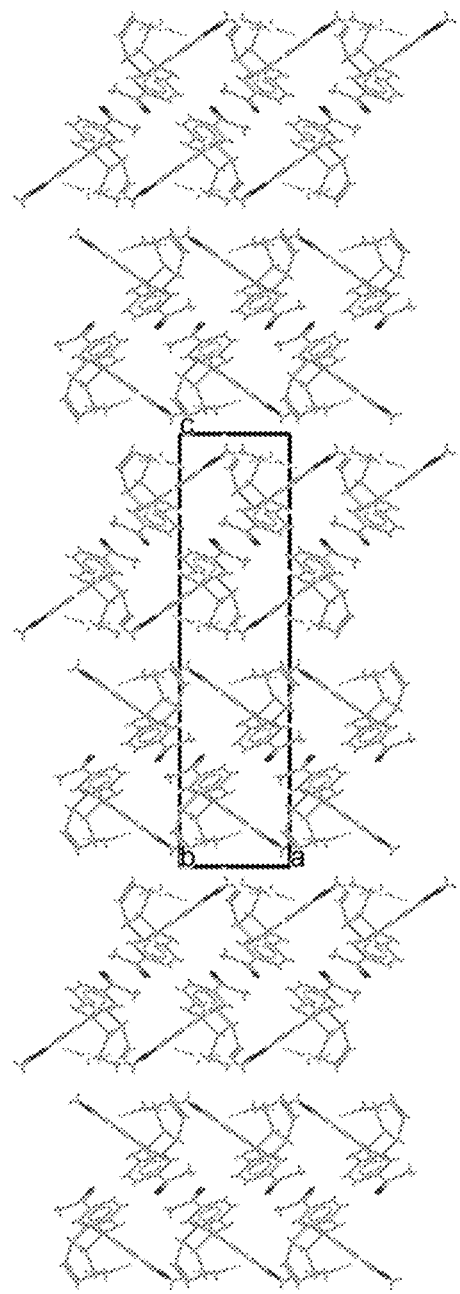
FIG. 3 shows a packing diagram viewed along the crystallographic b axis.
Figure 4:
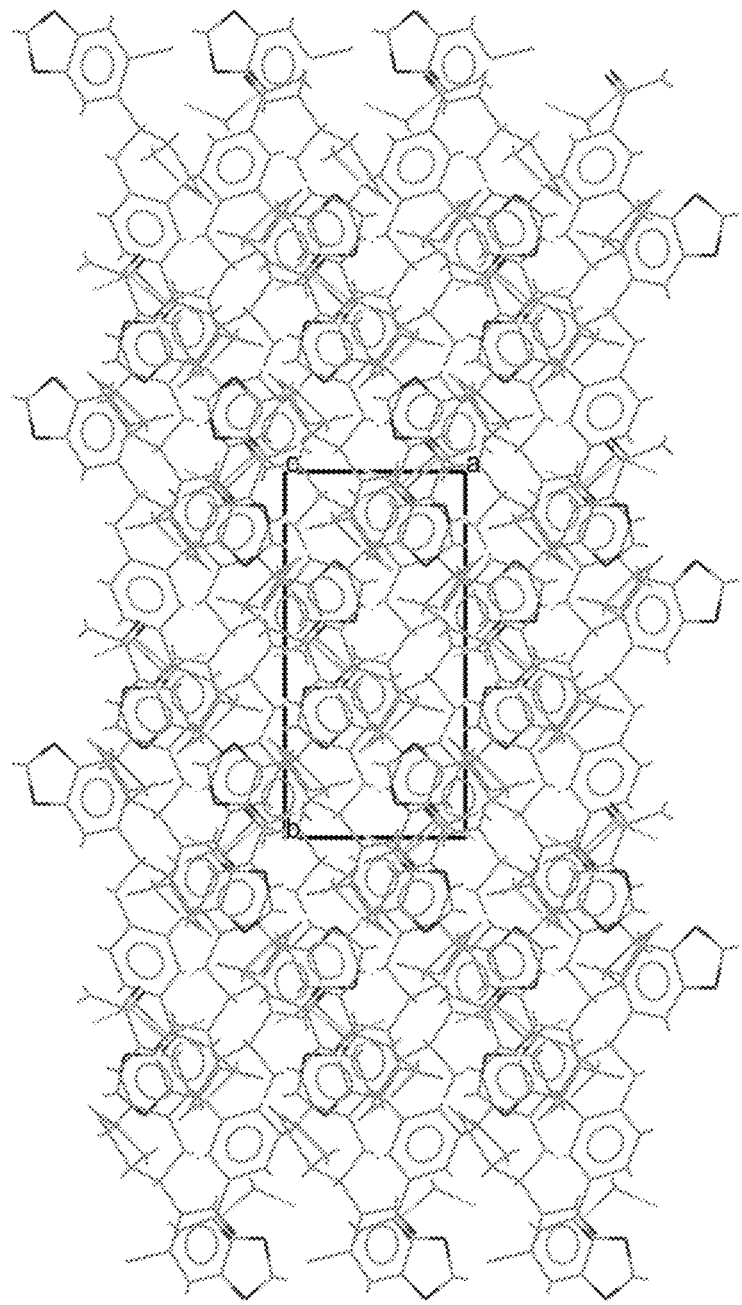
FIG. 4 shows a packing diagram viewed along the crystallographic c axis.
Figure 5:
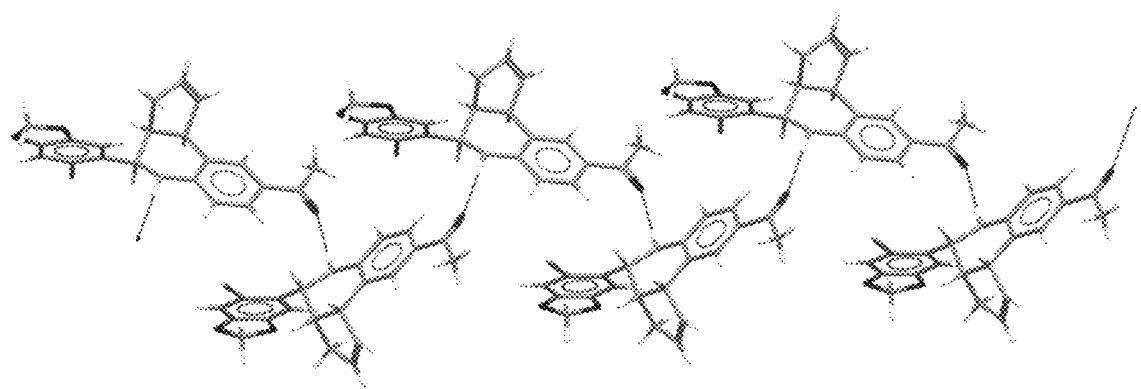
FIG. 5 shows the one-dimensional hydrogen bond network.

Packing diagrams viewed along the a, b, and c crystallographic axes are shown in FIGS. 2-4 respectively. Hydrogen bonding from the amine to the carbonyl on adjacent molecules results in a one dimensional hydrogen bond network along the b axis, shown in FIG. 5.

The absolute structure can be determined through an analysis of anomalous X-ray scattering by the crystal. Anomalous scattering is assessed through the intensity differences between Friedel pairs. For the reflection data measured up to θ$_{max}$ the Friedel coverage was 95%. A refined parameter x, known as the Flack parameter, encodes the relative abundance of the two components in an inversion twin. The structure contains a fraction 1−x of the model being refined, and x of its inverse. Provided that a low standard uncertainty is obtained, the Flack parameter should be close to 0 if the solved structure is correct, and close to 1 if the inverse model is correct. The measured Flack parameter for the structure of SSR G-1 dichloromethane solvate shown in FIG. 1 is −0.018 with a standard uncertainty of 0.013, which indicates strong inversion-distinguishing power.

Additional information regarding the absolute structure can be assessed by applying Bayesian statistics to Bijvoet differences. This analysis provides a series of probabilities for different hypotheses of the absolute structure. This analysis results in the Hooft y parameter, which is interpreted in the same fashion as the Flack x parameter. In addition, this analysis results in three probabilities that the absolute structure is either correct, incorrect or a racemic twin. For the current data set the (Flack equivalent) Hooft y parameter is −0.020(11), the probability that the structure is correct is 1.000, and the probability that the structure is either incorrect or a racemic twin are both less than 10$^{-200}$.

Figure 6:
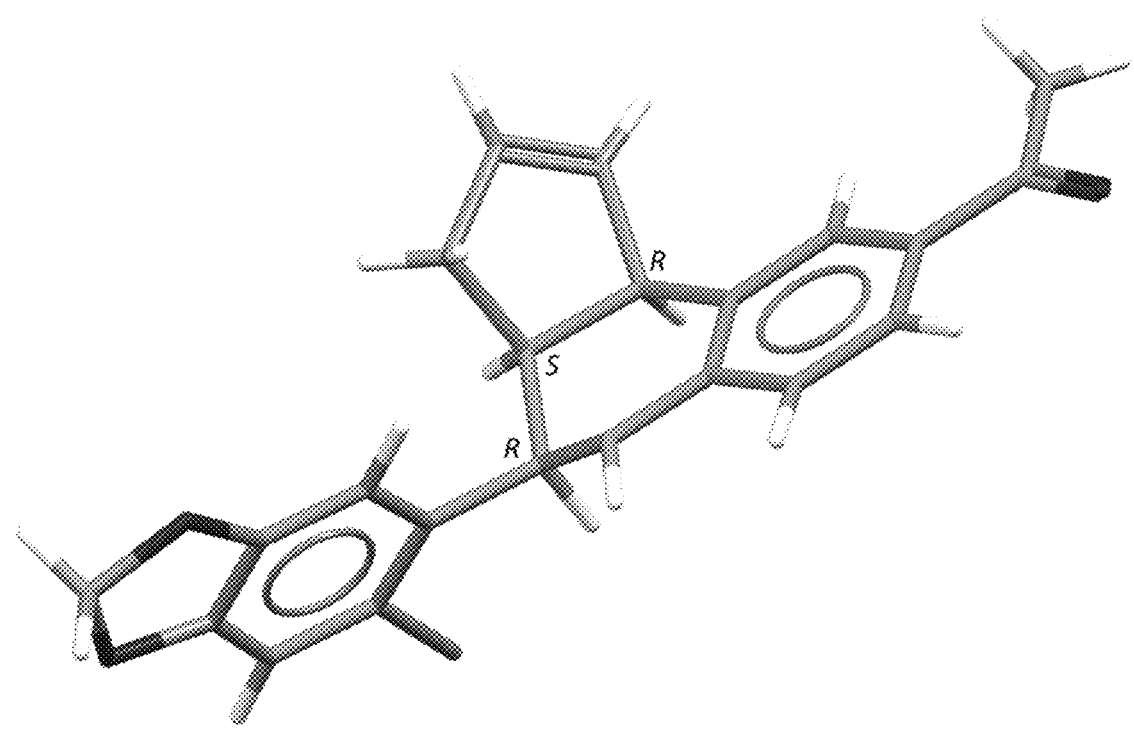
FIG. 6 show SRR G-1 with labeled chiral centers.

The absolute configuration is labeled in FIG. 6. This is consistent with the configuration of SSR G-1.

Figure 7:
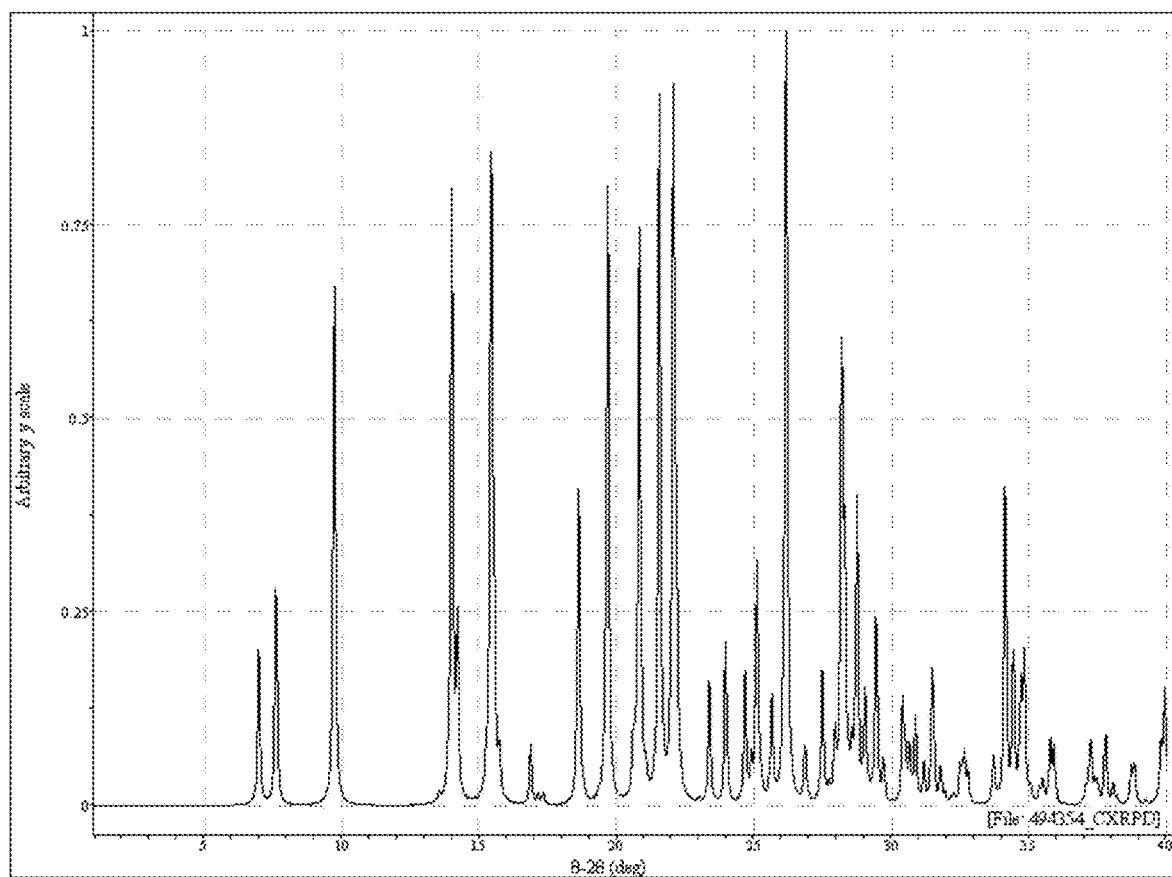
FIG. 7 shows a calculated XRPD pattern of SRR G-1 dichloromethane solvate, generated from the single crystal structure.

FIG. 7 shows a calculated XRPD pattern of SSR G-1 dichloromethane solvate, generated from the single crystal structure. The calculated XRPD pattern is identical to that assigned to bulk samples identified as displaying the Form B XRPD pattern in the polymorph screening study summarized in Table 1.

Tables of positional parameters and their estimated standard deviations, anisotropic displacement factor coefficients, bond distances, bond angles, hydrogen bonds and angles, and torsion angles are shown.

TABLE 3

Positional Parameters and Their Estimated Standard Deviations

| Atom | x | y | z | U(eq) |
|---|---|---|---|---|
| Br(1) | 8808.8(8) | 6559.3(3) | 3207.2(2) | 53.07(15) |
| Cl(2) | 3763(3) | 5448.9(16) | 5638.0(8) | 101.5(6) |
| Cl(1) | −612(3) | 5050.5(18) | 5795.3(10) | 115.1(7) |
| N(1) | 5577(5) | 3525(3) | 3323.1(13) | 42.3(7) |
| O(1) | 1123(6) | 5915(2) | 4486.3(13) | 57.7(8) |
| O(3) | 7888(6) | −878(3) | 2427.3(15) | 67.7(10) |
| O(2) | 2219(6) | 7574(3) | 4337.0(17) | 70.3(11) |
| C(14) | 8462(6) | 2312(3) | 3345.0(14) | 35.2(7) |
| C(6) | 5733(6) | 5262(3) | 3683.6(14) | 35.7(8) |
| C(5) | 6356(7) | 6265(3) | 3603.9(15) | 42.0(8) |
| C(9) | 8562(6) | 3976(3) | 3875.8(14) | 36.6(7) |
| C(13) | 9775(6) | 3030(3) | 3681.4(16) | 38.5(8) |
| C(8) | 6968(6) | 4360(3) | 3475.9(15) | 36.5(8) |
| C(15) | 6446(6) | 2602(3) | 3178.5(14) | 36.9(7) |
| C(19) | 9214(6) | 1360(3) | 3200.4(15) | 37.9(7) |
| C(7) | 3929(7) | 5085(3) | 3984.5(15) | 40.6(8) |
| C(20) | 8852(8) | −340(3) | 2729.4(15) | 45.7(8) |
| C(4) | 5279(8) | 7111(3) | 3803(2) | 49.6(10) |
| C(18) | 8068(6) | 680(3) | 2887.3(15) | 40.3(8) |
| C(17) | 6087(8) | 995(3) | 2720.5(16) | 47.6(9) |
| C(2) | 2893(6) | 5911(3) | 4185.9(17) | 42.4(9) |
| C(16) | 5301(7) | 1925(3) | 2862.0(17) | 45.9(9) |
| C(12) | 10391(8) | 2539(4) | 4200(2) | 52.3(11) |
| C(3) | 3551(8) | 6899(3) | 4097.3(18) | 49.6(10) |
| C(11) | 9271(8) | 2875(4) | 4592.1(18) | 55.4(12) |
| C(21) | 10883(8) | −717(4) | 2942(2) | 51.7(10) |
| C(1) | 702(8) | 6967(4) | 4595(2) | 64.2(14) |
| C(10) | 7705(8) | 3657(3) | 4421.2(17) | 51.9(11) |
| C(22) | 1737(10) | 4558(4) | 5593(3) | 80.0(18) |
| H(22A) | 1615 | 4330 | 5229 | 96 |
| H(22B) | 2074 | 3968 | 5809 | 96 |
| H(7) | 3510(90) | 4370(40) | 4053(19) | 56(14) |
| H(8) | 7690(60) | 4600(30) | 3131(15) | 26(9) |
| H(19) | 10640(70) | 1160(30) | 3313(17) | 42(12) |
| H(16) | 3900(100) | 2170(40) | 2756(19) | 59(14) |
| H(17) | 5370(90) | 550(40) | 2500(20) | 60(15) |
| H(4) | 5640(80) | 7770(40) | 3731(18) | 54(14) |
| H(10A) | 6310(90) | 3300(40) | 4390(20) | 59(13) |
| H(13) | 10940(80) | 3220(30) | 3471(18) | 48(12) |
| H(11) | 9270(70) | 2600(40) | 4938(19) | 46(12) |
| H(21A) | 10780(90) | −790(40) | 3310(20) | 63(16) |
| H(12) | 11490(90) | 2050(40) | 4245(19) | 59(14) |
| H(21B) | 11400(100) | 1260(40) | 2760(20) | 70(16) |
| H(10B) | 7530(90) | 4180(40) | 4680(20) | 57(14) |
| H(9) | 9630(70) | 4540(30) | 3937(16) | 40(12) |
| H(1) | 4510(80) | 3720(30) | 3112(18) | 47(13) |
| H(1A) | −980(140) | 7110(60) | 4440(30) | 130(30) |
| H(1B) | 980(110) | 7000(50) | 4990(30) | 100(20) |
| H(21C) | 12080(110) | −240(50) | 2910(30) | 90(20) |

Hydrogen atoms were refined isotropically except H22A&B, which were included in calculation of structure factors but not refined

TABLE 4

Anisotropic Displacement Factor Coefficients

| Atom | $U_{11}$ | $U_{22}$ | $U_{33}$ | $U_{23}$ | $U_{13}$ | $U_{12}$ |
|---|---|---|---|---|---|---|
| Br(1) | 49.9(2) | 50.7(2) | 58.7(2) | 10.2(2) | 5.2(2) | −10.2(2) |
| Cl(2) | 85.3(10) | 111.4(13) | 107.8(13) | 19.4(10) | −34.4(11) | −23.5(11) |
| Cl(1) | 93.0(14) | 107.4(15) | 144.8(18) | −22.8(14) | 21.2(13) | 1.5(11) |
| N(1) | 35.1(16) | 42.2(17) | 49.7(18) | −8.6(15) | −9.2(13) | 1.1(13) |
| O(1) | 44.1(15) | 61.5(18) | 67.4(19) | −18.9(15) | 14.3(17) | −3.6(16) |
| O(3) | 73(2) | 54.4(19) | 76(2) | −28.4(18) | −17.7(19) | 3.1(17) |
| O(2) | 59(2) | 50.7(19) | 102(3) | −27.2(19) | 10(2) | 6.8(16) |
| C(14) | 33.6(18) | 34.7(16) | 37.2(17) | 0.1(13) | −0.9(14) | −5.6(14) |
| C(6) | 35.4(19) | 37.4(18) | 34.2(16) | −0.8(14) | −3.4(14) | −1.5(14) |
| C(5) | 39.8(19) | 40.6(19) | 45.6(18) | 2.9(14) | −3.7(18) | −2.3(16) |
| C(9) | 34.4(18) | 36.2(17) | 39.4(17) | −2.7(14) | −2.7(16) | −3.3(15) |
| C(13) | 32.3(18) | 38.2(19) | 45(2) | −4.7(16) | −4.3(16) | −3.8(15) |
| C(8) | 36.5(19) | 35.0(18) | 38.0(18) | −0.1(15) | −2.9(15) | −0.7(14) |
| C(15) | 34.8(17) | 38.7(17) | 37.1(16) | 0.0(14) | −0.4(17) | −1.7(14) |
| C(19) | 36.7(19) | 38.9(18) | 38.2(16) | −1.3(15) | 0.7(15) | −1.4(13) |
| C(7) | 37.3(19) | 39.1(19) | 45.5(19) | −2.9(15) | 0.8(18) | −2.3(17) |
| C(20) | 53(2) | 41.3(19) | 42.6(19) | −6.0(15) | 2(2) | −9(2) |
| C(4) | 52(2) | 31(2) | 65(3) | −0.4(19) | −4(2) | −3.5(17) |
| C(18) | 43(2) | 41(2) | 37.2(18) | −5.5(15) | −0.6(16) | −7.2(15) |
| C(17) | 44(2) | 51(2) | 48(2) | −14.4(17) | −6(2) | −6(2) |
| C(2) | 35.5(19) | 45(2) | 47(2) | −9.1(17) | 0.6(17) | −0.1(16) |
| C(16) | 40(2) | 51(2) | 47(2) | −13.0(18) | −10.0(18) | 0.9(17) |
| C(12) | 50(2) | 46(2) | 61(3) | −7(2) | −26(2) | 2.7(19) |
| C(3) | 47(2) | 44(2) | 58(2) | −13.6(18) | −5(2) | 5.8(18) |
| C(11) | 68(3) | 55(3) | 43(2) | 1.7(19) | −17(2) | 3(2) |
| C(21) | 54(3) | 45(2) | 57(3) | −10.2(19) | 0(2) | 4.0(19) |
| C(1) | 50(3) | 71(3) | 72(3) | −28(3) | 5(2) | 11(2) |
| C(10) | 60(3) | 60(3) | 35.4(19) | 1.5(19) | −4.8(19) | 7(2) |
| C(22) | 86(4) | 52(3) | 103(4) | −11(3) | −27(4) | 10(3) |

The form of the anisotropic temperature factor is:
$$\exp[-2\pi^2(h^2 a^{*2} U(1,1) + k^2 b^{*2} U(2,2) + l^2 c^{*2} U(3,3) + 2hka^*b^* U(1,2) + 2hla^*c^* U(1,3) + 2klb^*c^* U(2,3))]$$
where $a^*$, $b^*$, and $c^*$ are reciprocal lattice constants.

The form of the anisotropic temperature factor is:
$\exp[-2\pi^2 h^2 a^{*2} U(1,1) + k^2 b^{*2} U(2,2) + l^2 c^{*2} U(3,3) + 2hka^*b^*U(1,2) + 2hla^*c^*U(1,3) + 2klb^*c^*U(2,3)]$ where $a^*$, $b^*$, and $c^*$ are reciprocal lattice constants.

TABLE 5

Bond Distances in Ångströms

| Atom | Atom | Length/Å |
|---|---|---|
| Br(1) | C(5) | 1.909(4) |
| C(5) | C(4) | 1.399(6) |
| Cl(2) | C(22) | 1.751(6) |
| C(9) | C(13) | 1.543(5) |
| Cl(1) | C(22) | 1.720(7) |
| C(9) | C(8) | 1.525(5) |
| N(1) | C(8) | 1.463(5) |
| C(9) | C(10) | 1.543(6) |
| N(1) | C(15) | 1.380(5) |
| C(13) | C(12) | 1.514(6) |
| O(1) | C(2) | 1.369(5) |
| C(15) | C(16) | 1.402(5) |
| O(1) | C(1) | 1.430(6) |
| C(19) | C(18) | 1.400(5) |
| O(3) | C(20) | 1.209(5) |
| C(7) | C(2) | 1.367(6) |
| O(2) | C(3) | 1.371(5) |
| C(20) | C(18) | 1.481(6) |
| O(2) | C(1) | 1.417(7) |
| C(20) | C(21) | 1.495(7) |
| C(14) | C(13) | 1.523(5) |
| C(4) | C(3) | 1.366(7) |
| C(14) | C(15) | 1.415(5) |
| C(18) | C(17) | 1.404(7) |
| C(14) | C(19) | 1.385(5) |
| C(17) | C(16) | 1.365(6) |
| C(6) | C(5) | 1.385(5) |
| C(2) | C(3) | 1.378(6) |
| C(6) | C(8) | 1.516(5) |
| C(12) | C(11) | 1.302(7) |
| C(6) | C(7) | 1.407(6) |
| C(11) | C(10) | 1.499(7) |

Numbers in parentheses are estimated standard deviations in the least significant digits.

TABLE 6

Bond Angles in Degrees

| Atom | Atom | Atom | Angle/° |
|---|---|---|---|
| C(15) | N(1) | C(8) | 118.4(3) |
| C(16) | C(15) | C(14) | 118.8(3) |
| C(2) | O(1) | C(1) | 105.6(4) |
| C(14) | C(19) | C(18) | 122.4(4) |
| C(3) | O(2) | C(1) | 105.9(4) |
| C(2) | C(7) | C(6) | 118.3(4) |
| C(15) | C(14) | C(13) | 120.6(3) |
| O(3) | C(20) | C(18) | 121.3(4) |
| C(19) | C(14) | C(13) | 120.6(3) |
| O(3) | C(20) | C(21) | 118.9(4) |
| C(19) | C(14) | C(15) | 118.8(3) |
| C(18) | C(20) | C(21) | 119.8(4) |
| C(5) | C(6) | C(8) | 122.3(4) |
| C(3) | C(4) | C(5) | 116.0(4) |
| C(5) | C(6) | C(7) | 118.2(4) |
| C(19) | C(18) | C(20) | 123.0(4) |
| C(7) | C(6) | C(8) | 119.4(3) |
| C(19) | C(18) | C(17) | 117.5(4) |
| C(6) | C(5) | Br(1) | 120.4(3) |
| C(17) | C(18) | C(20) | 119.5(4) |
| C(6) | C(5) | C(4) | 123.6(4) |
| C(16) | C(17) | C(18) | 121.3(4) |
| C(4) | C(5) | Br(1) | 116.0(3) |
| O(1) | C(2) | C(3) | 110.0(4) |
| C(8) | C(9) | C(13) | 113.1(3) |
| C(7) | C(2) | O(1) | 128.0(4) |
| C(8) | C(9) | C(10) | 116.2(4) |

TABLE 6-continued

Bond Angles in Degrees

| Atom | Atom | Atom | Angle/° |
|---|---|---|---|
| C(7) | C(2) | C(3) | 122.0(4) |
| C(10) | C(9) | C(13) | 104.4(3) |
| C(17) | C(16) | C(15) | 121.1(4) |
| C(14) | C(13) | C(9) | 113.1(3) |
| C(11) | C(12) | C(13) | 111.8(4) |
| C(12) | C(13) | C(14) | 111.6(3) |
| O(2) | C(3) | C(2) | 109.8(4) |
| C(12) | C(13) | C(9) | 101.3(3) |
| C(4) | C(3) | O(2) | 128.2(4) |
| N(1) | C(8) | C(6) | 110.6(3) |
| C(4) | C(3) | C(2) | 121.9(4) |
| N(1) | C(8) | C(9) | 109.9(3) |
| C(12) | C(11) | C(10) | 112.5(4) |
| C(6) | C(8) | C(9) | 112.2(3) |
| O(2) | C(1) | O(1) | 108.6(4) |
| N(1) | C(15) | C(14) | 121.8(3) |
| C(11) | C(10) | C(9) | 101.7(4) |
| N(1) | C(15) | C(16) | 119.4(3) |
| Cl(1) | C(22) | Cl(2) | 112.7(3) |

Numbers in parentheses are estimated standard deviations in the least significant digits.

TABLE 7

Hydrogen Bond Distances in Ångströms and Angles in Degrees

| Donor | H | Acceptor | D-H | H...A | D...A | D-H...A |
|---|---|---|---|---|---|---|
| N(1) | H(1) | O(3) | 0.91 (5) | 2.13(5) | 3.030(5) | 176(4) |

Numbers in parentheses are estimated standard deviations in the least significant digits.

TABLE 8

Torsion Angles in Degrees

| A | B | C | D | Angle/° |
|---|---|---|---|---|
| Br(1) | C(5) | C(4) | C(3) | −178.5(3) |
| C(8) | C(9) | C(10) | C(11) | 152.3(4) |
| N(1) | C(15) | C(16) | C(17) | −178.5(4) |
| C(15) | N(1) | C(8) | C(6) | −173.2(3) |
| O(1) | C(2) | C(3) | O(2) | −0.2(5) |
| C(15) | N(1) | C(8) | C(9) | −48.7(5) |
| O(1) | C(2) | C(3) | C(4) | −179.4(4) |
| C(15) | C(14) | C(13) | C(9) | 8.6(5) |
| O(3) | C(20) | C(18) | C(19) | −174.5(4) |
| C(15) | C(14) | C(13) | C(12) | 122.0(4) |
| O(3) | C(20) | C(18) | C(17) | 5.6(6) |
| C(15) | C(14) | C(19) | C(18) | 1.2(6) |
| C(14) | C(13) | C(12) | C(11) | −102.7(5) |
| C(19) | C(14) | C(13) | C(9) | −170.9(3) |
| C(14) | C(15) | C(16) | C(17) | 0.9(6) |
| C(19) | C(14) | C(13) | C(12) | −57.5(5) |
| C(14) | C(19) | C(18) | C(20) | 180.0(4) |
| C(19) | C(14) | C(15) | N(1) | 177.9(3) |
| C(14) | C(19) | C(18) | C(17) | −0.2(6) |
| C(19) | C(14) | C(15) | C(16) | −1.6(5) |
| C(6) | C(5) | C(4) | C(3) | 1.2(7) |
| C(19) | C(18) | C(17) | C(16) | −0.5(6) |
| C(6) | C(7) | C(2) | O(1) | 180.0(4) |
| C(6) | C(5) | C(6) | Br(1) | 179.2(3) |
| C(6) | C(7) | C(2) | C(3) | 0.8(6) |
| C(7) | C(6) | C(5) | C(4) | −0.5(6) |
| C(5) | C(6) | C(8) | N(1) | −146.0(4) |
| C(7) | C(6) | C(8) | N(1) | 36.3(5) |
| C(5) | C(6) | C(8) | C(9) | 90.8(4) |
| C(7) | C(6) | C(8) | C(9) | −86.8(4) |
| C(5) | C(6) | C(7) | C(2) | −0.5(6) |
| C(7) | C(2) | C(3) | O(2) | 179.1(4) |
| C(5) | C(4) | C(3) | O(2) | −179.9(5) |
| C(7) | C(2) | C(3) | C(4) | 0.0(7) |
| C(5) | C(4) | C(3) | C(2) | −0.9(7) |

TABLE 8-continued

Torsion Angles in Degrees

| A | B | C | D | Angle/° |
|---|---|---|---|---|
| C(20) | C(18) | C(17) | C(16) | 179.3(4) |
| C(9) | C(13) | C(12) | C(11) | 17.9(5) |
| C(18) | C(17) | C(16) | C(15) | 0.1(7) |
| C(13) | C(14) | C(15) | N(1) | −1.6(5) |
| C(2) | O(1) | C(1) | O(2) | 2.1(6) |
| C(13) | C(14) | C(15) | C(16) | 179.0(4) |
| C(12) | C(11) | C(10) | C(9) | −17.1(6) |
| C(13) | C(14) | C(19) | C(18) | −179.3(4) |
| C(3) | O(2) | C(1) | O(1) | −2.2(6) |
| C(13) | C(9) | C(8) | N(1) | 54.2(4) |
| C(21) | C(20) | C(18) | C(19) | 4.9(6) |
| C(13) | C(9) | C(8) | C(6) | 177.7(3) |
| C(21) | C(20) | C(18) | C(17) | −174.9(4) |
| C(13) | C(9) | C(10) | C(11) | 27.0(4) |
| C(1) | O(1) | C(2) | C(7) | 179.5(5) |
| C(13) | C(12) | C(11) | C(10) | −0.5(6) |
| C(1) | O(1) | C(2) | C(3) | −1.2(5) |
| C(8) | N(1) | C(15) | C(14) | 22.9(5) |
| C(1) | O(2) | C(3) | C(4) | −179.4(5) |
| C(8) | N(1) | C(15) | C(16) | −157.7(4) |
| C(1) | O(2) | C(3) | C(2) | 1.5(6) |
| C(8) | C(6) | C(5) | Br(1) | 1.5(5) |
| C(10) | C(9) | C(13) | C(14) | 92.4(4) |
| C(8) | C(6) | C(5) | C(4) | −178.2(4) |
| C(10) | C(9) | C(13) | C(12) | −27.1(4) |
| C(8) | C(6) | C(7) | C(2) | 177.3(4) |
| C(10) | C(9) | C(8) | N(1) | −66.7(4) |
| C(8) | C(9) | C(13) | C(14) | −34.9(4) |
| C(10) | C(9) | C(8) | C(6) | 56.9(5) |
| C(8) | C(9) | C(13) | C(12) | −154.4(3) |

Numbers in parentheses are estimated standard deviations in the least significant digits.

Starting with SRR G-1 prepared according to Example 1, a suitable single crystal of the Form A crystal form was grown from isopropanol solution and analyzed by single-crystal X-ray diffractometry. The structure was determined successfully. A single crystal x-ray analysis was conducted on a colorless plate having approximate dimensions of 0.203×0.137×0.033 mm³, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector. Cell constants and an orientation matrix for data collection were obtained from least-squares refinement using the setting angles of 9009 reflections in the range 4.7640°<θ<77.3860°. The space group was determined by the program CRYSALISPRO to be $P2_12_12_1$. The data were collected to a maximum diffraction angle (2θ) of 155.264° at room temperature.

Frames were integrated with CRYSALISPRO. A total of 17299 reflections were collected, of which 7561 were unique. Lorentz and polarization corrections were applied to the data. The linear absorption coefficient is 3.206 mm⁻¹ for Cu Kα radiation. An empirical absorption correction using CRYSALISPRO was applied. Transmission coefficients ranged from 0.733 to 1.000. Intensities of equivalent reflections were averaged. The agreement factor for the averaging was 2.74% based on intensity.

The structure was solved by direct methods using $S_{HELXT}$. The remaining atoms were located in succeeding difference Fourier syntheses. The structure was refined using $S_{HELXL}$-2014. Hydrogen atoms were refined independently. The structure was refined in full-matrix least-squares by minimizing the function:

$$\Sigma w(|F_o|^2 - |F_c|^2)^2$$

where the weight, w, is defined as $1/[\sigma^2(F_o^2)+(0.0401\ P)^2+(0.3205\ P)]$, where $P=(F_o^2+2F_c^2)/3$. Scattering factors were taken from the "International Tables for Crystallography". Of the 7561 reflections used in the refinements, only the reflections with intensities larger than twice their uncertainty [I>2σ(I)], 6752, were used in calculating the fit residual, R. The final cycle of refinement included 613 variable parameters, 0 restraints, and converged with respective unweighted and weighted agreement factors of:

$$R = \Sigma|F_o - F_c|/\Sigma F_o = 0.0325$$

$$R_w = \sqrt{(\Sigma_w(F_o^2 - F_c^2)^2 / \Sigma w(F_o^2)^2)} = 0.0813$$

The standard deviation of an observation of unit weight (goodness of fit) was 1.04. The highest peak in the final difference Fourier had an electron density of 0.319 e/Å³. The minimum negative peak had a value of −0.454 e/Å³.

Figure 8:
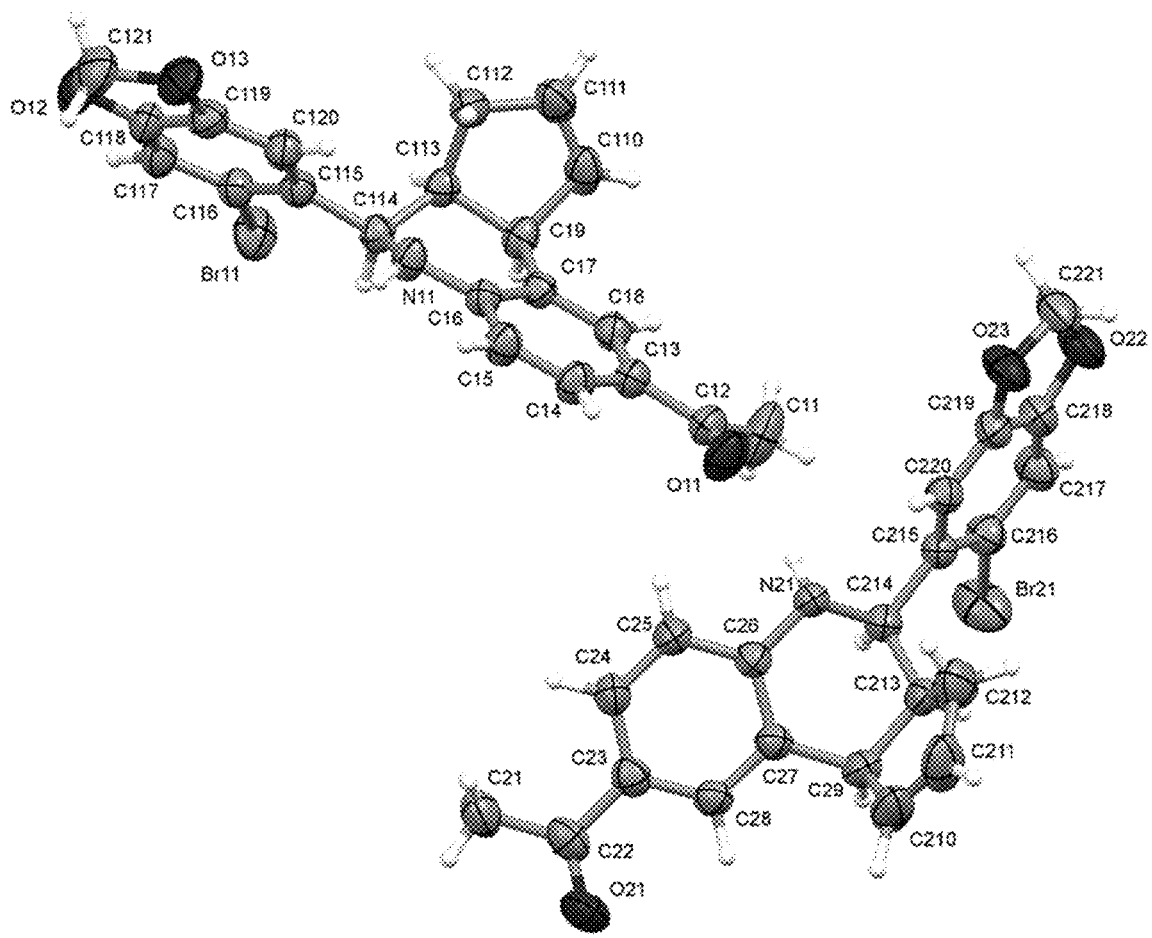
FIG. 8 shows the Atomic displacement ellipsoid diagram of SRR G-1 Form A.
Figure 9:
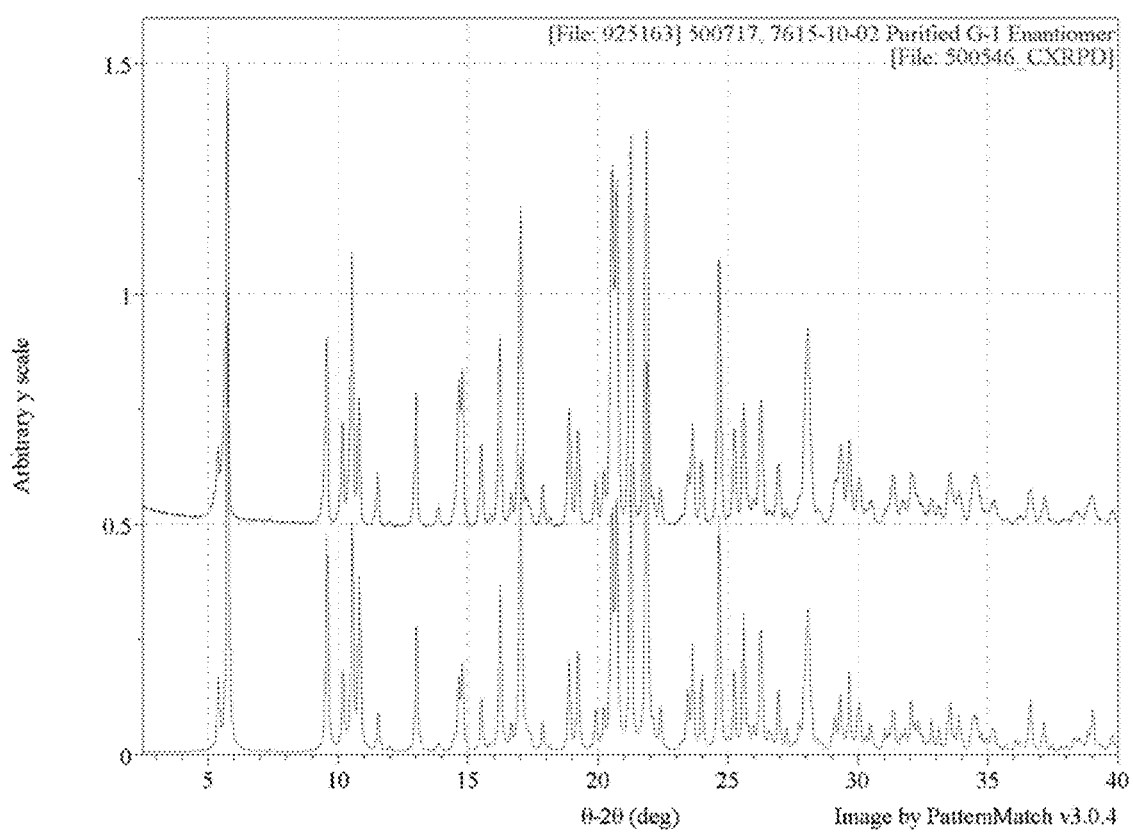
FIG. 9 shows the Calculated and experimental XRPD patterns for SRR G-1 Form A.

The crystal system is orthorhombic and the space group is $P2_12_12_1$. The cell parameters and calculated volume are: a=6.50106(9) Å, b=17.3547(2) Å, c=32.6957(4) Å, α=90°, β=90°, γ=90°, V=3688.85(9) Å³. The molecular weight is 412.27 g mol⁻¹ with Z=8, resulting in a calculated density of 1.485 g cm⁻³. Further details of the crystal data and crystallographic data collection parameters are summarized in Table 9. An atomic displacement ellipsoid drawing of Form A is shown in FIG. 8. The asymmetric unit shown contains two enantiopure SRR G-1 molecules. From the structure, the absolute configuration was determined conclusively. SRR G-1 contains three chiral centers located at C114 (C214), C113 (C213), and C19 (C29) which bond in the R, S, and R configuration, respectively. A calculated XRPD pattern of Form A, generated from the single crystal structure, is provided in FIG. 9 and compared to the experimental pattern.

TABLE 9

Crystal Data and Data Collection Parameters SRR G-1 (Form A)

| | |
|---|---|
| Empirical formula | $C_{21}H_{18}BrNO_3$ |
| Formula weight (g mol⁻¹) | 412.27 |
| Temperature (K) | 299.84(10) |
| Wavelength (Å) | 1.54184 |
| Crystal system | orthorhombic |
| Space group | $P2_12_12_1$ |
| Unit cell parameters | |
| a = 6.50106(9) Å | α = 90° |
| b = 17.3547(2) Å | β = 90° |
| c = 32.6957(4) Å | γ = 90° |
| Unit cell volume (Å³) | 3688.85(9) |
| Cell formula units, Z | 8 |
| Calculated density (g cm⁻³) | 1.485 |
| Absorption coefficient (mm⁻¹) | 3.206 |
| F(000) | 1680 |
| Crystal size (mm³) | 0.203 × 0.137 × 0.033 |
| Reflections used for cell measurement | 9009 |
| θ range for cell measurement | 4.7640°–77.3860° |
| Total reflections collected | 17299 |
| Index ranges | −8 ≤ h ≤ 7; −21 ≤ k ≤ 10; −40 ≤ l ≤ 38 |
| θ range for data collection | $\theta_{min}$ = 3.714°, $\theta_{max}$ = 77.632° |
| Completeness to $\theta_{max}$ | 98.3% |
| Completeness to $\theta_{full}$ = 67.684° | 99.9% |
| Absorption correction | multi-scan |
| Transmission coefficient range | 0.733–1.000 |
| Refinement method | full matrix least-squares on F² |
| Independent reflections | 7561 [$R_{int}$ = 0.0274, $R_\sigma$ = 0.0337] |
| Reflections [1 > 2σ(I)] | 6752 |
| Reflections/restraints/parameters | 7561/0/613 |
| Goodness-of-fit on F² | S = 1.04 |
| Final residuals [1 > 2σ(I)] | R = 0.0325, $R_w$ = 0.0813 |

TABLE 9-continued

| Crystal Data and Data Collection Parameters SRR G-1 (Form A) | |
|---|---|
| Final residuals [all reflections] | R = 0.0373, $R_w$ = 0.0843 |
| Largest diff. peak and hole (e Å$^{-3}$) | 0.319, −0.454 |
| Max/mean shift/standard uncertainty | 0.002/0.000 |
| Absolute structure determination | Flack parameter: −0.015(9) |

Example 3: Form and Polymorph Data

SRR G-1 forms two distinctive polymorphs, Forms A and C; a solvate, Form B; as well as amorphous material. The XRPD patterns for the crystalline forms are compared in FIG. 10. Form B is a mono DCM solvate that desolvates to Form C upon exposure to elevated temperatures between 100 and 120° C. Form C, the desolvate, exhibits a melt onset near 129° C. Form A is the thermodynamically stable form at all temperatures (monotropically related to Form C) and exhibits a melt onset near 178° C. Amorphous material is not physically stable and crystallizes to Form A upon exposure to either elevated temperature or humidity. The forms are discussed in more detail in subsequent sections below.

Crystalline Form A

Form A is anhydrous with a melt onset near 178° C. Form A is thermodynamically the most stable form, relative, monotropically, to Form C. Form A was routinely obtained from multiple crystallization techniques utilizing various organic solvents and organic/water solvent systems other than dichloromethane.

The observed XRPD peaks for Crystalline Form A are listed in Table 10

TABLE 10

| Diffraction angle 2θ (°) | d-spacing (Å) | Intensity (%) |
|---|---|---|
| 5.39 ± 0.20 | 16.387 ± 0.608 | 19 |
| 5.75 ± 0.20 | 15.364 ± 0.534 | 100 |
| 9.56 ± 0.20 | 9.245 ± 0.193 | 43 |
| 10.17 ± 0.20 | 8.689 ± 0.170 | 25 |
| 10.53 ± 0.20 | 8.397 ± 0.159 | 60 |
| 10.81 ± 0.20 | 8.181 ± 0.151 | 30 |
| 11.52 ± 0.20 | 7.675 ± 0.133 | 14 |
| 11.95 ± 0.20 | 7.400 ± 0.123 | 4 |
| 13.02 ± 0.20 | 6.795 ± 0.104 | 31 |
| 13.88 ± 0.20 | 6.377 ± 0.091 | 7 |
| 14.66 ± 0.20 | 6.036 ± 0.082 | 34 |
| 14.79 ± 0.20 | 5.985 ± 0.080 | 36 |
| 15.52 ± 0.20 | 5.705 ± 0.073 | 20 |
| 15.87 ± 0.20 | 5.578 ± 0.070 | 5 |
| 16.23 ± 0.20 | 5.457 ± 0.067 | 43 |
| 16.67 ± 0.20 | 5.315 ± 0.063 | 10 |
| 17.03 ± 0.20 | 5.204 ± 0.061 | 70 |
| 17.23 ± 0.20 | 5.142 ± 0.059 | 9 |
| 17.88 ± 0.20 | 4.958 ± 0.055 | 11 |
| 18.16 ± 0.20 | 4.882 ± 0.053 | 5 |
| 18.89 ± 0.20 | 4.695 ± 0.049 | 28 |
| 19.22 ± 0.20 | 4.614 ± 0.048 | 23 |
| 19.91 ± 0.20 | 4.456 ± 0.044 | 12 |
| 20.22 ± 0.20 | 4.389 ± 0.043 | 15 |
| 20.54 ± 0.20 | 4.321 ± 0.042 | 80 |
| 20.71 ± 0.20 | 4.285 ± 0.041 | 76 |
| 21.25 ± 0.20 | 4.178 ± 0.039 | 86 |
| 21.86 ± 0.20 | 4.062 ± 0.037 | 88 |
| 22.10 ± 0.20 | 4.019 ± 0.036 | 9 |
| 22.39 ± 0.20 | 3.968 ± 0.035 | 11 |
| 23.44 ± 0.20 | 3.793 ± 0.032 | 14 |
| 23.62 ± 0.20 | 3.763 ± 0.031 | 24 |
| 23.99 ± 0.20 | 3.706 ± 0.030 | 17 |
| 24.67 ± 0.20 | 3.606 ± 0.029 | 60 |
| 25.25 ± 0.20 | 3.524 ± 0.027 | 23 |

TABLE 10-continued

| Diffraction angle 2θ (°) | d-spacing (Å) | Intensity (%) |
|---|---|---|
| 25.61 ± 0.20 | 3.475 ± 0.027 | 28 |
| 25.99 ± 0.20 | 3.425 ± 0.026 | 9 |
| 26.27 ± 0.20 | 3.390 ± 0.025 | 30 |
| 26.94 ± 0.20 | 3.307 ± 0.024 | 16 |
| 27.24 ± 0.20 | 3.271 ± 0.024 | 6 |
| 28.06 ± 0.20 | 3.177 ± 0.022 | 44 |
| 29.13 ± 0.20 | 3.063 ± 0.021 | 13 |
| 29.33 ± 0.20 | 3.042 ± 0.020 | 20 |
| 29.66 ± 0.20 | 3.009 ± 0.020 | 21 |
| 30.04 ± 0.20 | 2.972 ± 0.019 | 13 |

Figure 11A:
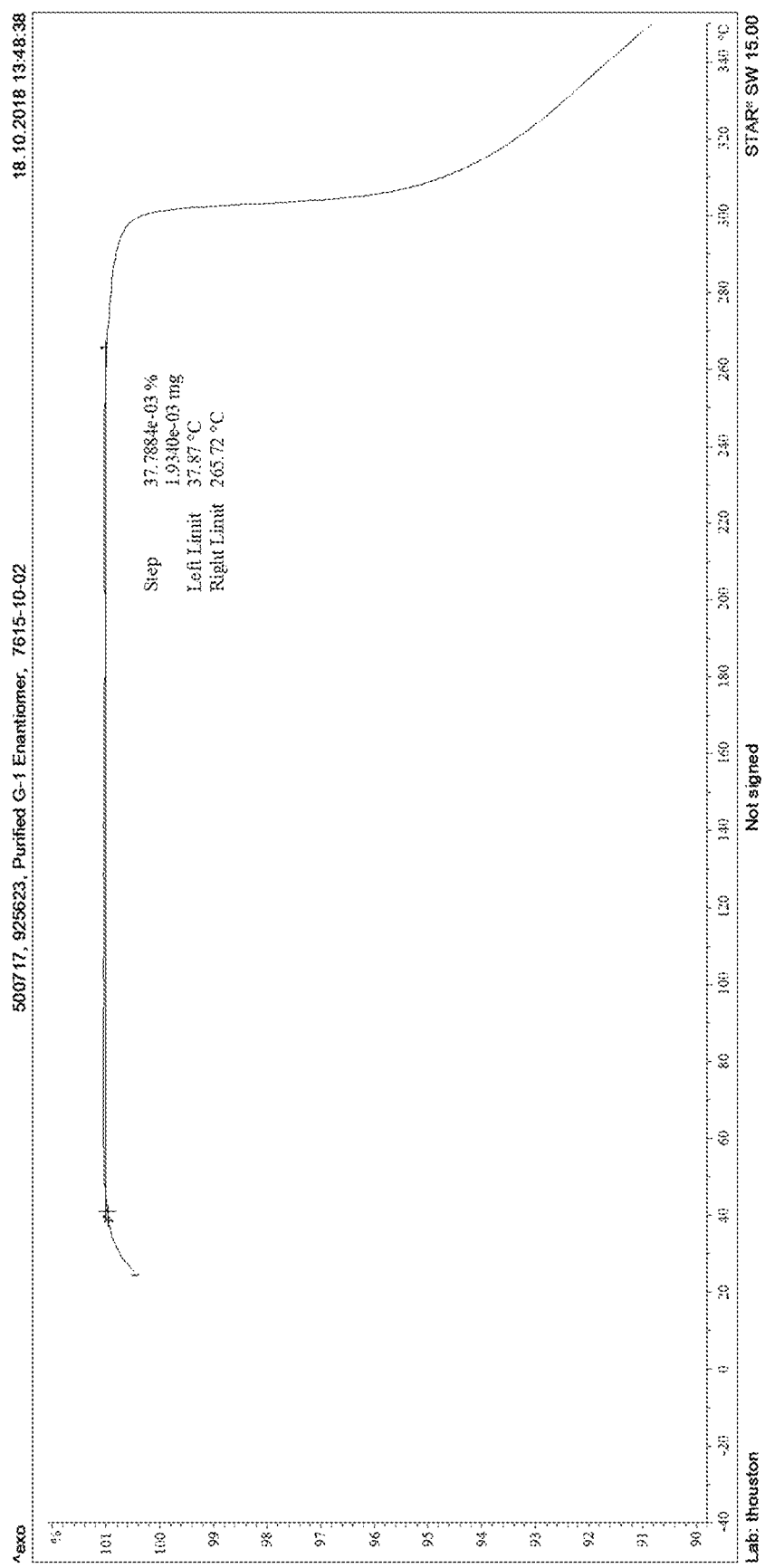
FIGS. 11A and 11B show the Thermograms for SRR G-1 Form A.
Figure 11B:
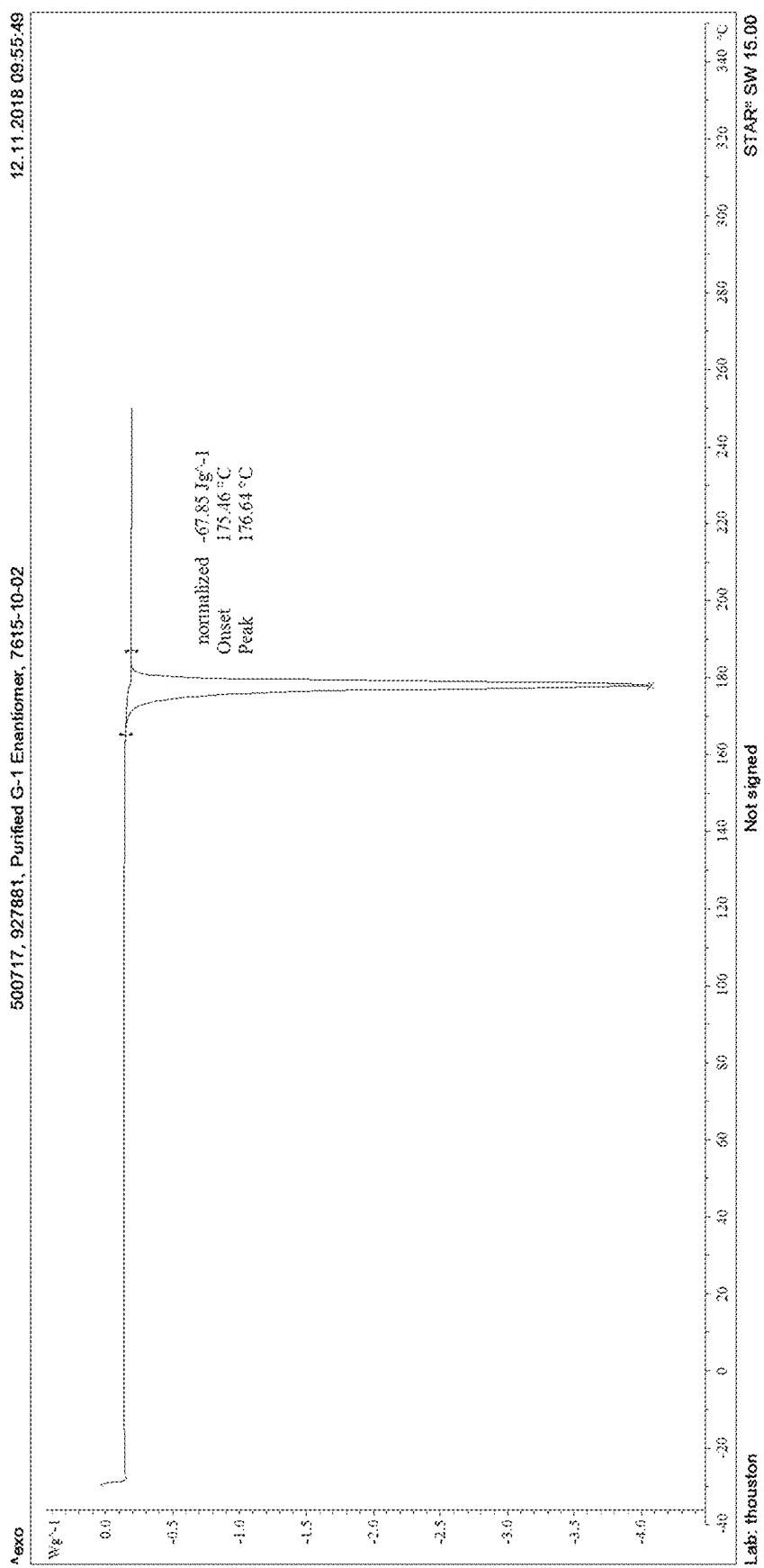

Thermograms of Form A are shown in FIGS. 11A and 11B. Thermogravimetric Analysis (TGA) data shows no weight loss up to 266° C., consistent with an anhydrous form. The DSC exhibits a single endotherm with an onset near 176° C. (68 J/g). The event was visually confirmed on a hot plate as a melt. Discoloration, likely due to decomposition, was noted upon melting.

Figure 12:
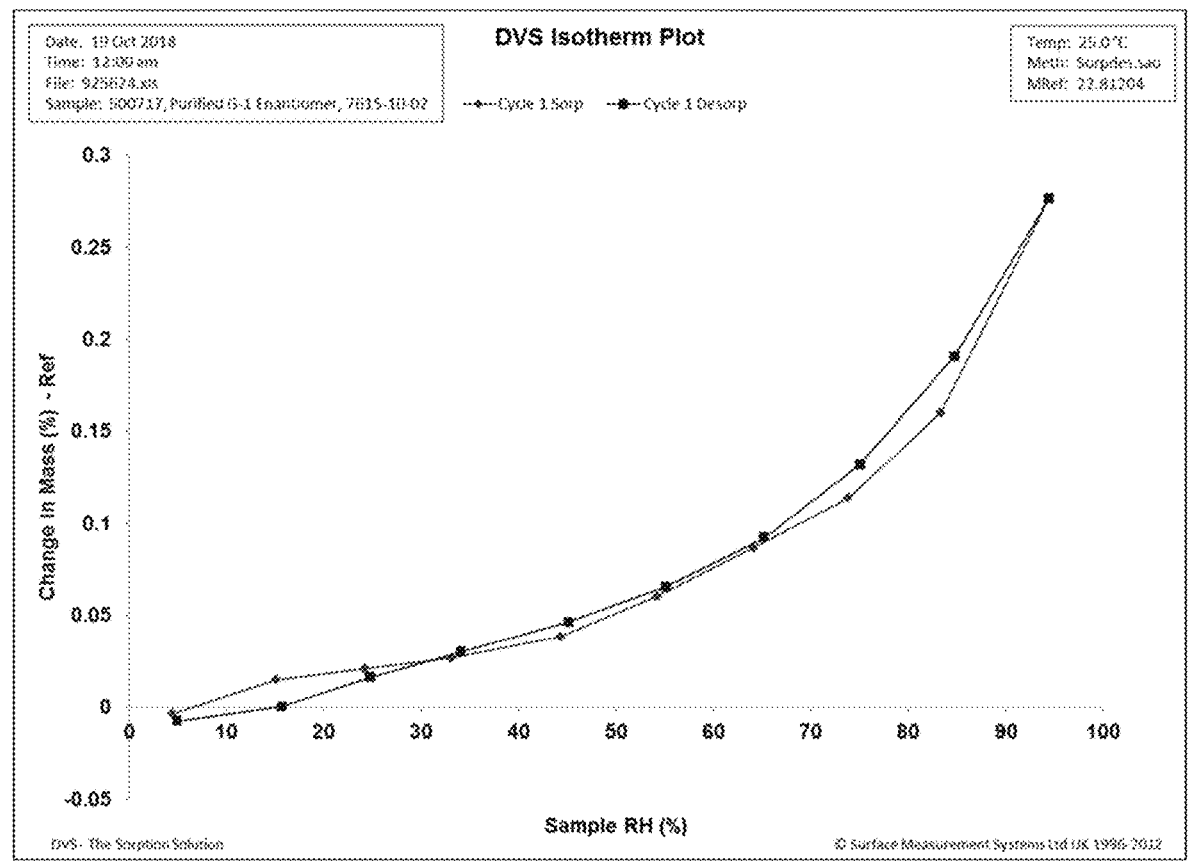
FIG. 12 shows the DVS isotherm for SRR G-1 Form A.

The Dynamic Vapor Sorption isotherm for Form A indicates the form exhibits low hygroscopicity (FIG. 12). The weight change through the sorption/desorption cycle was less than 0.3% weight. Hysteresis was not observed. The material recovered from the Dynamic Vapor Sorption experiment was Form A by XRPD.

Crystalline Form B

Form B is monodichloromethane solvate generated routinely as a mixture with Form C (desolvated form) from DCM. Form B will desolvate fully to Form C when exposed to temperatures between 100 and 120° C.

Figure 13:
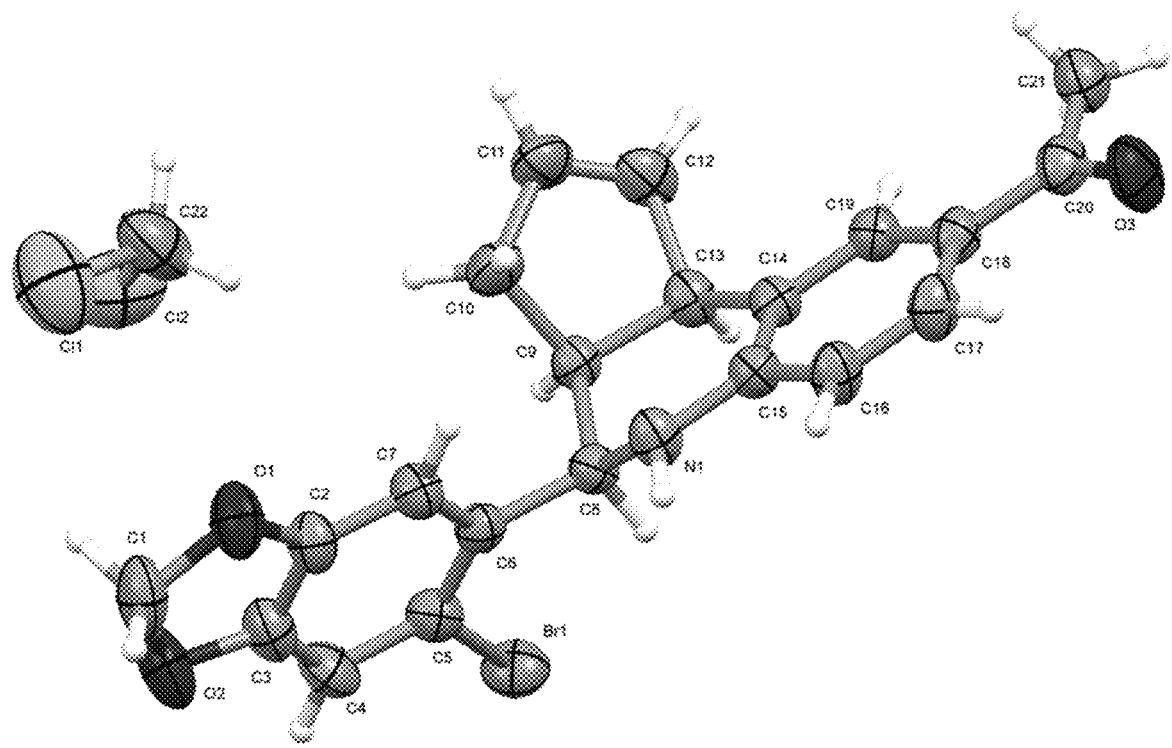
FIG. 13 shows the Atomic displacement ellipsoid diagram of SRR G-1 Form B.
Figure 14:
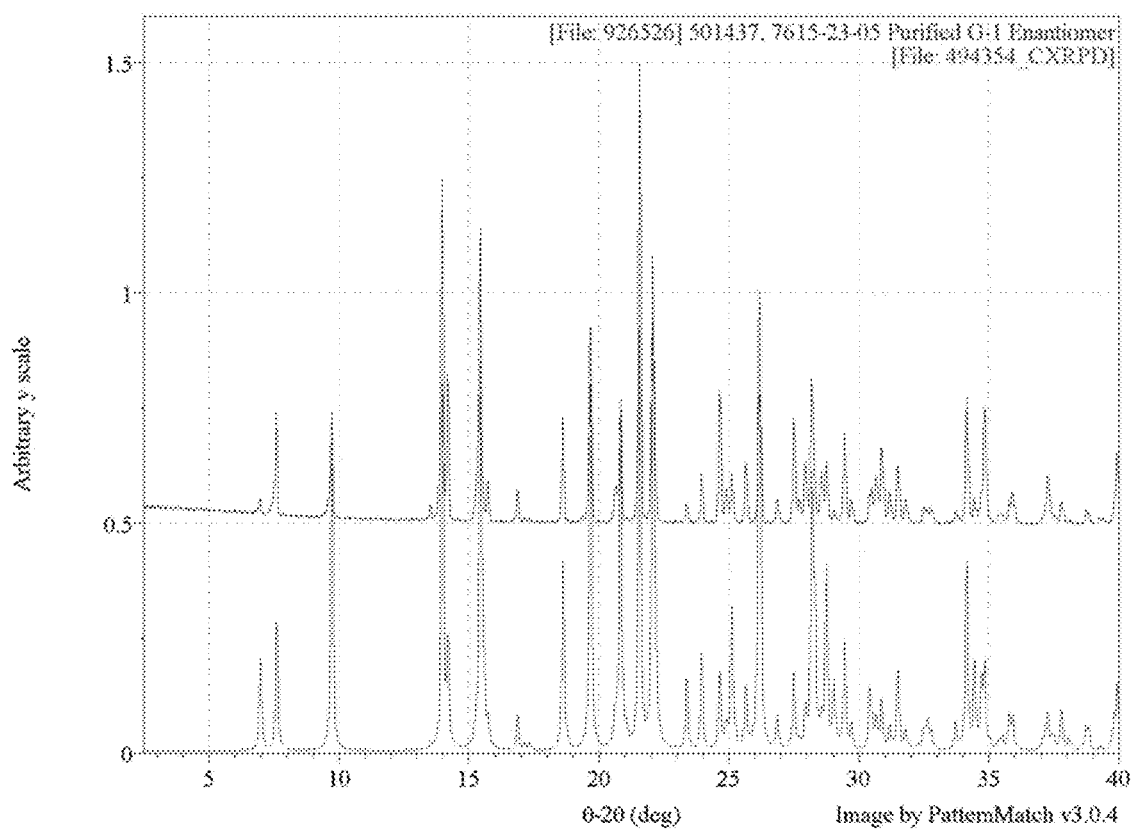
FIG. 14 shows the Calculated and experimental XRPD patterns for SRR G-1 Form B.

The single crystal structure for Form B is known. The crystal system is orthorhombic and the space group is $P2_12_12_1$. The cell parameters and calculated volume are: α=6.43156(10) Å, b=13.0752(2) Å, c=25.2941(4) Å, α=90°, β=90°, γ=90°, V=2127.09(6) Å$^3$. The formula weight is 497.20 g mol$^{-1}$ with Z=4, resulting in a calculated density of 1.553 g cm$^{-3}$. The asymmetric unit contains one enantiopure SRR G-1 molecule and one dichloromethane molecule. The structure contains three chiral centers located at C8, C9, and C13 (refer to FIG. 13) which bond in the R, S, and R configuration, respectively. A calculated XRPD pattern of Form B, generated from the single crystal structure, is provided in FIG. 14 and compared to the experimental pattern.

The observed XRPD peaks for Crystalline Form B are listed in Table 11

TABLE 11

| Diffraction angle 2θ (°) | d-spacing (Å) | Intensity (%) |
|---|---|---|
| 6.97 ± 0.20 | 12.677 ± 0.363 | 7 |
| 7.60 ± 0.20 | 11.627 ± 0.306 | 25 |
| 9.71 ± 0.20 | 9.097 ± 0.187 | 25 |
| 13.53 ± 0.20 | 6.540 ± 0.096 | 6 |
| 13.98 ± 0.20 | 6.331 ± 0.090 | 75 |
| 14.19 ± 0.20 | 6.236 ± 0.087 | 33 |
| 15.44 ± 0.20 | 5.735 ± 0.074 | 64 |
| 15.73 ± 0.20 | 5.628 ± 0.071 | 11 |
| 16.87 ± 0.20 | 5.251 ± 0.062 | 9 |
| 17.14 ± 0.20 | 5.168 ± 0.060 | 3 |
| 17.33 ± 0.20 | 5.114 ± 0.059 | 3 |
| 18.61 ± 0.20 | 4.764 ± 0.051 | 24 |
| 19.36 ± 0.20 | 4.582 ± 0.047 | 3 |
| 19.67 ± 0.20 | 4.510 ± 0.045 | 44 |
| 20.64 ± 0.20 | 4.299 ± 0.041 | 10 |
| 20.82 ± 0.20 | 4.262 ± 0.040 | 28 |
| 21.06 ± 0.20 | 4.216 ± 0.040 | 3 |
| 21.55 ± 0.20 | 4.119 ± 0.038 | 100 |

TABLE 11-continued

| Diffraction angle 2θ (°) | d-spacing (Å) | Intensity (%) |
|---|---|---|
| 22.05 ± 0.20 | 4.027 ± 0.036 | 57 |
| 23.36 ± 0.20 | 3.806 ± 0.032 | 6 |
| 23.96 ± 0.20 | 3.712 ± 0.031 | 12 |
| 24.65 ± 0.20 | 3.608 ± 0.029 | 30 |
| 24.91 ± 0.20 | 3.572 ± 0.028 | 9 |
| 25.11 ± 0.20 | 3.544 ± 0.028 | 12 |
| 25.66 ± 0.20 | 3.469 ± 0.027 | 15 |
| 26.18 ± 0.20 | 3.401 ± 0.026 | 29 |
| 26.86 ± 0.20 | 3.317 ± 0.024 | 7 |
| 27.50 ± 0.20 | 3.241 ± 0.023 | 24 |
| 27.71 ± 0.20 | 3.217 ± 0.023 | 7 |
| 27.94 ± 0.20 | 3.191 ± 0.022 | 15 |
| 28.18 ± 0.20 | 3.164 ± 0.022 | 32 |
| 28.54 ± 0.20 | 3.125 ± 0.021 | 13 |
| 28.75 ± 0.20 | 3.103 ± 0.021 | 15 |
| 29.03 ± 0.20 | 3.073 ± 0.021 | 4 |
| 29.44 ± 0.20 | 3.031 ± 0.020 | 20 |
| 29.70 ± 0.20 | 3.005 ± 0.020 | 7 |

Figure 15A:
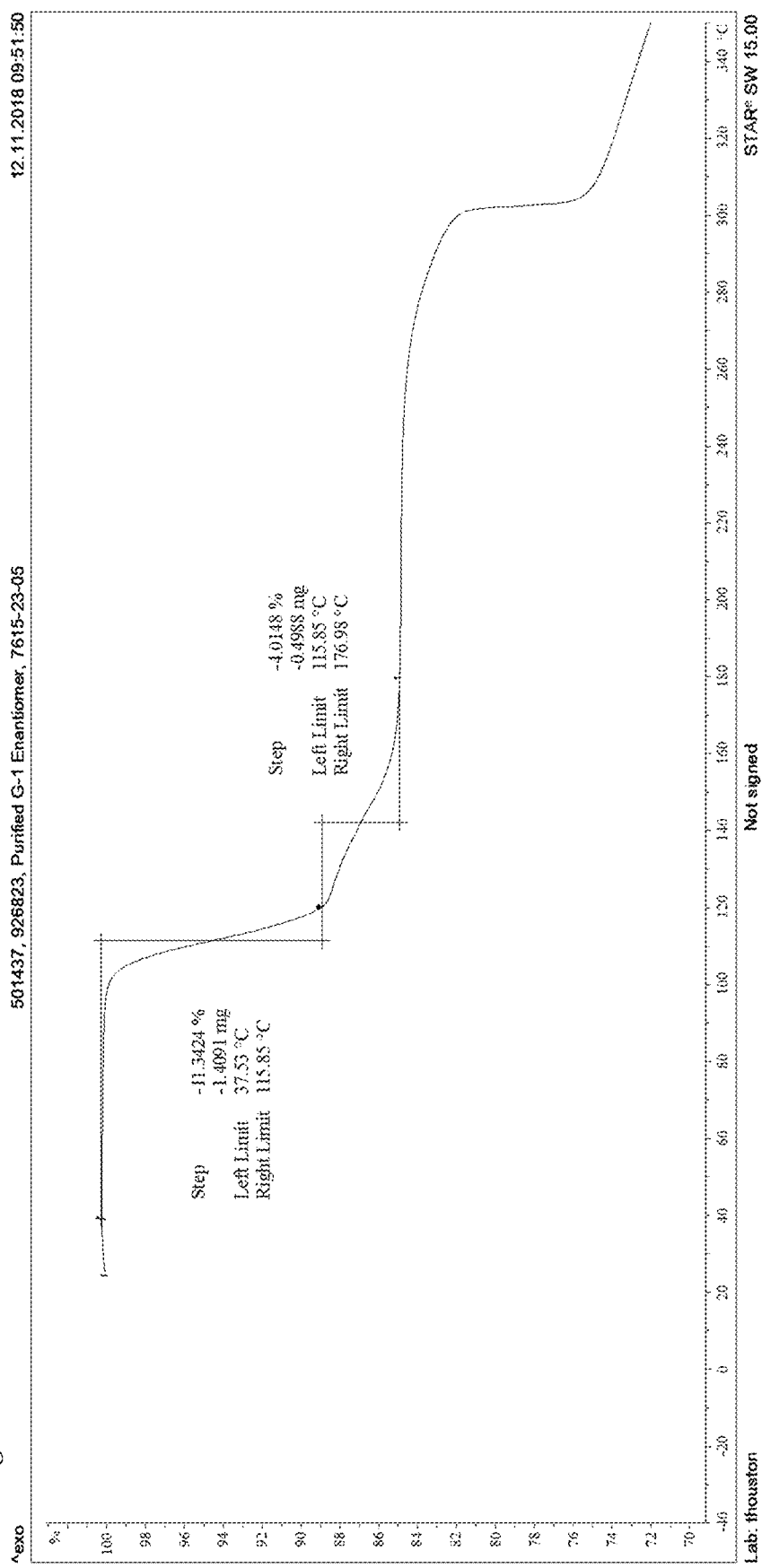
FIGS. 15A and 15B show the Thermograms for SRR G-1 Form B.
Figure 15B:
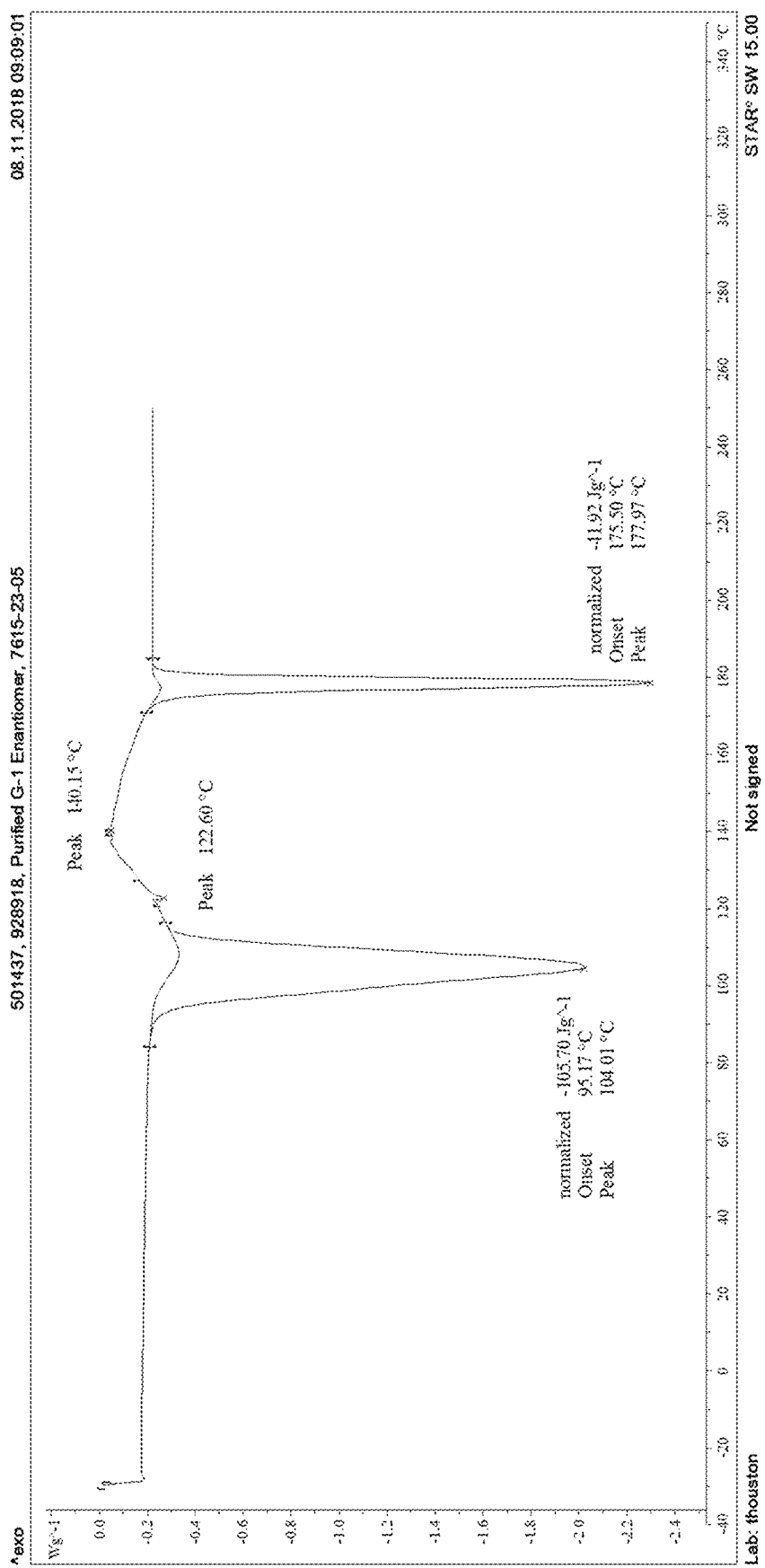
Figure 16:
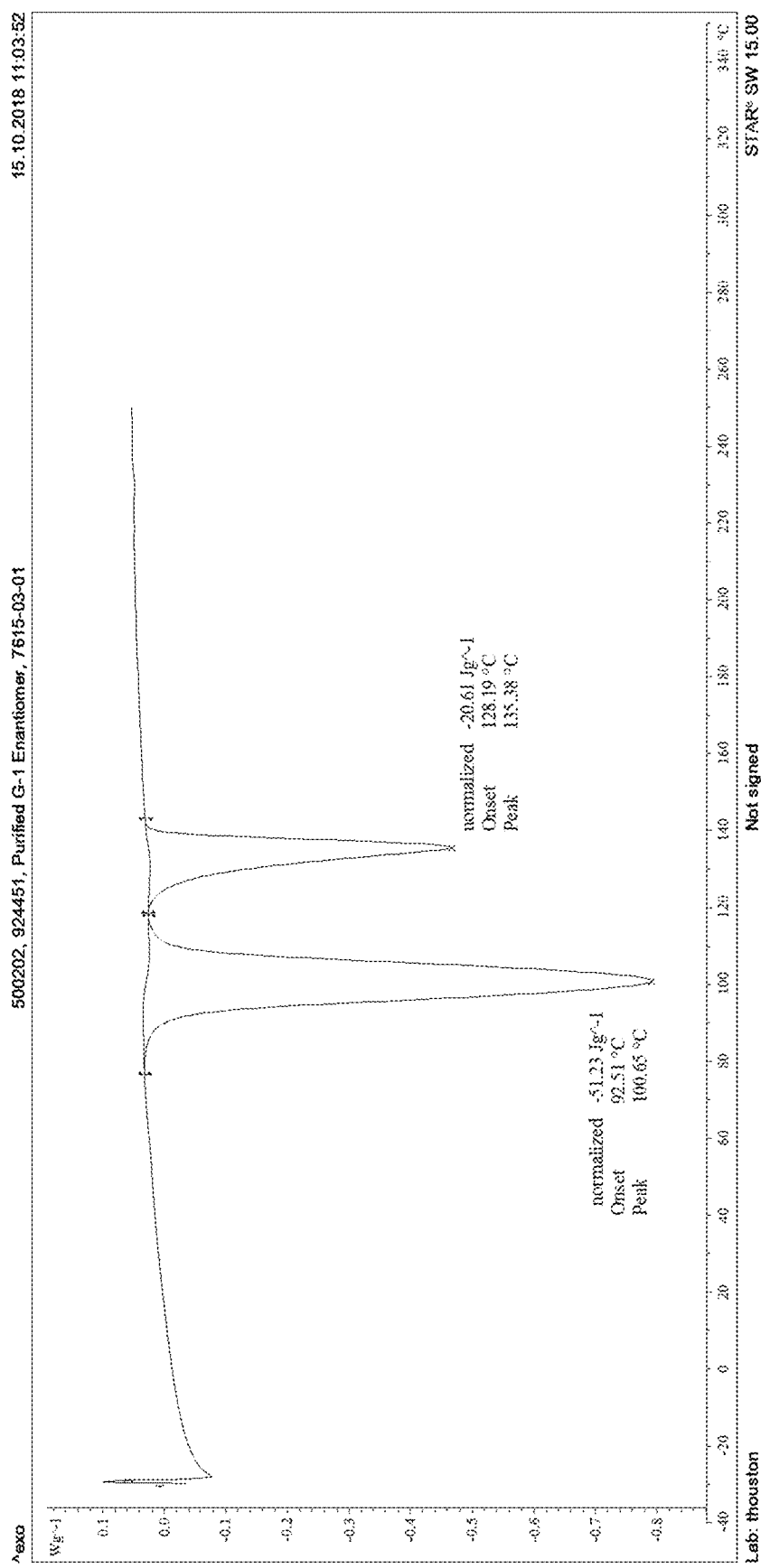
FIGS. 16A and 16B show the DSC thermogram for mixture SRR G-1 Forms B and C.

The thermograms for Form B are shown in FIGS. 15A and 15B. The Thermogravametric Analysis (TGA) curve exhibits a weight loss of approximately 15.3% up to 177° C., consistent with the volatilization of 0.9 mol/mol DCM. The loss occurs concurrently with a desolvation endotherm (max 104° C.) and recrystallization exotherm (max 140° C.) in the DSC thermogram. The recrystallized material exhibits a final melt endotherm with an onset near 176° C. consistent with the melt of Form A. The DSC thermogram for the mixture of Forms B and C is provided in FIGS. 16A and 16B. The mixture exhibits a desolvation endotherm (max 101° C.) followed by the melt endotherm (onset near 128° C.) of the desolvated form, Form C.

The physical stability of Form B was investigated. Complete desolvation to Form C occurred upon exposure to 120° C. Almost complete desolvation was evident upon exposure to 90 to 100° C. for 25 minutes. Vacuum at 70° C. (or below) was not sufficient for desolvation to occur.

Crystalline Form C

Form C is a desolvate with a melt onset near 129° C. generated through the desolvation of Form B (mono DCM solvate).

Figure 17:
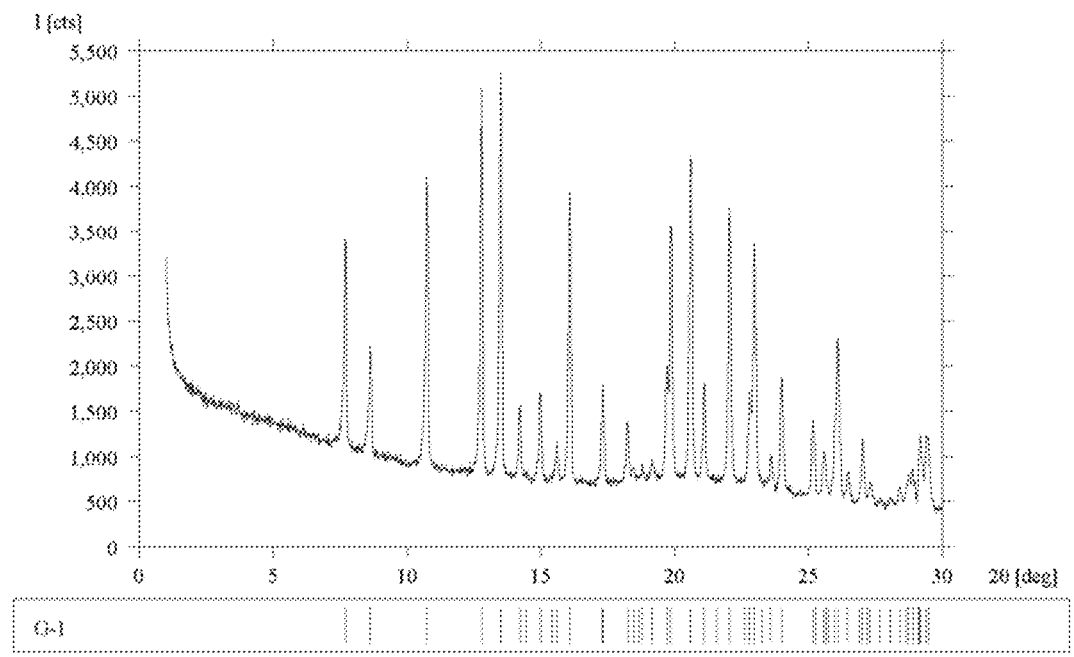
FIG. 17 shows the XRPD indexing results for SRR G-1 Form C.

The XRPD pattern of Form C was successfully indexed, suggesting it is composed of a single crystalline phase (FIG. 17). Assuming the chemical composition is correct, it has an orthorhombic unit cell containing four molecules of SRR G-1. Consequently, the formula unit volume of 462.88 Å$^3$ calculated from the indexing results would be consistent with an anhydrous form with a calculated density of 1.479 g cm$^{-3}$.

The observed XRPD peaks for Crystalline Form C are listed in Table 12

TABLE 12

| Diffraction angle 2θ (°) | d-spacing (Å) | Intensity (%) |
|---|---|---|
| 7.69 ± 0.20 | 11.483 ± 0.298 | 65 |
| 8.62 ± 0.20 | 10.250 ± 0.237 | 42 |
| 10.73 ± 0.20 | 8.235 ± 0.153 | 78 |
| 12.77 ± 0.20 | 6.925 ± 0.108 | 97 |
| 13.49 ± 0.20 | 6.560 ± 0.097 | 100 |
| 14.22 ± 0.20 | 6.222 ± 0.087 | 30 |
| 14.99 ± 0.20 | 5.906 ± 0.078 | 33 |
| 15.60 ± 0.20 | 5.674 ± 0.072 | 22 |
| 16.09 ± 0.20 | 5.506 ± 0.068 | 74 |
| 17.32 ± 0.20 | 5.117 ± 0.059 | 34 |
| 18.24 ± 0.20 | 4.860 ± 0.053 | 26 |
| 19.17 ± 0.20 | 4.626 ± 0.048 | 18 |
| 19.71 ± 0.20 | 4.500 ± 0.045 | 39 |
| 19.86 ± 0.20 | 4.466 ± 0.045 | 68 |
| 20.60 ± 0.20 | 4.308 ± 0.041 | 82 |
| 21.10 ± 0.20 | 4.206 ± 0.039 | 35 |
| 22.05 ± 0.20 | 4.028 ± 0.036 | 71 |
| 22.78 ± 0.20 | 3.900 ± 0.034 | 33 |
| 22.98 ± 0.20 | 3.868 ± 0.033 | 62 |
| 23.59 ± 0.20 | 3.768 ± 0.031 | 19 |
| 24.00 ± 0.20 | 3.706 ± 0.030 | 36 |
| 25.16 ± 0.20 | 3.536 ± 0.028 | 27 |
| 25.57 ± 0.20 | 3.481 ± 0.027 | 20 |
| 26.09 ± 0.20 | 3.413 ± 0.026 | 44 |
| 26.46 ± 0.20 | 3.366 ± 0.025 | 16 |
| 27.01 ± 0.20 | 3.299 ± 0.024 | 22 |
| 27.30 ± 0.20 | 3.264 ± 0.023 | 14 |
| 28.41 ± 0.20 | 3.139 ± 0.022 | 13 |
| 28.76 ± 0.20 | 3.102 ± 0.021 | 15 |
| 28.90 ± 0.20 | 3.087 ± 0.021 | 16 |
| 29.18 ± 0.20 | 3.058 ± 0.021 | 24 |
| 29.43 ± 0.20 | 3.032 ± 0.020 | 23 |
| 30.23 ± 0.20 | 2.954 ± 0.019 | 39 |

Figure 18:
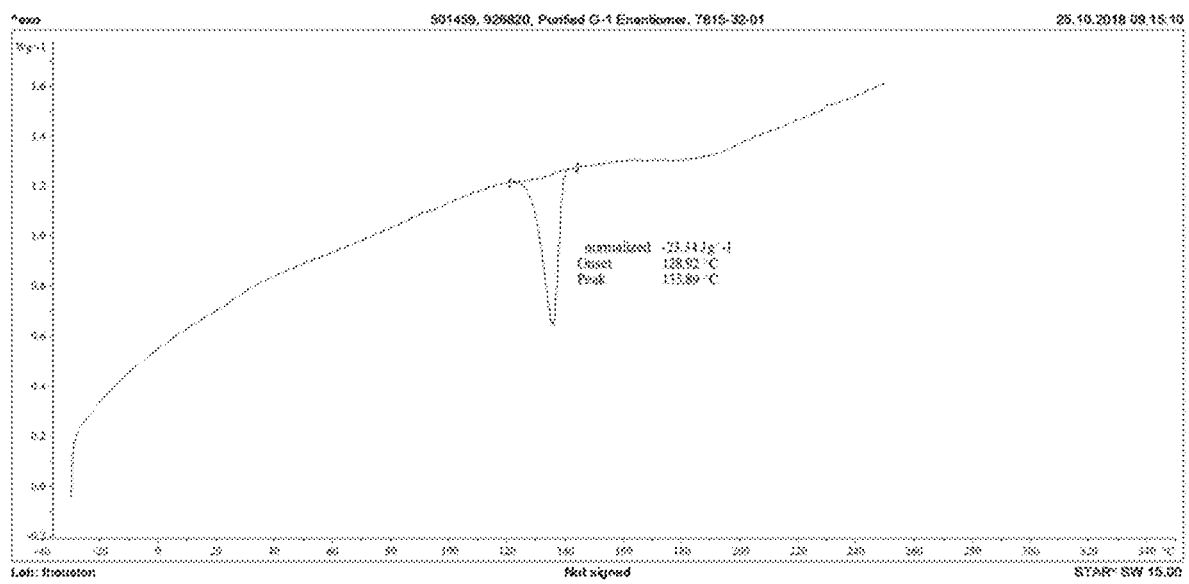
FIG. 18 shows the DSC thermogram for SRR G-1 Form C.

The differential scanning calorimetry (DSC) thermogram for Form C is shown in FIG. 18. The DSC exhibits a single endotherm with an onset near 129° C. (23 J/g). The event was visually confirmed on a hot plate as a melt.

Amorphous

The physical stability of amorphous material generated from purified SRR G-1 was investigated. Amorphous material crystallized to Form A upon exposure to either elevated temperature (within 4 days at 60° C.) or humidity (within 12 days at 75% RH). This indicates that amorphous material is not stable at the conditions evaluated.

Relative Thermodynamic Stability of the Crystalline Forms

Phase transitions of solids can be thermodynamically reversible or irreversible. Crystalline forms which transform reversibly at a specific transition temperature are called enantiotropic polymorphs. If the crystalline forms are not interconvertible under these conditions, the system is monotropic (one thermodynamically stable form). Several rules help predict the relative thermodynamic stability of polymorphs and whether the relationship between the polymorphs is enantiotropic or monotropic. The density and heat of fusion rules, justified on a statistical mechanical basis, are used here for guidance of monotropy or enantiotropy.

The density rule, which is based on Kitaĭgorodskiĭ's principle of closest packing for molecular crystals, states that, for a non-hydrogen-bonded system at absolute zero, the most stable polymorph will have the highest density, because of stronger intermolecular van der Waals interactions. Thus, according to this rule, the crystal structure with most efficient packing will also have the lowest free energy. This assumes that hydrogen bonding (long range effect) is not a major parameter in crystal packing. The densities determined from the single crystal structure of Form A and indexing results of Form C suggest that, at absolute zero, Form A is more stable than Form C (1.485 and 1.479 g cm$^3$, respectively).

The melt onsets and heats of fusion, obtained from calorimetry data, are useful to estimate the relative physical stabilities of the forms at all temperatures (FIGS. 11A, 11B, and 18). From the heat of fusion rule, two forms are enantiotropic if the higher melting form has the lower heat of fusion, otherwise they are monotropic. The density and heat of fusion rules for this system appear consistent with a monotropic relationship.

Interconversion experiments were performed to experimentally test the thermodynamic relationship between Forms A and C. Interconversion or competitive slurry experiments are a solution-mediated process that provides a pathway for the less soluble (more stable) crystal to grow at the expense of the more soluble crystal form. Outside the formation of a solvate or degradation, the resulting more stable polymorph from an interconversion experiment is independent of the solvent used because the more thermodynamically stable polymorph has a lower energy and therefore lower solubility. The choice of solvent affects the kinetics of polymorph conversion and not the thermodynamic relationship between polymorphic forms. Saturated solutions were generated and then added to mixtures composed of approximately equivalent quantities of the two polymorphs. The samples were slurried for nine days and the solids harvested and analyzed by XRPD. The results of the interconversion studies confirm Form A is thermodynamically more stable at room temperature relative to Form C. The experimentally determined relative stability at room temperature, the suggested relative stability at absolute zero based on the density rule, and monotropism as determined by the heat of fusion rule all imply that Form A is more stable than Form C at any temperature.

Solubility of SRR G-1 Form A

TABLE 13

Approximate Solubility of Purified SRR G-1 Form A

| Solvent | Solubility (mg/mL) |
| --- | --- |
| acetone | >122 |
| ACN | 24 |
| DCM | >89 |
| DMSO | >203 |
| diethyl ether | 8 |
| EtOH | 7 |
| EtOAc | >65 |
| IPA | 4 |

TABLE 13-continued

Approximate Solubility of Purified SRR G-1 Form A

| Solvent | Solubility (mg/mL) |
| --- | --- |
| MeOH | 6 |
| sesame oil | 2 |
| THF | >67 |
| toluene | 40 |
| water | <2 |

SRR G-1 (Form A) Solubility Measurement in pH Buffers

Figure 19:
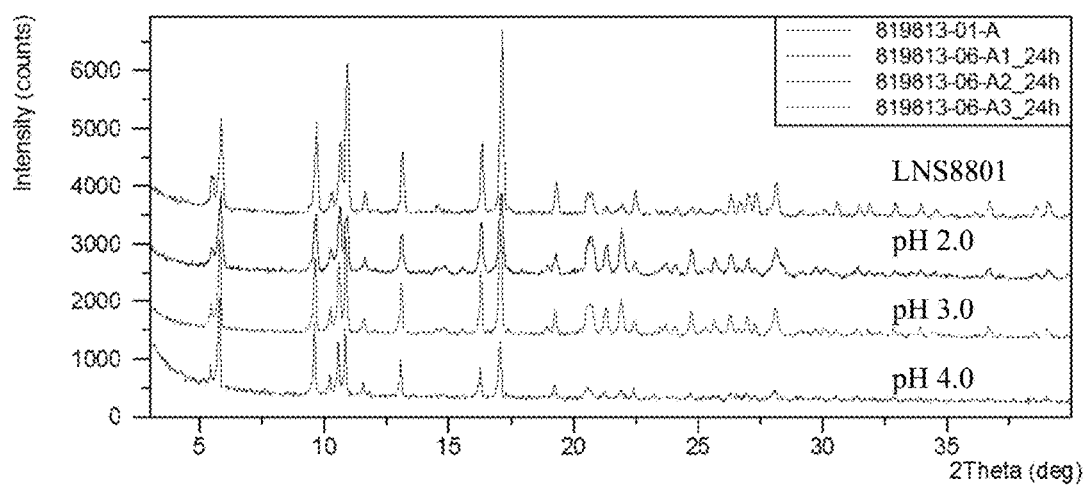
FIG. 19 shows the XRPD overlay of residual solids after pH solubility test (I/II).
Figure 20:
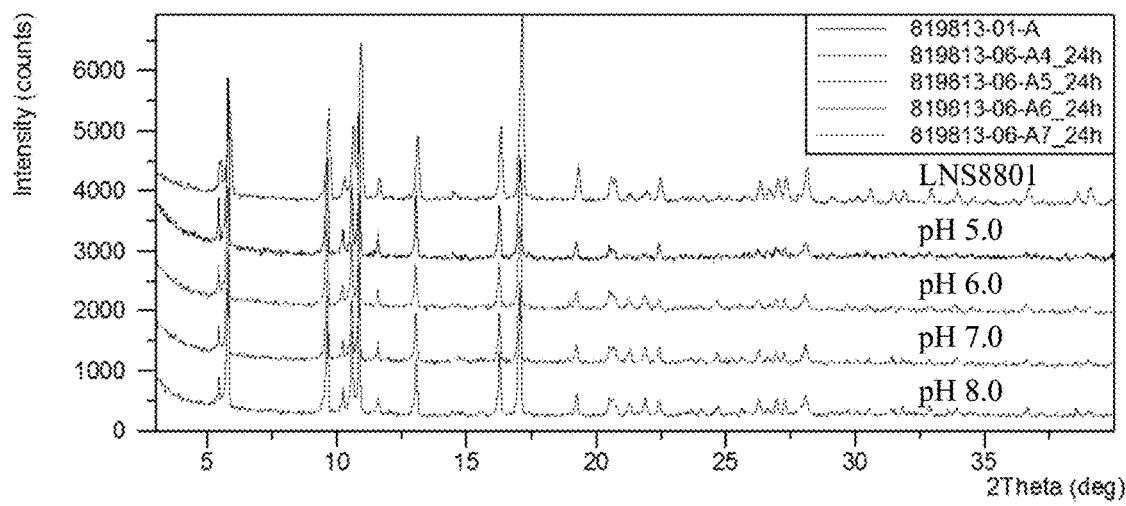
FIG. 20 shows the XRPD overlay of residual solids after pH solubility test (II/II).

Solubility measurement was performed for SRR G-1 (crystal Form A) in pH buffers (2.0~8.0) at 37° C. for 24 hrs. The results were summarized in Table 14. The XRPD patterns are shown in FIG. 19 and FIG. 20. No form change was observed for the compound in all the pH buffers after 24 hrs. The solubility at pH 2.0~8.0 for SRR G-1 was less than 0.72 µg/mL.

TABLE 14

Summary of solubility measurement of SRR G-1 (Form A) in pH buffers

| Media | Temp. | Solubility | Final pH | Form Conversion |
| --- | --- | --- | --- | --- |
| pH 2.0 | 37° C. | <0.72 µg/mL | 2.0 | No |
| pH 3.0 | | <0.72 µg/mL | 3.0 | No |
| pH 4.0 | | <0.72 µg/mL | 3.8 | No |
| pH 5.0 | | <0.72 µg/mL | 5.1 | No |
| pH 6.0 | | <0.72 µg/mL | 6.1 | No |
| pH 7.0 | | <0.72 µg/mL | 7.1 | No |
| pH 8.0 | | <0.72 µg/mL | 8.0 | No |

SRR G-1 (Form A) Solubility Measurement in BioRelovent Media

Figure 21:
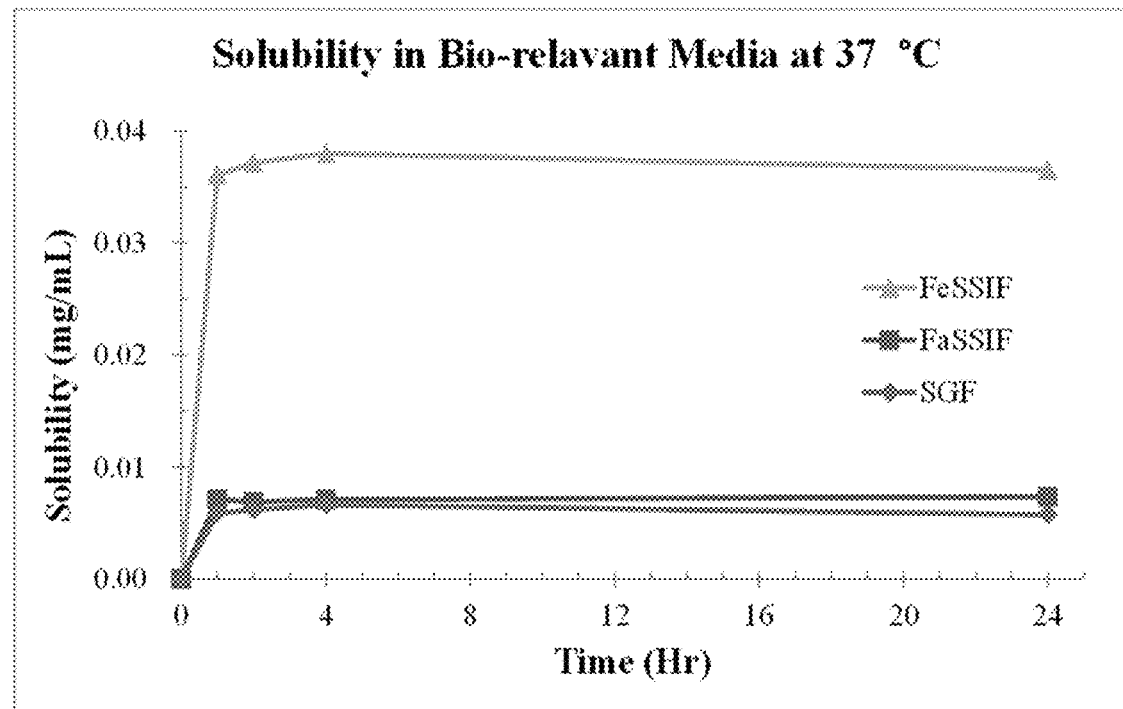
FIG. 21 shows the Solubility of SRR G-1 freebase in bio-relevant media.
Figure 22:
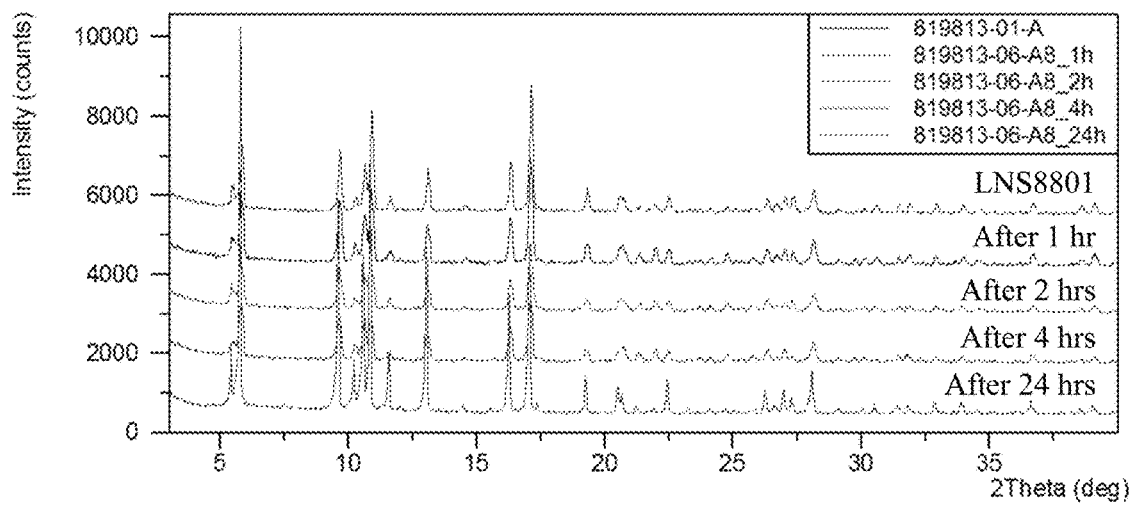
FIG. 22 shows the XRPD overlay of SRR G-1 after solubility test in SGF.
Figure 23:
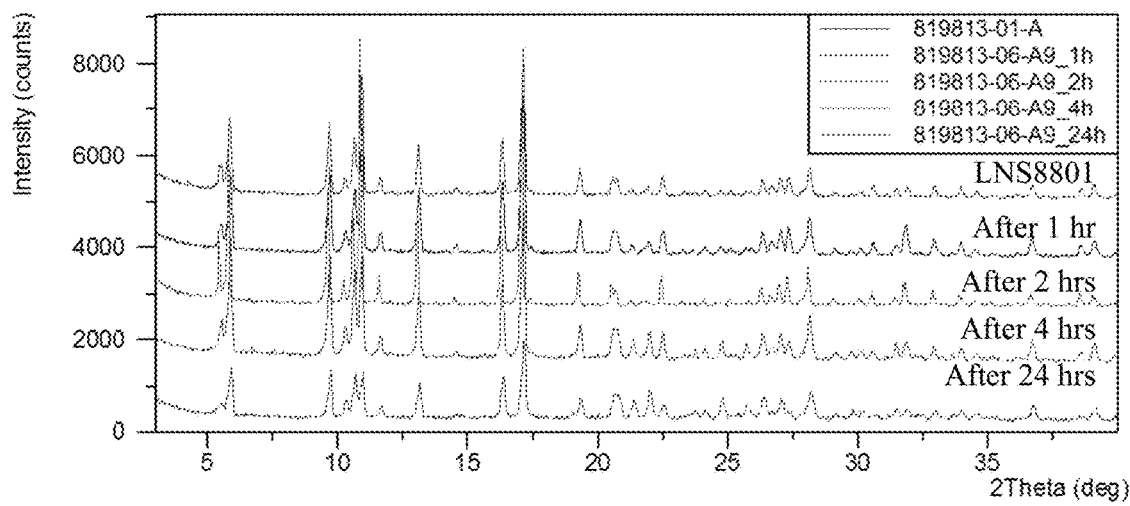
FIG. 23 shows the XRPD overlay of SRR G-1 after solubility test in FaSSIF.
Figure 24:
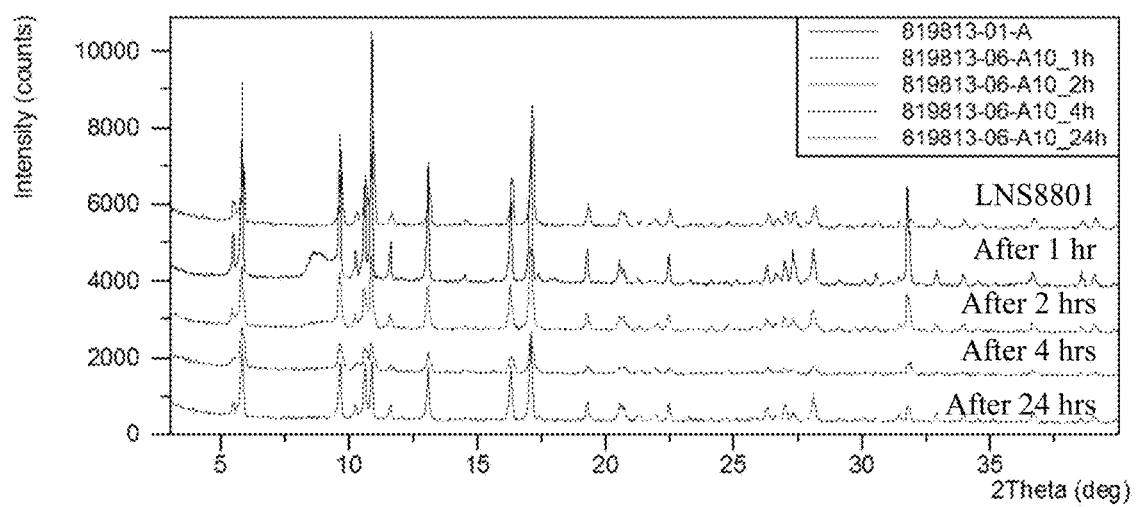
FIG. 24 shows the XRPD overlay of SRR G-1 after solubility test in FeSSIF.

Kinetic solubility measurement was performed for SRR G-1 (crystal Form A) in three bio-relevant media (SGF (pH 1.8), FaSSIF (pH 6.5) and FeSSIF (pH 5.0)) at 37° C. for 1, 2, 4 and 24 hrs. The results were summarized in Table 15 and FIG. 21. The XRPD patterns of the wetcake are shown in FIGS. 22-24. No form change was observed for the sample after 1, 2, 4 and 24 hrs in the three bio-relevant media. The highest solubility of SRR G-1 was observed in FeSSIF (~0.037 mg/mL).

TABLE 15

Summary of solubility measurement in bio-relevant media

| | SGF | | | FaSSIF | | | FeSSIF | |
| --- | --- | --- | --- | --- | --- | --- | --- | --- |
| Time Point (h) | Form Change | Solubility (mg/mL) | pH FC | Solubility (mg/mL) | pH FC | Solubility (mg/mL) | pH |
| 1 | No | 0.0059 | 1.9 No | 0.0071 | 6.4 No | 0.036 | 5.0 |
| 2 | No | 0.0062 | 1.9 No | 0.0068 | 6.4 No | 0.037 | 5.0 |
| 4 | No | 0.0066 | 1.9 No | 0.0071 | 6.4 No | 0.038 | 5.0 |
| 24 | No | 0.0057 | 1.7 No | 0.0073 | 6.5 No | 0.037 | 5.0 |

The pKa, Log $D_{7.4}$ and Log P of compound SRR G-1 were predicted by MarvinSketch 5.6.0.2, the results showed the pKa of SRR G-1 is 1.90 (base, pH range of 0~14), Log $D_{7.4}$ is 5.32 and Log P is 5.32. A pKa titration test showed that no pKa value was observed in the range of 3~11, which was consistent with the prediction result. Log $D_{7.4}$ was measured with the solvent systems of pH 7.4 phosphate buffer and n-octanol by shake-flask method. Detailed results of Log $D_{7.4}$ and Log P were displayed in Table 16. Since the solubility of SRR G-1 freebase in aqueous phase was lower than <0.82 µg/mL, the Log $D_{7.4}$ was determined to be >3.22 and Log P was >3.22 considering the small pKa value.

TABLE 16

LogD$_{7.4}$ and LogP of compound SRR G-1

| Sample Name | # | Concentration (mg/mL) n-octanol | pH buffer 7.4 | LogD$_{7.4}$ | Average of LogD$_{7.4}$ | Simulated LogD$_{7.4}$ | LogP* | Simulated LogP |
|---|---|---|---|---|---|---|---|---|
| SRR G-1 | 1 | 1.37 | <0.82 µg/mL | >3.22 | >3.22 | 5.32 | >3.22 | 5.32 |
| | 2 | 1.34 | <0.82 µg/mL | >3.21 | | | | |
| | 3 | 1.37 | <0.82 µg/mL | >3.22 | | | | |

*LogP = LogD$_{(pH)}$ + Log [1 + 10$^{(pKa - pH)}$]

Instrumental Techniques
Differential Scanning Calorimetry (DSC)

DSC was performed using a Mettler-Toledo DSC3+ or DSC822e differential scanning calorimeter. A tau lag adjustment is performed with indium, tin, and zinc. The temperature and enthalpy are adjusted with octane, phenyl salicylate, indium, tin and zinc. The adjustment is then verified with octane, phenyl salicylate, indium, tin, and zinc. The sample was placed into a hermetically sealed aluminum DSC pan, and the weight was accurately recorded. The pan was then inserted into the DSC cell. A weighed aluminum pan configured as the sample pan was placed on the reference side of the cell. The pan lid was pierced prior to sample analysis. Samples were analyzed from −30° C. to 250° C. @ 10°/min. The cyclic DSC method heated from −30° C. to 100° C., returned to −30° C., then heated to 250° C. at 10°/min.

Dynamic Vapor Sorption/Desorption (DVS)

Moisture sorption/desorption data were collected on a VTI SGA-100 Vapor Sorption Analyzer. NaCl and PVP were used as calibration standards. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Thermogravimetric Analysis (TGA)

Thermogravimetric analysis was performed using a Mettler-Toledo TGA/DSC3 analyzer. Temperature and enthalpy adjustments were performed using indium, tin, and zinc, and then verified with indium. The balance was verified with calcium oxalate. The sample was placed in an open aluminum pan. The sample was hermetically sealed, the lid pierced, then inserted into the TG furnace. A weighed aluminum pan configured as the sample pan was placed on the reference platform. The furnace was heated under nitrogen. Each sample was heated from ambient temperature to 350° C. at 10° C./min. Although thermograms are plotted by reference temperature (x-axis), results are reported according to sample temperatures.

X-Ray Powder Diffraction (XRPD)

XRPD pattern was collected with a PANalytical X'Pert PRO MPD or PANalytical Empyrean diffractometer using an incident beam of Cu radiation produced using a long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-µm-thick films and analyzed in transmission geometry. A beam-stop, short antiscatter extension, and antiscatter knife edge were used to minimize the background generated by air. Soller slits for the incident and diffracted beams were used to minimize broadening and asymmetry from axial divergence. Diffraction patterns were collected using a scanning position-sensitive detector (X'Celerator) located 240 mm from the specimen and Data Collector software v. 2.2b or 5.5.

Example 4: Salt Data

Figure 25:
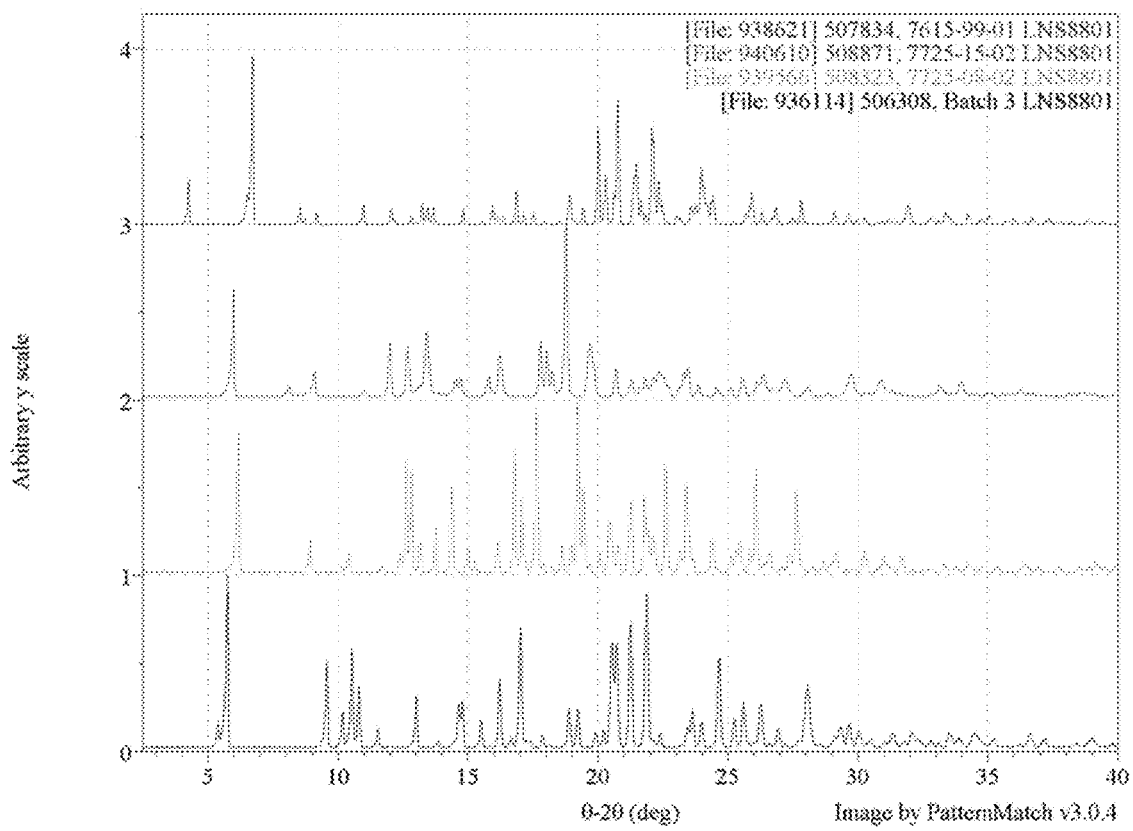
FIG. 25 shows the XRPD patterns of SRR G-1 salts.

Crystalline and anhydrous SRR G-1 besylate, camsylate, and napsylate salts were successfully isolated. All three were obtained as 1:1 stoichiometric salts. For these, seeding was crucial in providing high yields of crystalline salts that were not discolored. The XRPD patterns of the salts are compared with freebase Form A in FIG. 25. Scale-up and characterization of the salts are described in more detail in subsequent sections below.

SRR G-1 Besylate Form A

SRR G-1 Besylate Form A is an anhydrous 1:1 stoichiometric salt with an apparent melt onset near 186° C. Disproportionation of the salt in water was not evident.

The single-crystal structure of SRR G-1 Besylate Form A was determined successfully. Thus colorless needle having approximate dimensions of 0.23×0.09×0.04 mm$^3$, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector. Cell constants and an orientation matrix for data collection were obtained from least-squares refinement using the setting angles of 13177 reflections in the range 4.2570°<θ<77.0580°. The space group was determined by the program CRYSALISPRO to be P2$_1$. The data were collected to a maximum diffraction angle (2θ) of 155.242° at room temperature.

Frames were integrated with CRYSALISPRO. A total of 26894 reflections were collected, of which 10520 were unique. Lorentz and polarization corrections were applied to the data. The linear absorption coefficient is 3.323 mm$^{-1}$ for Cu Kα radiation. An empirical absorption correction using CRYSALISPRO was applied. Transmission coefficients ranged from 0.837 to 1.000. Intensities of equivalent reflections were averaged. The agreement factor for the averaging was 3.3% based on intensity.

The structure was solved by direct methods using S$_{HELXT}$. The remaining atoms were located in succeeding difference Fourier syntheses. The structure was refined using S$_{HELXL}$-2014. Hydrogen atoms were refined independently. The structure was refined in full-matrix least-squares by minimizing the function:

$$\Sigma w(|F_o|^2 - |F_c|^2)^2$$

where the weight, w, is defined as 1/[σ$^2$(F$_o^2$)+(0.0401 P)$^2$+ (0.3205 P)], where P=(F$_o^2$+2F$_c^2$)/3. Scattering factors were taken from the "International Tables for Crystallography". Of the 10520 reflections used in the refinements, only the reflections with intensities larger than twice their uncertainty [I>2σ(I)], 9411, were used in calculating the fit residual, R. The final cycle of refinement included 723 variable parameters, 1 restraint, and converged with respective unweighted and weighted agreement factors of:

$$R = \Sigma |F_o - F_c| / \Sigma F_o = 0.0348$$

$$R_w = \sqrt{(\Sigma_w (F_o^2 - F_c^2)^2 / \Sigma w (F_o^2)^2)} = 0.0874$$

The standard deviation of an observation of unit weight (goodness of fit) was 1.05. The highest peak in the final difference Fourier had an electron density of 0.311 e/Å$^3$. The minimum negative peak had a value of −0.280 e/Å$^3$.

Figure 26:
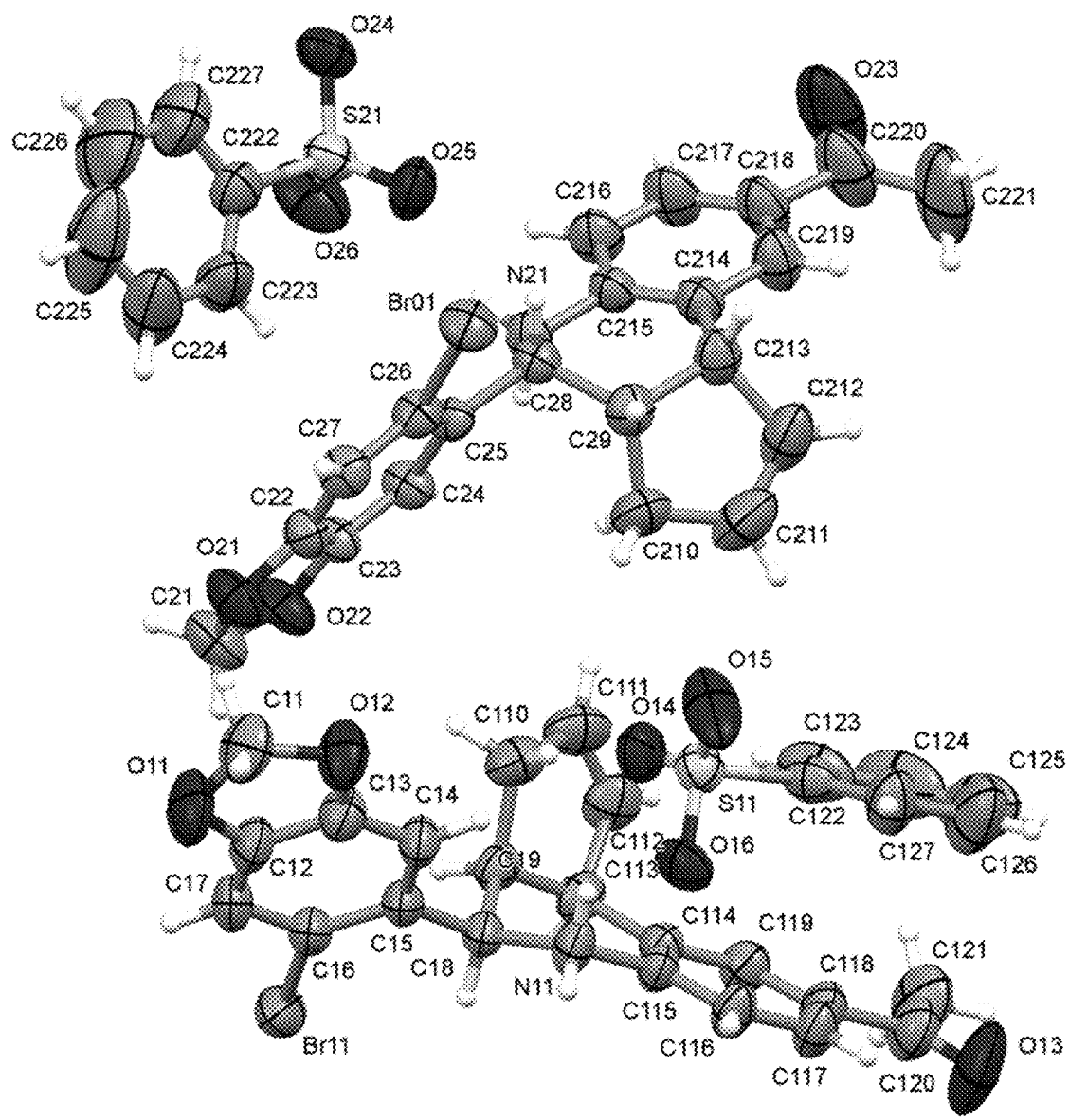
FIG. 26 shows the Atomic displacement ellipsoid diagram of SRR G-1 Besylate Form A.
Figure 27:
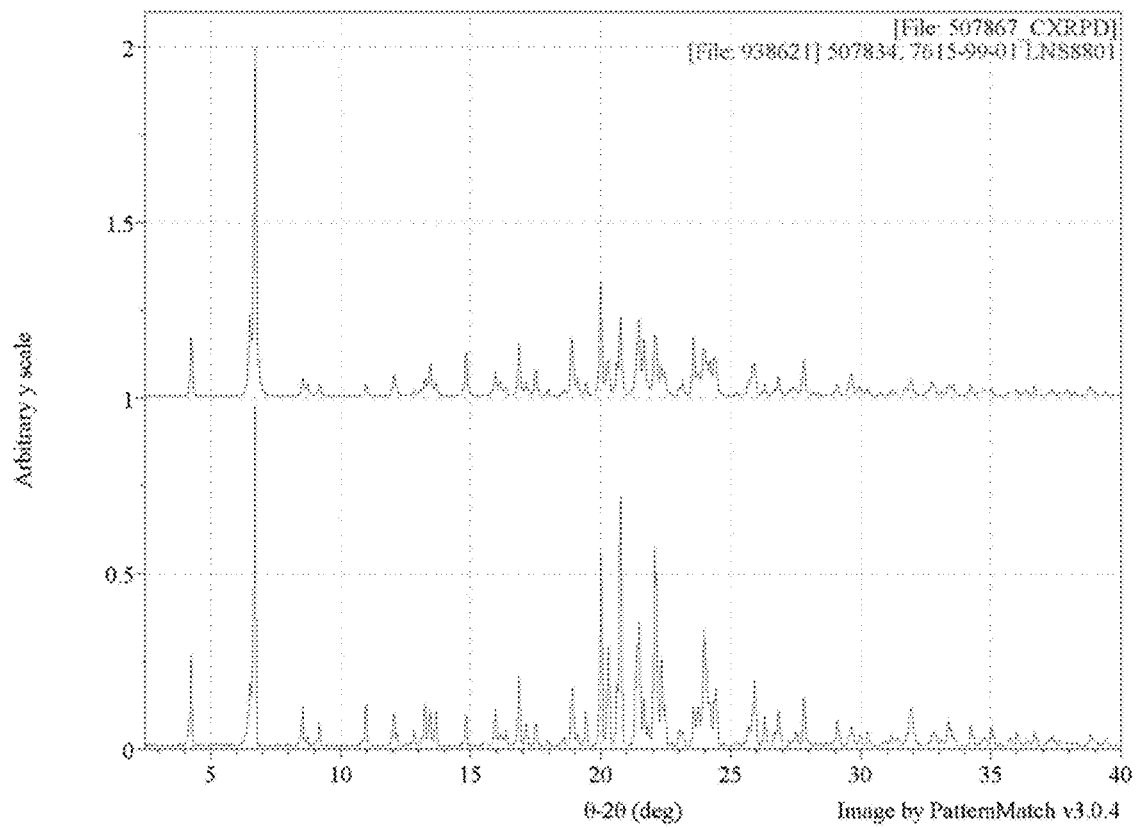
FIG. 27 shows the Calculated and experimental XRPD patterns for SRR G-1 Besylate Form A.

The crystal system is monoclinic and the space group is P2$_1$. The cell parameters and calculated volume are: a=14.1207(3) Å, b=8.74139(11) Å, c=21.5361(4) Å, α=90°, β=106.1889(19)°, γ=90°, V=2552.89(8) Å$^3$. The formula weight is 570.44 g mol$^{-1}$ with Z=4, resulting in a calculated density of 1.484 g cm$^{-3}$. Further details of the crystal data and crystallographic data collection parameters are summarized in Table 17. An atomic displacement ellipsoid drawing of Besylate Form A is shown in FIG. 26. The asymmetric unit shown contains two SRR G-1 cations and two besylate anions. The —SO$_3$ moiety was modeled with rotational disorder on both anions. A calculated XRPD pattern generated for Cu radiation using MERCURY and the atomic coordinates, space group, and unit cell parameters from the single crystal structure is provided in FIG. 27 and compared to the experimental pattern.

TABLE 17

| SRR G-1 Besylate Form A Crystal Data and Data Collection Parameters | |
|---|---|
| Empirical formula | C$_{27}$H$_{24}$BrNO$_6$S |
| Formula weight (g mol$^{-1}$) | 570.44 |
| Temperature (K) | 299.64(13) |
| Wavelength (Å) | 1.54184 |
| Crystal system | monoclinic |
| Space group | P2$_1$ |
| Unit cell parameters | |
| a = 14.1207(3) Å | α = 900 |
| b = 8.74139(11) Å | β = 106.1889(19)° |
| c = 21.5361(4) Å | γ = 90° |
| Unit cell volume (Å$^3$) | 2552.89(8) |
| Cell formula units, Z | 4 |
| Calculated density (g cm$^{-3}$) | 1.484 |
| Absorption coefficient (mm$^{-3}$) | 3.323 |
| F(000) | 1168 |
| Crystal size (mm$^3$) | 0.23 × 0.09 × 0.04 |
| Reflections used for cell measurement | 13177 |
| θ range for cell measurement | 4.2570°-77.0580° |
| Total reflections collected | 26894 |
| Index ranges | −17 ≤ h ≤ 17; −10 ≤ k ≤ 11; −25 ≤ l ≤ 27 |
| θ range for data collection | θ$_{min}$ = 3.259°, θ$_{max}$ = 77.621° |
| Completeness to θ$_{max}$ | 98.6% |
| Completeness to θ$_{full}$ = 67.684° | 100% |
| Absorption correction | multi-scan |
| Transmission coefficient range | 0.837-1.000 |
| Refinement method | full matrix least-squares on F$^2$ |
| Independent reflections | 10520 [R$_{int}$ = 0.0330, R$_\sigma$ = 0.0387] |
| Reflections [I > 2σ(I)] | 9411 |
| Reflections/restraints/parameters | 10520/1/723 |
| Goodness-of-fit on F$^2$ | S = 1.05 |
| Final residuals [I > 2σ(I)] | R = 0.0348, R$_w$ = 0.0874 |
| Final residuals [all reflections] | R = 0.0399, R$_w$ = 0.0904 |
| Largest diff. peak and hole (e Å$^{-3}$) | 0.311, −0.280 |
| Max/mean shift/standard uncertainty | 0.001/0.000 |
| Absolute structure determination | Flack parameter: −0.034(10) |

The observed XRPD peaks for SRR G-1 Besylate Form A are listed in Table 18

TABLE 18

| Diffraction angle 2θ (°) | d-spacing (Å) | Intensity (%) |
|---|---|---|
| 4.26 ± 0.20 | 20.737 ± 0.974 | 32 |
| 6.51 ± 0.20 | 13.567 ± 0.416 | 22 |
| 6.71 ± 0.20 | 13.157 ± 0.392 | 100 |
| 8.54 ± 0.20 | 10.340 ± 0.242 | 14 |
| 8.72 ± 0.20 | 10.131 ± 0.232 | 7 |
| 9.18 ± 0.20 | 9.625 ± 0.209 | 10 |
| 10.97 ± 0.20 | 8.059 ± 0.147 | 15 |
| 12.03 ± 0.20 | 7.351 ± 0.122 | 12 |
| 12.14 ± 0.20 | 7.283 ± 0.120 | 6 |
| 12.67 ± 0.20 | 6.980 ± 0.110 | 4 |
| 12.83 ± 0.20 | 6.895 ± 0.107 | 7 |
| 13.06 ± 0.20 | 6.774 ± 0.103 | 4 |
| 13.25 ± 0.20 | 6.678 ± 0.100 | 15 |
| 13.45 ± 0.20 | 6.577 ± 0.097 | 13 |
| 13.67 ± 0.20 | 6.471 ± 0.094 | 13 |
| 14.83 ± 0.20 | 5.970 ± 0.080 | 11 |
| 15.55 ± 0.20 | 5.694 ± 0.073 | 4 |
| 15.95 ± 0.20 | 5.551 ± 0.069 | 13 |
| 16.14 ± 0.20 | 5.488 ± 0.068 | 6 |
| 16.24 ± 0.20 | 5.455 ± 0.067 | 5 |
| 16.36 ± 0.20 | 5.413 ± 0.066 | 7 |
| 16.86 ± 0.20 | 5.254 ± 0.062 | 22 |
| 17.14 ± 0.20 | 5.169 ± 0.060 | 9 |
| 17.51 ± 0.20 | 5.060 ± 0.057 | 9 |
| 17.98 ± 0.20 | 4.930 ± 0.054 | 4 |
| 18.58 ± 0.20 | 4.771 ± 0.051 | 5 |
| 18.92 ± 0.20 | 4.687 ± 0.049 | 20 |
| 19.09 ± 0.20 | 4.645 ± 0.048 | 7 |
| 19.42 ± 0.20 | 4.567 ± 0.047 | 13 |
| 19.99 ± 0.20 | 4.437 ± 0.044 | 58 |
| 20.29 ± 0.20 | 4.373 ± 0.043 | 31 |
| 20.62 ± 0.20 | 4.304 ± 0.041 | 21 |
| 20.75 ± 0.20 | 4.277 ± 0.041 | 74 |
| 21.35 ± 0.20 | 4.158 ± 0.038 | 25 |
| 21.40 ± 0.20 | 4.149 ± 0.038 | 31 |
| 21.46 ± 0.20 | 4.137 ± 0.038 | 39 |
| 21.65 ± 0.20 | 4.102 ± 0.037 | 16 |
| 21.81 ± 0.20 | 4.072 ± 0.037 | 9 |
| 22.06 ± 0.20 | 4.026 ± 0.036 | 60 |
| 22.12 ± 0.20 | 4.015 ± 0.036 | 51 |
| 22.32 ± 0.20 | 3.980 ± 0.035 | 28 |
| 22.45 ± 0.20 | 3.957 ± 0.035 | 15 |
| 22.67 ± 0.20 | 3.919 ± 0.034 | 4 |
| 23.01 ± 0.20 | 3.861 ± 0.033 | 8 |
| 23.14 ± 0.20 | 3.840 ± 0.033 | 7 |
| 23.55 ± 0.20 | 3.775 ± 0.032 | 14 |
| 23.70 ± 0.20 | 3.751 ± 0.031 | 13 |
| 23.78 ± 0.20 | 3.739 ± 0.031 | 14 |
| 23.99 ± 0.20 | 3.706 ± 0.030 | 36 |
| 24.05 ± 0.20 | 3.697 ± 0.030 | 26 |
| 24.18 ± 0.20 | 3.677 ± 0.030 | 15 |
| 24.36 ± 0.20 | 3.651 ± 0.030 | 15 |
| 24.43 ± 0.20 | 3.640 ± 0.029 | 19 |
| 24.79 ± 0.20 | 3.589 ± 0.029 | 3 |
| 25.23 ± 0.20 | 3.528 ± 0.028 | 3 |
| 25.68 ± 0.20 | 3.466 ± 0.027 | 8 |
| 25.84 ± 0.20 | 3.446 ± 0.026 | 12 |
| 25.92 ± 0.20 | 3.435 ± 0.026 | 21 |
| 26.30 ± 0.20 | 3.386 ± 0.025 | 11 |
| 26.69 ± 0.20 | 3.337 ± 0.025 | 7 |
| 26.84 ± 0.20 | 3.319 ± 0.024 | 12 |
| 27.25 ± 0.20 | 3.270 ± 0.024 | 4 |
| 27.49 ± 0.20 | 3.242 ± 0.023 | 6 |
| 27.81 ± 0.20 | 3.205 ± 0.023 | 16 |
| 28.22 ± 0.20 | 3.160 ± 0.022 | 3 |
| 28.40 ± 0.20 | 3.140 ± 0.022 | 3 |
| 28.65 ± 0.20 | 3.114 ± 0.021 | 3 |
| 28.84 ± 0.20 | 3.093 ± 0.021 | 3 |
| 29.09 ± 0.20 | 3.068 ± 0.021 | 9 |
| 29.63 ± 0.20 | 3.012 ± 0.020 | 8 |
| 29.96 ± 0.20 | 2.980 ± 0.019 | 5 |
| 30.25 ± 0.20 | 2.952 ± 0.019 | 6 |

The solution ¹H NMR spectrum is consistent with a 1:1 stoichiometric salt of SRR G-1 and benzenesulfonic acid. Residual solvent is not evident, consistent with an unsolvated form.

Figure 28A:
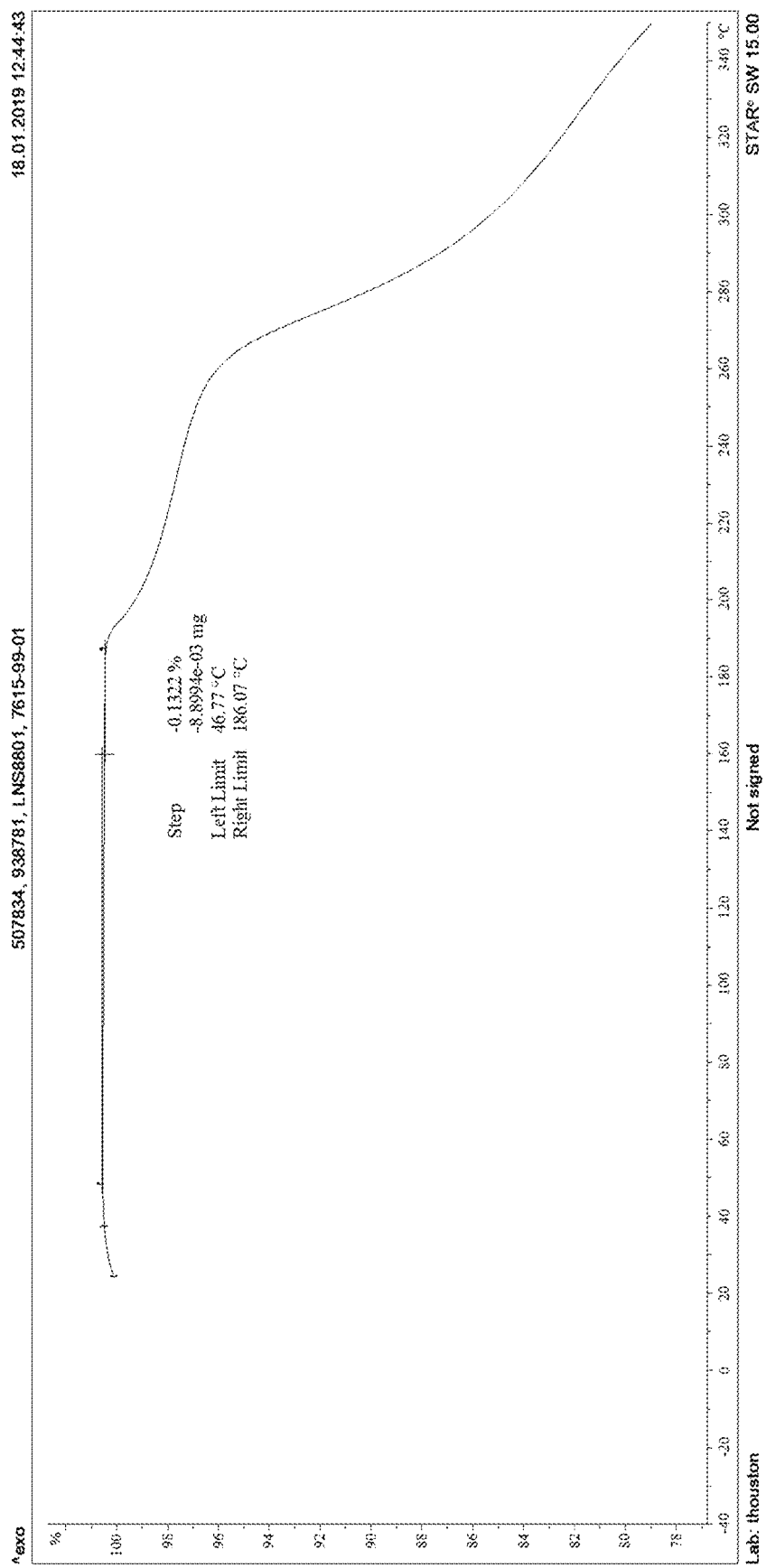
FIGS. 28A and 28B show the Thermograms for SRR G-1 Besylate Form A.
Figure 28B:
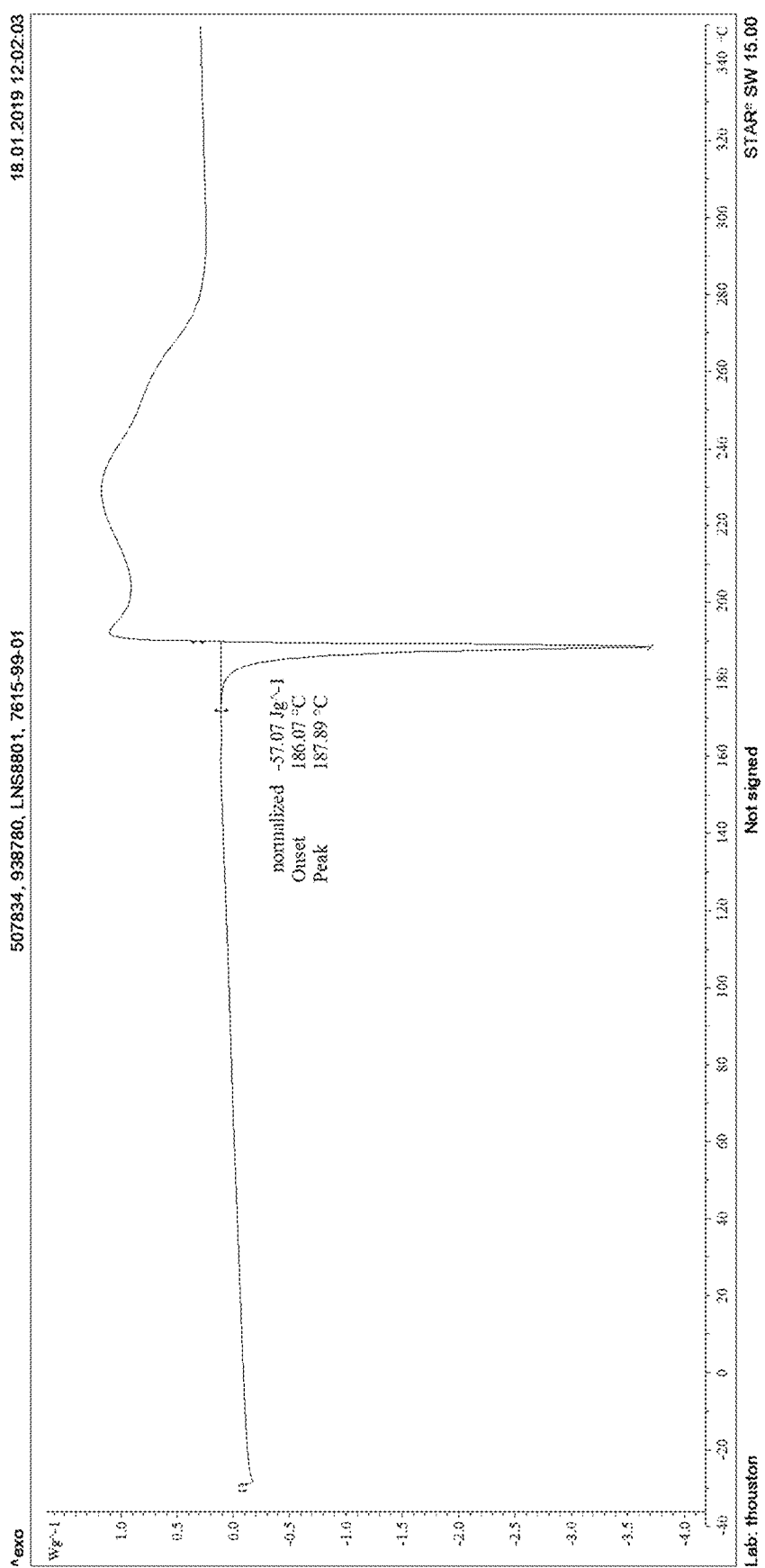

Thermograms of SRR G-1 Besylate Form A are provided in FIGS. 28A and 28B. Negligible weight loss up to 186° C. is evident by TGA, consistent with an anhydrous form. The DSC exhibits a sharp endotherm with an onset near 186° C. The event is likely due to a melt concurrent with decomposition. A small endotherm near 164° C. is also evident. The nature of this endotherm is unknown.

The possibility of disproportionation in water was investigated. SRR G-1 Besylate Form A was slurried in water for 4 days. The excess solids were recovered and reanalyzed by XRPD for evidence of freebase or benzenesulfonic acid. The recovered material was SRR G-1 Besylate Form A, indicating that disproportionation did not occur under the condition evaluated.

The following describes a 1-gram scale procedure for generating SRR G-1 Besylate Form A. A molar equivalent, 0.50 g, of benzenesulfonic acid monohydrate was added to a vessel containing 1.17 g of SRR G-1 freebase Form A. In addition, a small quantity of SRR G-1 Besylate Form A was added as seeds. Ethyl acetate, 7 mL, was added and followed by sonication. A predominant portion of the solids dissolved, resulting in a yellow solution, but was immediately followed by precipitation of white solids. An additional 3 mL of ethyl acetate was added to facilitate slurry transfer and filtration. The solids were recovered by vacuum filtration and rinsed with 4 mL of ethyl acetate followed by vacuum at room temperature overnight. Approximately 0.99 grams of SRR G-1 Besylate Form A was obtained.

SRR G-1 Camsylate Form A

SRR G-1 Camsylate Form A is an anhydrous 1:1 stoichiometric salt with an apparent melt onset of 172° C.

Figure 29:
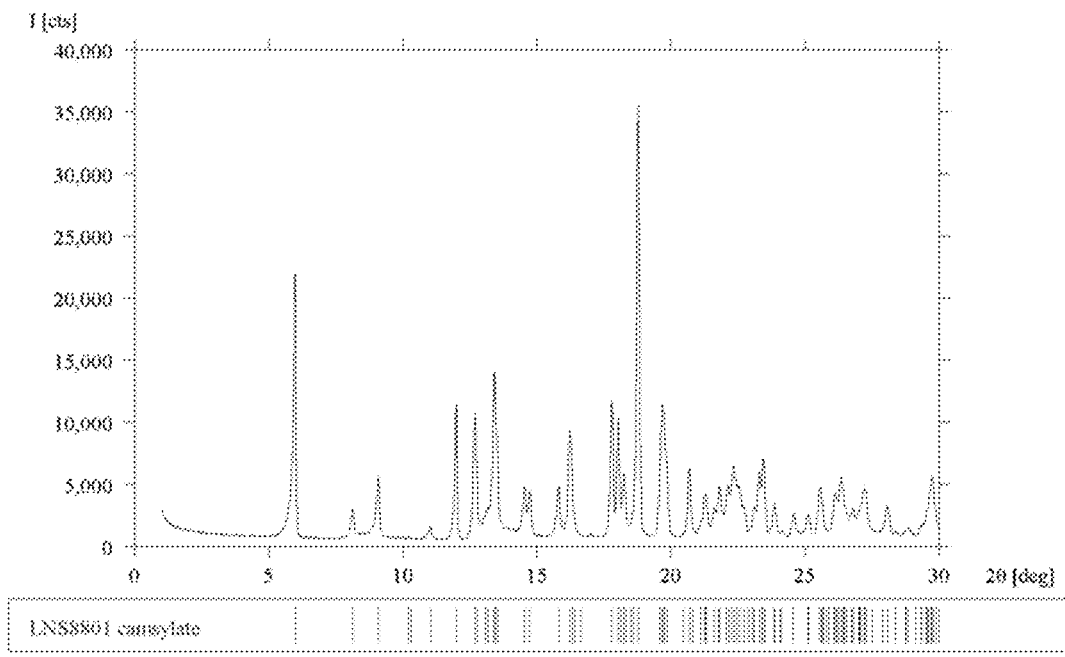
FIG. 29 shows the Indexing results for SRR G-1 Camsylate Form A.
Figure 30:
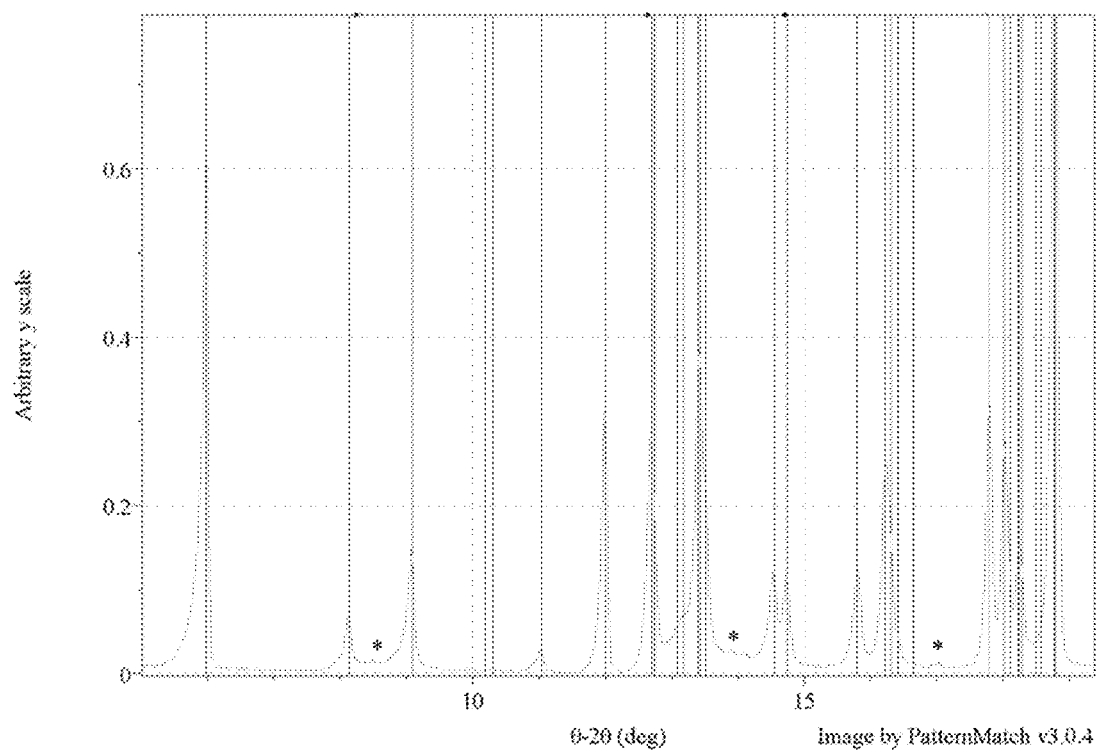
FIG. 30 shows the XRPD pattern for SRR G-1 Camsylate Form A shown from 5 to 19° (2θ).

The XRPD pattern of SRR G-1 Camsylate Form A was successfully indexed, suggesting it is composed primarily of a single crystalline phase (FIG. 29). SRR G-1 Camsylate Form A has a triclinic unit cell that can accommodate two SRR G-1 cations and two camsylate anions. The formula unit volume of 737.9 Å$^3$ calculated from the indexing results would be consistent with an anhydrous form with a calculated density of 1.451 g cm$^{-3}$. The XRPD pattern also contains a small number of minor peaks that are not associated with SRR G-1 Camsylate Form A, the known polymorphs of the freebase, or (+)-(1S)-camphor-10-sulfonic acid. These additional peaks are highlighted in FIG. 30 with asterisks.

The observed XRPD peaks for SRR G-1 Camsylate Form A are listed in Table 19

TABLE 19

| Diffraction angle 2θ (°) | d-spacing (Å) | Intensity (%) |
| --- | --- | --- |
| 5.97 ± 0.20 | 14.786 ± 0.495 | 62 |
| 8.12 ± 0.20 | 10.876 ± 0.267 | 9 |
| 9.07 ± 0.20 | 9.738 ± 0.214 | 16 |
| 11.02 ± 0.20 | 8.025 ± 0.145 | 4 |
| 11.98 ± 0.20 | 7.379 ± 0.123 | 32 |
| 12.69 ± 0.20 | 6.972 ± 0.109 | 30 |
| 13.41 ± 0.20 | 6.596 ± 0.098 | 39 |
| 14.53 ± 0.20 | 6.089 ± 0.083 | 14 |
| 14.73 ± 0.20 | 6.009 ± 0.081 | 13 |
| 15.80 ± 0.20 | 5.604 ± 0.070 | 14 |
| 16.23 ± 0.20 | 5.456 ± 0.067 | 26 |
| 17.79 ± 0.20 | 4.981 ± 0.056 | 33 |
| 18.03 ± 0.20 | 4.916 ± 0.054 | 29 |
| 18.25 ± 0.20 | 4.858 ± 0.053 | 17 |

TABLE 19-continued

| Diffraction angle 2θ (°) | d-spacing (Å) | Intensity (%) |
| --- | --- | --- |
| 18.77 ± 0.20 | 4.724 ± 0.050 | 100 |
| 19.69 ± 0.20 | 4.506 ± 0.045 | 32 |
| 20.68 ± 0.20 | 4.292 ± 0.041 | 18 |
| 21.28 ± 0.20 | 4.172 ± 0.039 | 12 |
| 21.62 ± 0.20 | 4.107 ± 0.038 | 9 |
| 21.81 ± 0.20 | 4.071 ± 0.037 | 14 |
| 22.13 ± 0.20 | 4.014 ± 0.036 | 14 |
| 22.33 ± 0.20 | 3.977 ± 0.035 | 19 |
| 22.54 ± 0.20 | 3.941 ± 0.035 | 14 |
| 22.70 ± 0.20 | 3.914 ± 0.034 | 10 |
| 23.11 ± 0.20 | 3.845 ± 0.033 | 9 |
| 23.30 ± 0.20 | 3.815 ± 0.032 | 17 |
| 23.45 ± 0.20 | 3.790 ± 0.032 | 20 |
| 23.86 ± 0.20 | 3.726 ± 0.031 | 10 |
| 24.12 ± 0.20 | 3.687 ± 0.030 | 3 |
| 24.57 ± 0.20 | 3.620 ± 0.029 | 8 |
| 25.12 ± 0.20 | 3.542 ± 0.028 | 8 |
| 25.56 ± 0.20 | 3.482 ± 0.027 | 13 |
| 26.13 ± 0.20 | 3.408 ± 0.026 | 12 |
| 26.35 ± 0.20 | 3.379 ± 0.025 | 16 |
| 26.78 ± 0.20 | 3.327 ± 0.024 | 8 |
| 27.22 ± 0.20 | 3.273 ± 0.024 | 13 |
| 28.07 ± 0.20 | 3.176 ± 0.022 | 9 |
| 28.84 ± 0.20 | 3.093 ± 0.021 | 5 |
| 29.74 ± 0.20 | 3.002 ± 0.020 | 16 |

The solution ¹H NMR spectrum is consistent with a 1:1 stoichiometric salt of SRR G-1 and (+)-(1S)-camphor-10-sulfonic acid. Residual solvent is not evident, consistent with an unsolvated form.

Figure 31A:
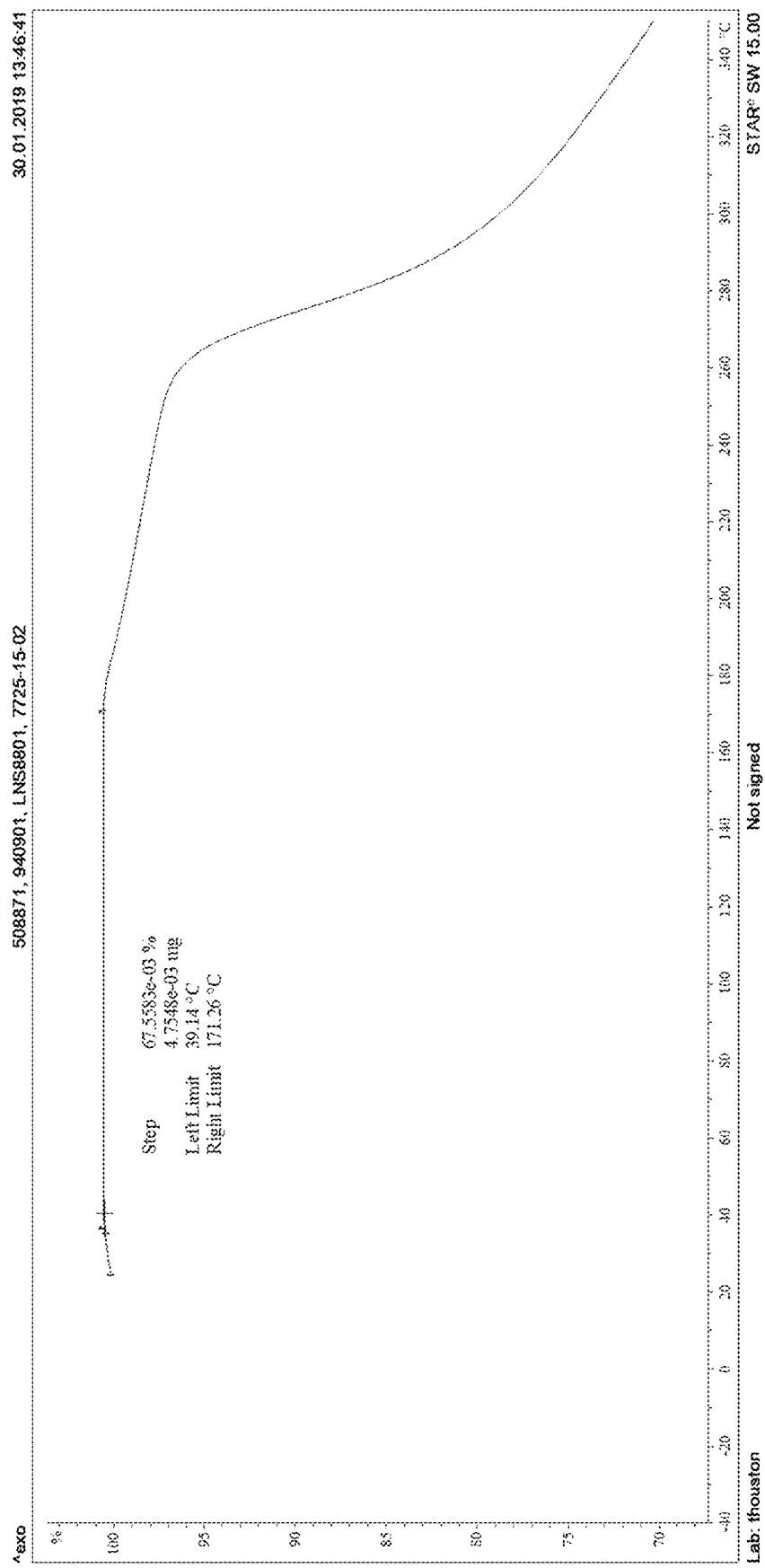
FIGS. 31A and 31B show the Thermograms for SRR G-1 Camsylate Form A.
Figure 31B:
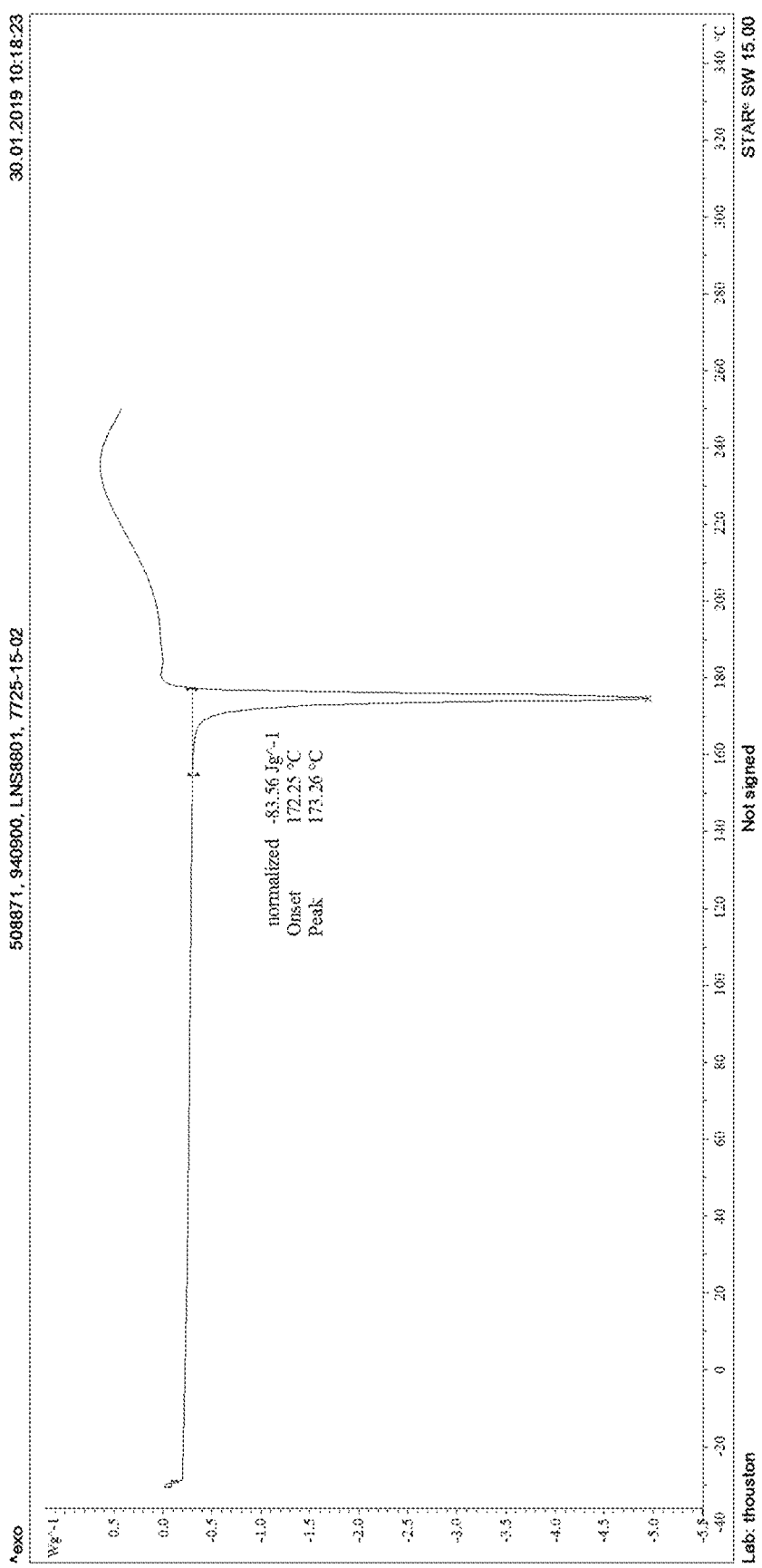

Thermograms for SRR G-1 Camsylate Form A are provided in FIGS. 31A and 31B. Negligible weight loss up to 171° C. is evident by TGA, consistent with an anhydrous form. The DSC exhibits a sharp endotherm with an onset near 172° C. The event is likely due to a melt concurrent with decomposition.

The following describes a 750-mg scale procedure for generating SRR G-1 Camsylate Form A. Less than a molar equivalent (0.9), 0.43 g, of (+)-(1S)-camphor-10-sulfonic acid was added to a vessel containing a suspension composed of 0.86 g of SRR G-1 freebase Form A and 10 mL of ethyl acetate, providing a yellow suspension with a small amount of undissolved solids. Seeds of SRR G-1 Camsylate Form A were added and the suspension was sonicated causing immediate precipitation. The sample was sonicated for an additional ~10 minutes and then left to slurry for approximately 1 hour. The white solids were recovered by vacuum filtration and rinsed with 2 mL of ethyl acetate followed by vacuum at room temperature overnight. Approximately 0.75 grams of SRR G-1 Camsylate Form A was obtained.

SRR G-1 Napsylate Form A

SRR G-1 Napsylate Form A is an anhydrous 1:1 stoichiometric salt with an apparent melt onset of 194° C. Based on XRPD results from an aqueous slurry, disproportionation of the salt does occur in water.

Figure 32:
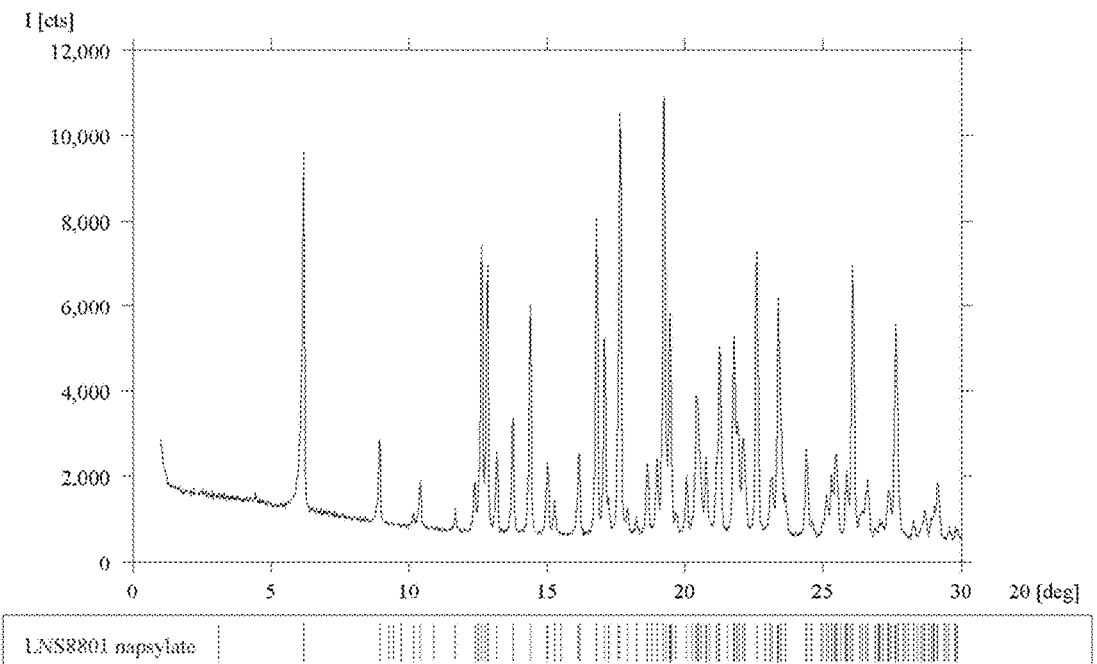
FIG. 32 shows the Indexing results for SRR G-1 Napsylate Form A.

The XRPD pattern of SRR G-1 Napsylate Form A was successfully indexed, suggesting it is composed primarily of a single crystalline phase (FIG. 32). SRR G-1 Napsylate Form A has monoclinic unit cell that can accommodate four SRR G-1 cations and four napsylate anions. The formula unit volume of 707.3 Å$^3$ calculated from the indexing results would be consistent with an anhydrous form with a calculated density of 1.457 g cm$^{-3}$. The XRPD pattern also contains a small, weak peak near 4.4° (2θ) that is not associated with SRR G-1 Napsylate Form A, the known polymorphs of the freebase, or naphthalene-2-sulfonic acid.

The observed XRPD peaks for SRR G-1 Napsylate Form A are listed in Table 20

TABLE 20

| Diffraction angle 2θ (°) | d-spacing (Å) | Intensity (%) |
|---|---|---|
| 6.17 ± 0.20 | 14.321 ± 0.464 | 88 |
| 8.91 ± 0.20 | 9.913 ± 0.222 | 26 |
| 10.16 ± 0.20 | 8.703 ± 0.171 | 10 |
| 10.40 ± 0.20 | 8.496 ± 0.163 | 17 |
| 11.68 ± 0.20 | 7.570 ± 0.129 | 11 |
| 12.38 ± 0.20 | 7.145 ± 0.115 | 17 |
| 12.63 ± 0.20 | 7.001 ± 0.110 | 68 |
| 12.84 ± 0.20 | 6.891 ± 0.107 | 64 |
| 13.18 ± 0.20 | 6.713 ± 0.101 | 23 |
| 13.75 ± 0.20 | 6.433 ± 0.093 | 31 |
| 14.39 ± 0.20 | 6.151 ± 0.085 | 54 |
| 15.01 ± 0.20 | 5.897 ± 0.078 | 21 |
| 15.26 ± 0.20 | 5.800 ± 0.076 | 13 |
| 16.15 ± 0.20 | 5.485 ± 0.067 | 23 |
| 16.79 ± 0.20 | 5.277 ± 0.062 | 73 |
| 17.07 ± 0.20 | 5.189 ± 0.060 | 48 |
| 17.21 ± 0.20 | 5.148 ± 0.059 | 14 |
| 17.64 ± 0.20 | 5.025 ± 0.057 | 95 |
| 17.90 ± 0.20 | 4.950 ± 0.055 | 12 |
| 18.23 ± 0.20 | 4.863 ± 0.053 | 10 |
| 18.62 ± 0.20 | 4.762 ± 0.051 | 21 |
| 18.97 ± 0.20 | 4.674 ± 0.049 | 22 |
| 19.22 ± 0.20 | 4.615 ± 0.048 | 100 |
| 19.44 ± 0.20 | 4.563 ± 0.046 | 53 |
| 19.67 ± 0.20 | 4.510 ± 0.045 | 11 |
| 20.06 ± 0.20 | 4.422 ± 0.044 | 18 |
| 20.43 ± 0.20 | 4.344 ± 0.042 | 35 |
| 20.76 ± 0.20 | 4.274 ± 0.041 | 22 |
| 21.13 ± 0.20 | 4.201 ± 0.039 | 20 |
| 21.26 ± 0.20 | 4.175 ± 0.039 | 46 |
| 21.78 ± 0.20 | 4.077 ± 0.037 | 48 |
| 21.91 ± 0.20 | 4.053 ± 0.037 | 30 |
| 22.11 ± 0.20 | 4.017 ± 0.036 | 26 |
| 22.60 ± 0.20 | 3.931 ± 0.034 | 65 |
| 23.14 ± 0.20 | 3.841 ± 0.033 | 18 |
| 23.38 ± 0.20 | 3.802 ± 0.032 | 56 |
| 23.63 ± 0.20 | 3.762 ± 0.031 | 14 |
| 24.40 ± 0.20 | 3.645 ± 0.029 | 24 |
| 24.60 ± 0.20 | 3.615 ± 0.029 | 9 |
| 25.13 ± 0.20 | 3.541 ± 0.028 | 14 |
| 25.30 ± 0.20 | 3.517 ± 0.027 | 19 |
| 25.47 ± 0.20 | 3.495 ± 0.027 | 23 |
| 25.85 ± 0.20 | 3.444 ± 0.026 | 19 |
| 26.07 ± 0.20 | 3.415 ± 0.026 | 63 |
| 26.60 ± 0.20 | 3.348 ± 0.025 | 18 |
| 26.88 ± 0.20 | 3.315 ± 0.024 | 7 |
| 27.38 ± 0.20 | 3.254 ± 0.023 | 15 |
| 27.63 ± 0.20 | 3.226 ± 0.023 | 50 |
| 28.27 ± 0.20 | 3.154 ± 0.022 | 9 |
| 28.67 ± 0.20 | 3.111 ± 0.021 | 11 |
| 28.90 ± 0.20 | 3.087 ± 0.021 | 9 |
| 29.02 ± 0.20 | 3.075 ± 0.021 | 12 |
| 29.15 ± 0.20 | 3.061 ± 0.021 | 17 |

The solution $^1$H NMR spectrum is consistent with a 1:1 stoichiometric salt of SRR G-1 and naphthalene-2-sulfonic acid. Residual solvent is not evident, consistent with an unsolvated form.

Figure 33A:
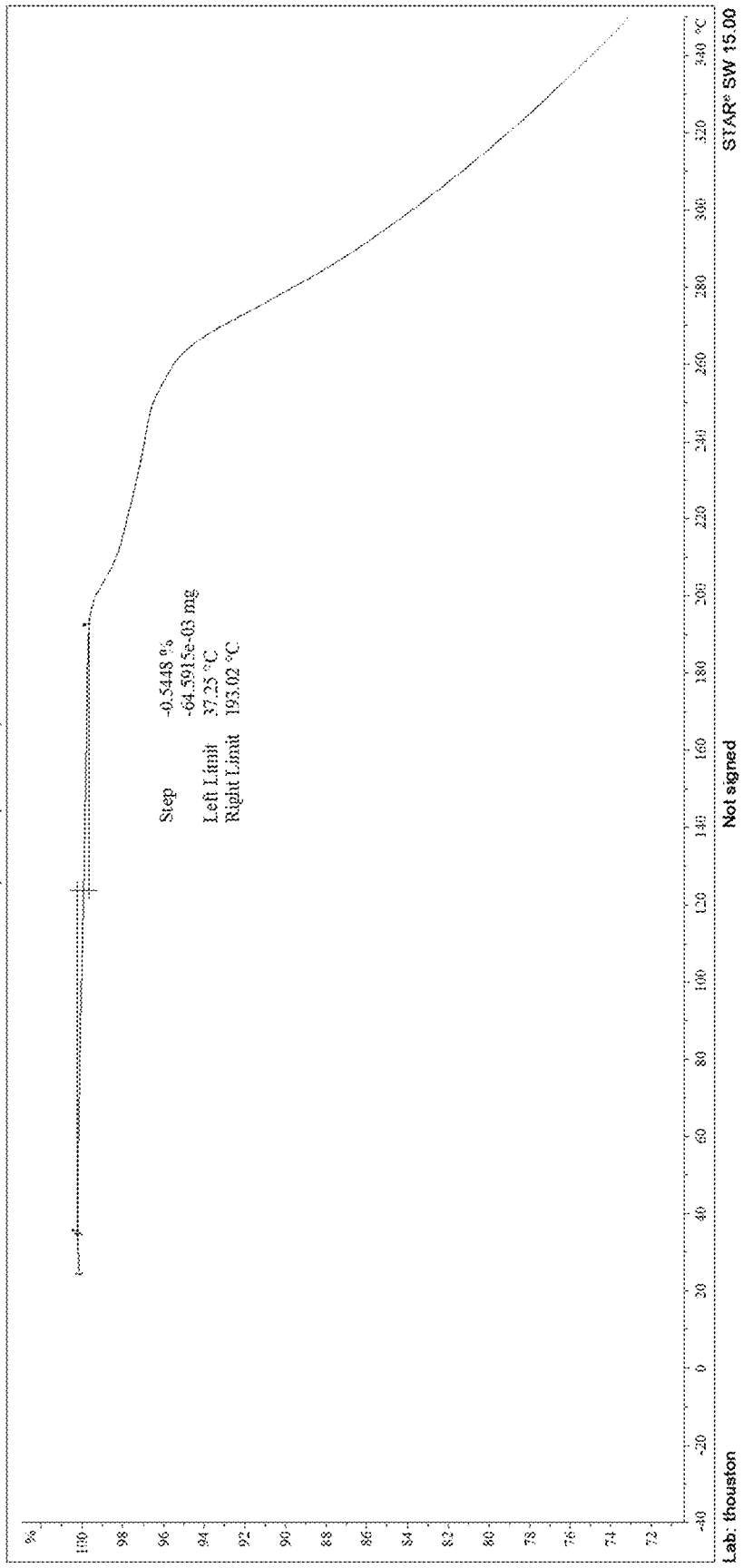
FIGS. 33A and 33B show the Thermograms for SRR G-1 Napsylate Form A.
Figure 33B:
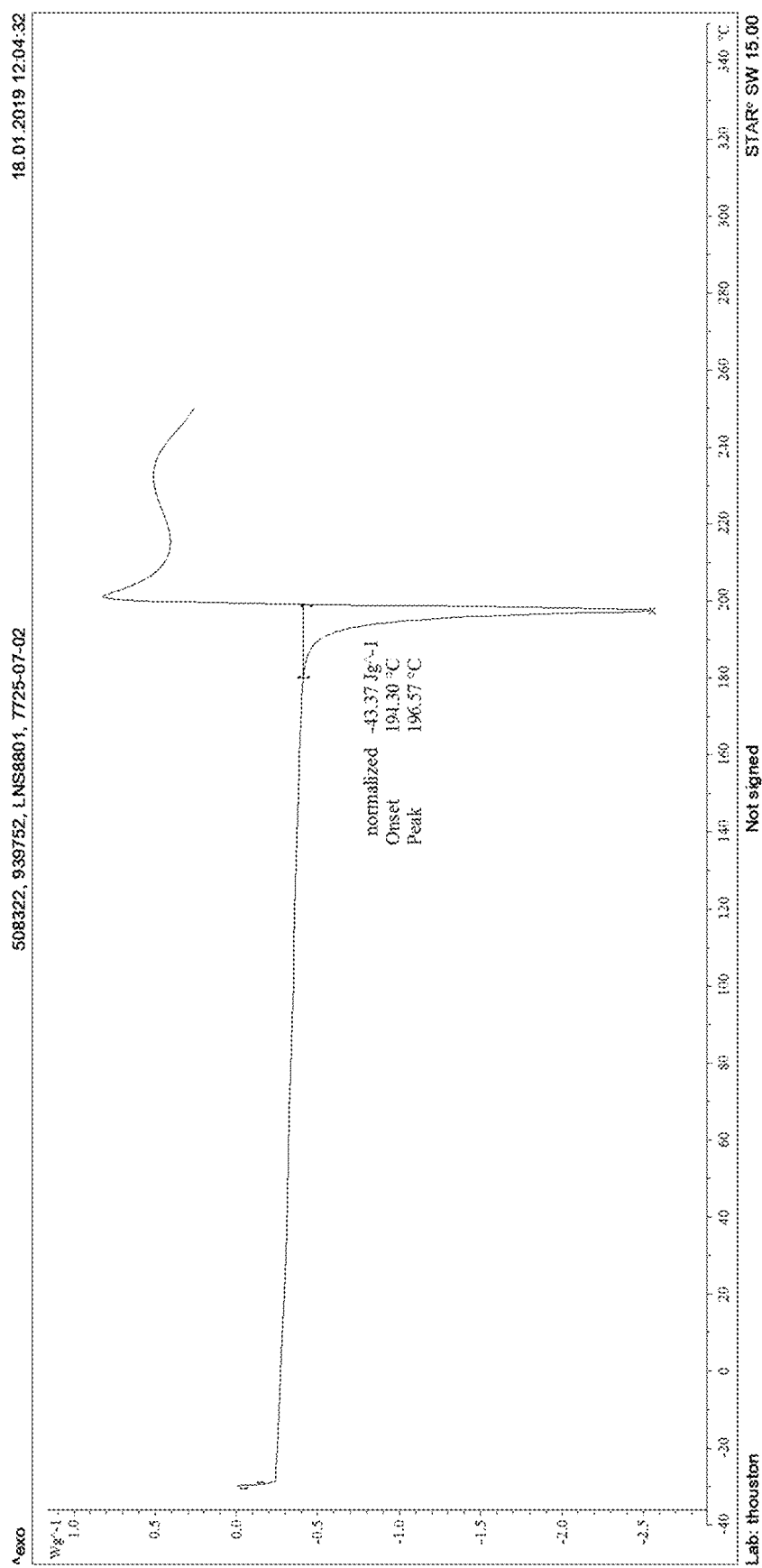

Thermograms for SRR G-1 Napsylate Form A are provided in FIGS. 33A and 33B. Approximately 0.5% weight loss up to 193° C. is evident by TGA. The majority of the loss occurs above ~100° C. Because organic solvent was not observed by NMR, discussed above, it is assumed the loss is due to the volatilization of approximately 0.2 mol/mol water. This suggests that the salt may exhibit limited hygroscopicity. The DSC exhibits a sharp endotherm with an onset near 194° C. The event is likely due to a melt concurrent with decomposition.

The possibility of disproportionation in water was investigated. SRR G-1 Napsylate Form A was slurried in water for 5 days. The excess solids were recovered and reanalyzed by XRPD for evidence of freebase or naphthalene-2-sulfonic acid. The recovered material was freebase Form A, indicating that disproportionation occurred under the condition evaluated.

The following describes a 600-mg scale procedure for generating SRR G-1 Napsylate Form A. Seeds of SRR G-1 Napsylate Form A and a molar equivalent, 0.39 g, of naphthalene-2-sulfonic acid was added to a vessel containing a suspension of 0.73 g of SRR G-1 freebase Form A and 9 mL of ethyl acetate. The yellow suspension with a small amount of undissolved solids was sonicated and a white precipitation occurred. The slurry was sonicated for an additional ~5 minutes and the solids were then recovered by vacuum filtration, rinsed with 2 mL of ethyl acetate, and dried under vacuum at room temperature overnight. Approximately 0.63 grams of SRR G-1 Napsylate Form A was obtained.

Example 5: YUMM1.7 Proliferation Assay

YUMM1.7 cells were cultured for at least 1 passage after thawing and were cultured in DMEM with 5% FBS (Invitrogen) and 1% antibiotic-antimycotic (gibco) at 37C 5% $CO_2$. Proliferation assays were performed by plating 15,000 cells in 12-well plates with 5 replicates per condition tested. Media and drugs were refreshed on Day 2. On Day 4, cells were trypsinized using 0.25 ml 0.05% Trypsin with EDTA (Invitrogen) for 5 minutes to detach from the plate, mixed with 0.75 ml of culture media, and counted using a hemocytometer.

Figure 34:
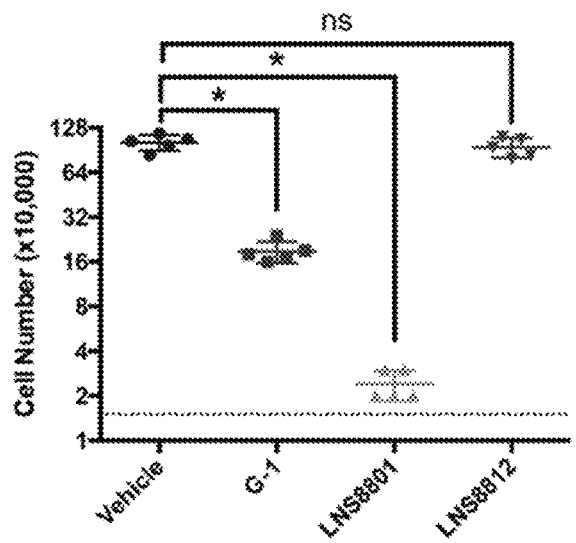
FIG. 34 illustrates the results of a proliferation assay using YUMM1.7 melanoma cells. In this assay, the cells were treated with 500 nM of the racemic mixture (G-1), or the single enantiomers of G-1 SRR G-1, and RSS G-1. The dotted line indicates starting cell population number. n=5 replicates per group. *denotes p<0.05, error bars=±s.d.

The average cell count after 4 days of growth in a YUMM1.7 proliferation assay conducted with 500 nM of each composition are shown in Table 21. The same data is shown in graphical form in FIG. 34. Cell counts are in the tens of thousands (i.e. 100 is about 1,000,000). Starting cell numbers were 15,000. RSS G-1 had approximately the same number of doublings as the vehicle. Racemic G-1 reduced doubling to about half of that seen with the vehicle. Surprisingly, SRR G-1 reduced doubling to less than $\frac{1}{10}^{th}$ of that seen with the vehicle rather than just ¼ as would be expected from the reduction caused by G-1.

TABLE 21

| Vehicle | Racemic G-1 | SRR G-1 | RSS | G-1 |
|---|---|---|---|---|
| | 104 | 16 | 2 | 83 |
| | 84 | 18 | 3 | 94 |
| | 108 | 19 | 2 | 79 |
| | 117 | 17 | 3 | 111 |
| | 97 | 24 | 2 | 107 |
| Averages | 102 | 18.8 | 2.4 | 94.8 |
| Doublings | 8.2 | 3.4 | 0.6 | 7.9 |

Example 6: Preclinical Rat Pharmacokinetic Results

Figure 35:
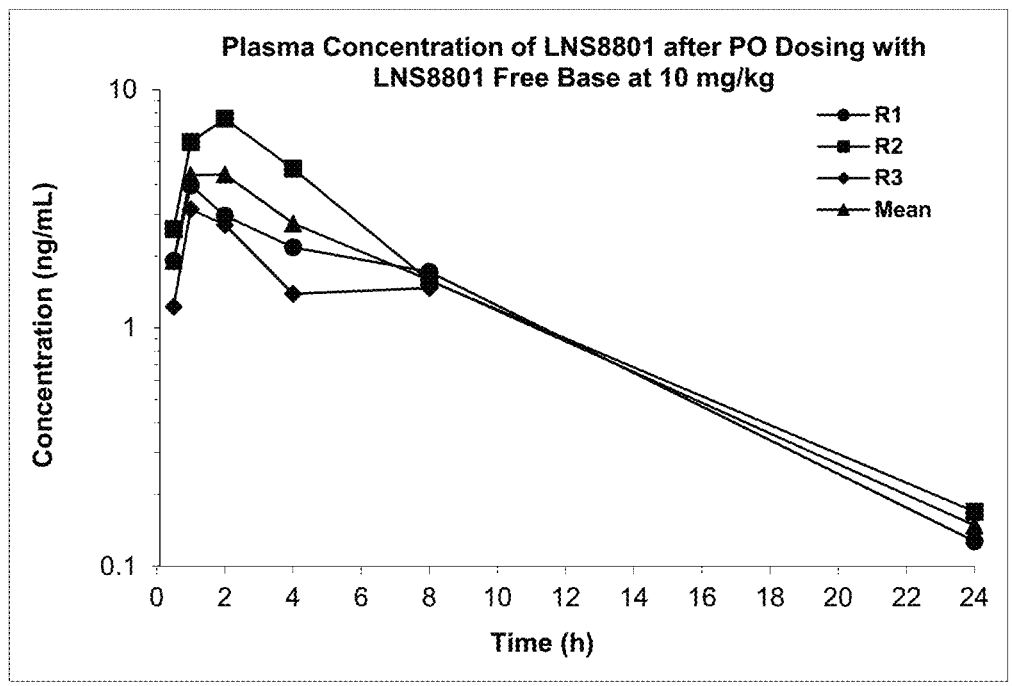
FIG. 35 shows the Plasma Concentration of SRR G-1 in the Rat Dosed with SRR G-1 Free Base.
Figure 36:
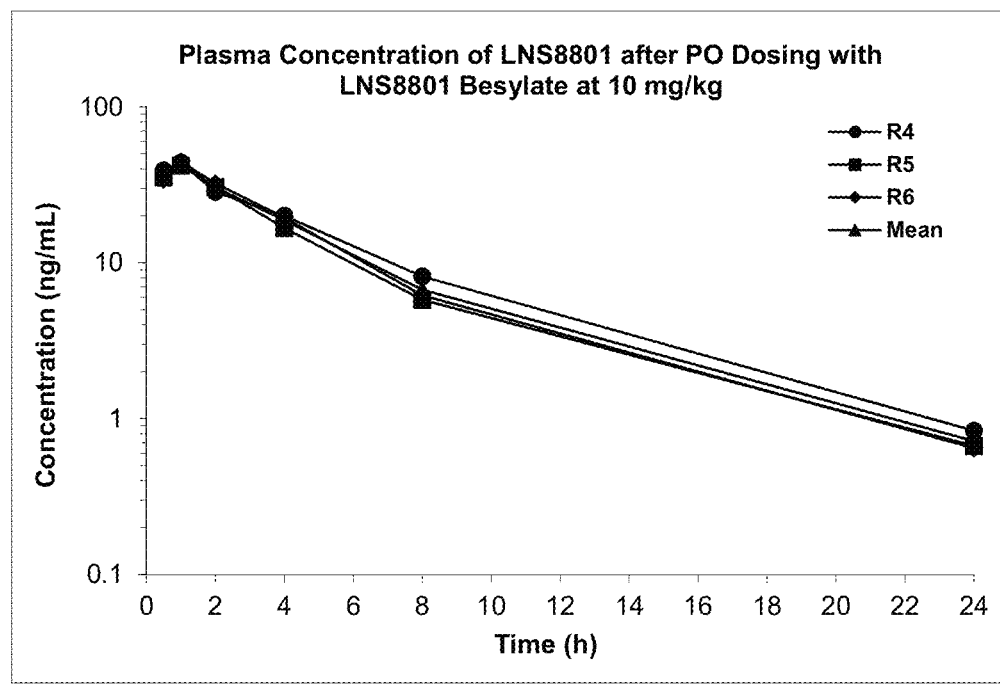
FIG. 36 shows the Plasma Concentration of SRR G-1 in the Rat Dosed with SRR G-1 Besylate.
Figure 37:
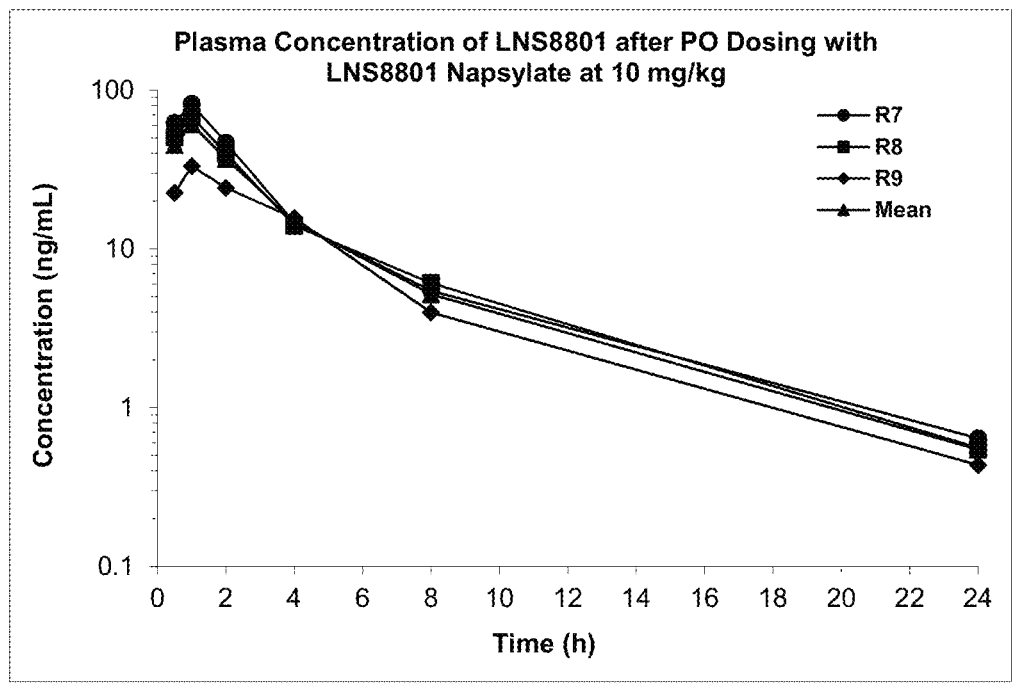
FIG. 37 shows the Plasma Concentration of SRR G-1 in the Rat Dosed with SRR G-1 Napsylate.
Figure 38:
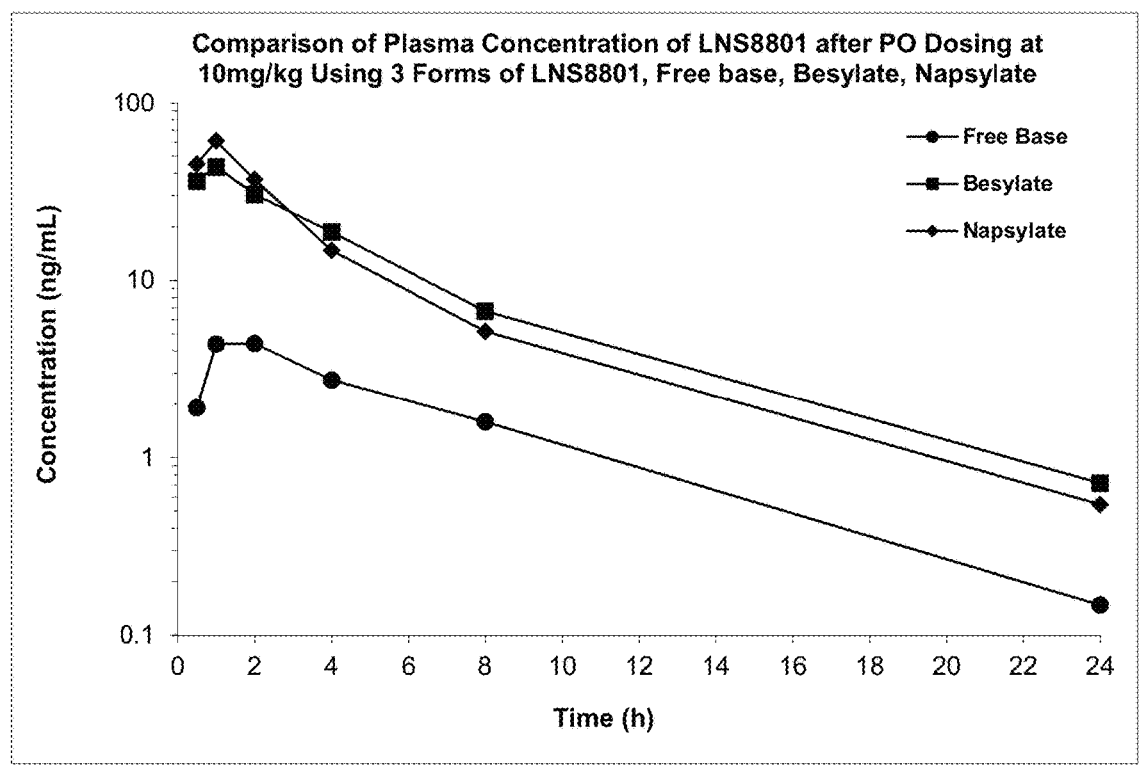
FIG. 38 shows the Comparison of Plasma Concentrations of SRR G-1 in the Rat Dosed with SRR G-1 Free Base, SRR G-1 Besylate, and SRR G-1 Napsylate.

Plasma concentrations of SRR G-1 free base, SRR G-1 besylate, and SRR G-1 napsylate in rats was determined after oral dosing. Three fasted, male rats were treated with 10 mg/kg SRR G-1 free base, SRR G-1 besylate, or SRR G-1 napsylate delivered orally as a suspension in 0.5% hydroxypropyl methylcellulose, 99.5% water. Plasma was isolated at 0.5, 1, 2, 4, 8, and 24 hours after SRR G-1 administration, and plasma concentrations were determined using LC-MS/MS. The results are shown in Tables 22-24 for each respectively. Graphical representation of this data is shown in FIGS. 35-37. FIG. 38 shows a comparison of all three results.

TABLE 22

| SRR G-1 Free Base Plasma PO (10 mg/kg) | LLOQ ULOQ | 0.100 300 Conc. (ng/mL) | ng/mL ng/mL |
|---|---|---|---|
| Time (h) | R1 | R2 | R3 |
| 0.500 | 1.91 | 2.60 | 1.23 |
| 1.00 | 3.96 | 6.03 | 3.15 |
| 2.00 | 2.96 | 7.56 | 2.71 |
| 4.00 | 2.18 | 4.67 | 1.39 |
| 8.00 | 1.72 | 1.58 | 1.47 |
| 24.0 | 0.127 | 0.169 | BQL |

TABLE 23

| SRR G-1 Besylate Plasma PO (10 mg/kg) | LLOQ ULOQ | 0.100 300 Conc. (ng/mL) | ng/mL ng/mL |
|---|---|---|---|
| Time (h) | R4 | R5 | R6 |
| 0.500 | 39.2 | 35.2 | 34.1 |
| 1.00 | 43.9 | 42.0 | 44.5 |
| 2.00 | 28.5 | 30.6 | 32.3 |
| 4.00 | 20.0 | 16.7 | 19.5 |
| 8.00 | 8.17 | 5.78 | 6.18 |
| 24.0 | 0.837 | 0.668 | 0.647 |

TABLE 24

| SRR G-1 Napsylate Plasma PO (10 mg/kg) | LLOQ ULOQ | 0.100 300 Conc. (ng/mL) | ng/mL ng/mL |
|---|---|---|---|
| Time (h) | R7 | R8 | R9 |
| 0.500 | 62.2 | 50.6 | 22.6 |
| 1.00 | 81.9 | 67.5 | 33.2 |
| 2.00 | 46.6 | 39.9 | 24.3 |
| 4.00 | 14.6 | 14.0 | 15.6 |
| 8.00 | 5.45 | 6.09 | 3.97 |
| 24.0 | 0.641 | 0.558 | 0.435 |

Example 7: ADME Toxicology of SRR G-1 and RSS G-1

ADME-Tox: In Vitro Absorption

Drug transporter (fluorometric inhibition)

The percent of control was calculated using the following equation. The percent of inhibition was calculated by subtracting the percent of control from 100. The IC50 value (concentration causing a half-maximal inhibition of the control value) was determined by non-linear regression analysis of the concentration-response curve using the Hill equation.

$$\text{Control}(\%) = \frac{\text{Compound} - \text{Background}}{T1 - \text{Background}} * 100$$

Compound is the individual reading in the presence of the test compound. T1 is the mean reading in the absence of the test compound. Background (for P-gp and BCRP) is the mean reading in the presence of the highest effective concentration of the reference inhibitor. Background (for OATP1B1, OATP1B3, OAT1, OAT3, and OCT2) is the mean reading in the absence of both the test compound and the substrate.

ADME-Tox: In Vitro Metabolism

Cytochrome P450 Inhibition (HPLC-UV/VIS and HPLC-MS/MS detection)

Peak areas corresponding to the metabolite of each substrate were recorded. The percent of control activity was then calculated by comparing the peak area obtained in the presence of the test compound to that obtained in the absence of the test compound. Subsequently, the percent inhibition was calculated by subtracting the percent control activity from 100 for each compound. IC50 values (concentration causing a half-maximal inhibition of control values) were determined by non-linear regression analysis of the concentration-response curve using Hill equation curve fitting.

Transporter inhibition results—When assayed with 10 μM of SRR G-1 or RSS G-1, the following transporters were inhibited more than 50%. For SRR G-1: OATP1B1 82.5%. For RSS G-1: OCT2—53.2%, OATP1B1—91.2%, and OATP1B3—74.3%.

Cytochrome P450 inhibition results—When assayed with 10 μM of SRR G-1 or RSS G-1, the following were inhibited more than 50%. For SRR G-1: CYP2D6—74.3% and CYP2C8—66.7%. For RSS G-1: CYP2C9-50.4%.

Cytochrome P450 induction results—Hepatocytes from three different human cell lines were incubated with SRR G-1 or RSS G-1 at 1 μM, 10 μM, and 100 μM. For SRR G-1: CYP1A2 was induced at both 1 μM and 10 μM in only 1 of the 3 cell lines and CYP3A4 was induced at only 10 μM in 2 of the 3 cell lines. For RSS G-1: CYP1A2 was induced at both 10 μM and 100 μM in 2 of the 3 cell lines.

Example 8: Off Target Selectivity Assays

GPCR cAMP Modulation

Cell Handling—cAMP Hunter cell lines were expanded from freezer stocks according to standard procedures. Cells were seeded in a total volume of 20 μm into white walled, 384-well microplates and incubated at 37° C. for the appropriate time prior to testing. cAMP modulation was determined using the DiscoverX HitHunter cAMP XS+ assay.

Gs Agonist Format—For agonist determination, cells were incubated with sample to induce response. Media was aspirated from cells and replaced with 15 μL 2:1 HBSS/10 mM Hepes:cAMP XS+ Ab reagent. Intermediate dilution of sample stocks was performed to generate 4× sample in assay buffer. 4.5 μL of 4× sample was added to cells and incubated at 37° C. or room temperature for 30 or 60 minutes. Final assay vehicle concentration was 1%.

Gi Agonist Format—For agonist determination, cells were incubated with sample in the presence of $EC_{80}$ forskolin to induce response. Media was aspirated from cells and replaced with 15 μL 2:1 HBSS/10 mM Hepes:cAMP XS+ Ab reagent. Intermediate dilution of sample stocks was performed to generate 4× sample in assay buffer containing 4×$EC_{80}$ forskolin. 4.5 μL of 4× sample was added to cells and incubated at 37° C. or room temperature for 30 or 60 minutes. Final assay vehicle concentration was 1%.

Antagonist Format—For antagonist determination, cells were pre-incubated with sample followed by agonist challenge at the $EC_{80}$ concentration. Media was aspirated from cells and replaced with 10 μL 1:1 HBSS/Hepes:cAMP XS+Ab reagent. 5 μL of 4× compound was added to the cells and incubated at 37° C. or room temperature for 30 minutes.

4.5 µL of 4×$EC_{80}$ agonist was added to cells and incubated at 37° C. or room temperature for 30 or 60 minutes. For Gi coupled GPCRs, $EC_{80}$ forskolin was included.

Signal Detection—After appropriate compound incubation, assay signal was generated through incubation with 20 µL cAMP XS+ED/CL lysis cocktail for one hour followed by incubation with 20 µL cAMP XS+EA reagent for three hours at room temperature. Microplates were read following signal generation with a PerkinElmer Envision™ instrument for chemiluminescent signal detection.

Data Analysis—Compound activity was analyzed using CBIS data analysis suite (ChemInnovation, CA). For Gs agonist mode assays, percentage activity was calculated using the following formula: % Activity=100%×(mean RLU of test sample−mean RLU of vehicle control)/(mean RLU of MAX control−mean RLU of vehicle control). For Gs antagonist mode assays, percentage inhibition was calculated using the following formula: % Inhibition=100%×(1−(mean RLU of test sample−mean RLU of vehicle control)/(mean RLU of $EC_{80}$ control−mean RLU of vehicle control)). For Gi agonist mode assays, percentage activity was calculated using the following formula: % Activity=100%×(1−(mean RLU of test sample−mean RLU of MAX control)/(mean RLU of vehicle control−mean RLU of MAX control)). For Gi antagonist or negative allosteric mode assays, percentage inhibition was calculated using the following formula: % Inhibition=100%×(mean RLU of test sample−mean RLU of $EC_{80}$ control)/(mean RLU of forskolin positive control−mean RLU of $EC_{80}$ control). For Primary screens, percent response was capped at 0% or 100% where calculated percent response returned a negative value or a value greater than 100, respectively.

Calcium Mobilization

Cell Handling—Cell lines were expanded from freezer stocks according to standard procedures. Cells (10,000 cells/well) were seeded in a total volume of 50 µL (200 cells/_L) into black-walled, clear-bottom, Poly-D-lysine coated 384-well microplates and incubated at 37° C. for the appropriate time prior to testing. DMSO concentration for all readouts is ≤0.2%.

Dye Loading—Assays were performed in 1× Dye Loading Buffer consisting of 1× Dye (DiscoverX, Calcium No WashPLUS kit, Catalog No. 90-0091), 1× Additive A and 2.5 mM Probenecid in HBSS/20 mM Hepes. Probenicid was prepared fresh. Cells were loaded with dye prior to testing. Media was aspirated from cells and replaced with 25 µL Dye Loading Buffer. Cells were incubated for 45 minutes at 37° C. and then 20 minutes at room temperature.

Agonist Format—For agonist determination, cells were incubated with sample to induce response. After dye loading, cells were removed from the incubator and 25 µL of 2× compound in HBSS/20 mM Hepes was added using a FLIPR Tetra (MDS). Compound was added and agonist activity was measured on a FLIPR Tetra. Calcium mobilization was monitored for 2 minutes with a 5 second baseline read.

Antagonist Format—Cells were preincubated with sample, dye loaded, moved to the FLIPR Tetra (MDS) and then challenged with an agonist at the EC80 concentration. Calcium mobilization was monitored for 2 minutes with a 5 second baseline read.

Data Analysis—FLIPR read—Area under the curve was calculated for the entire two minute read. Compound activity was analyzed using CBIS data analysis suite (ChemInnovation, CA). For agonist mode assays, percentage activity was calculated using the following formula: % Activity=100%×(mean RFU of test sample−mean RFU of vehicle control)/(mean MAX RFU control ligand−mean RFU of vehicle control). For antagonist mode assays, percentage inhibition was calculated using the following formula: % Inhibition=100%×(1−(mean RFU of test sample−mean RFU of vehicle control)/(mean RFU of $EC_{80}$ control−mean RFU of vehicle control)). For Primary screens, percent response was capped at 0% or 100% where calculated percent response returned a negative value or a value greater than 100, respectively.

Nuclear Hormone Receptor

Cell Handling—PathHunter NHR cell lines were expanded from freezer stocks according to standard procedures. Cells were seeded in a total volume of 20 µL into white walled, 384-well microplates and incubated at 37° C. for the appropriate time prior to testing. Assay media contained charcoal-dextran filtered serum to reduce the level of hormones present.

Agonist Format—For agonist determination, cells were incubated with sample to induce response. Intermediate dilution of sample stocks was performed to generate 5× sample in assay buffer. 3.5 µL of 5× sample was added to cells and incubated at 37° C. or room temperature for 3-16 hours. Final assay vehicle concentration was 1%.

Antagonist Format—For antagonist determination, cells were pre-incubated with antagonist followed by agonist challenge at the $EC_{80}$ concentration. Intermediate dilution of sample stocks was performed to generate 5× sample in assay buffer. 3.5 µL of 5× sample was added to cells and incubated at 37° C. or room temperature for 60 minutes. Vehicle concentration was 1%. 4.5 µL of 6×$EC_{80}$ agonist in assay buffer was added to the cells and incubated at 37° C. or room temperature for 3-16 hours.

Signal Detection—Assay signal was generated through a single addition of 12.5 or 15 µL (50% v/v) of PathHunter Detection reagent cocktail, followed by a one hour incubation at room temperature. Microplates were read following signal generation with a PerkinElmer Envision™ instrument for chemiluminescent signal detection.

Data Analysis—Compound activity was analyzed using CBIS data analysis suite (ChemInnovation, CA). For agonist mode assays, percentage activity was calculated using the following formula: % Activity=100%×(mean RLU of test sample−mean RLU of vehicle control)/(mean MAX control ligand−mean RLU of vehicle control). For antagonist mode assays, percentage inhibition was calculated using the following formula: % Inhibition=100%×(1−(mean RLU of test sample−mean RLU of vehicle control)/(mean RLU of $EC_{80}$ control−mean RLU of vehicle control)). Note that for select assays, the ligand response produces a decrease in receptor activity (inverse agonist with a constitutively active target). For those assays inverse agonist activity was calculated using the following formula: % Inverse Agonist Activity=100%×((mean RLU of vehicle control−mean RLU of test sample)/(mean RLU of vehicle control−mean RLU of MAX control)). For Primary screens, percent response was capped at 0% or 100% where calculated percent response returned a negative value or a value greater than 100, respectively.

KINOMEscan Binding Assays

Protein Expression—For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 µm) to remove cell debris. The remaining kinases were produced in HEK-293 cells and subsequently tagged with DNA for qPCR detection.

Capture Ligand Production—Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding.

Binding Reaction Assembly—Binding reactions were assembled by combining kinases, liganded affinity beads, and test compounds in 1× binding buffer (20% SeaBlock, 0.17×PBS, 0.05% Tween 20, 6 mM DTT). All reactions were performed in polypropylene 384-well plates in a final volume of 0.02 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Signal Detection—The kinase concentration in the eluates was measured by qPCR. qPCR reactions were assembled by adding 2.5 μL of kinase eluate to 7.5 μL of qPCR master mix containing 0.15 μM amplicon primers and 0.15 μM amplicon probe. The qPCR protocol consisted of a 10 minute hot start at 95° C., followed by 35 cycles of 95° C. for 15 seconds, 60° C. for 1 minute.

Data Analysis—Percent Response Calculation $$\left(\frac{\text{test compound signal} - \text{positive control signal}}{\text{negative compound signal} - \text{positive control signal}}\right) \times 100$$

Test compound=SRR G-1
Negative control=DMSO (100% Ctrl)
Positive control=control compound (0% Ctrl)
Percent of Control was converted to Percent Response using formula: Percent Response=(100−Percent Control). For Primary screens, percent response was capped at 0% or 100% where calculated percent response returned a negative value or a value greater than 100, respectively.

Data Analysis—Binding Constants (Kds)
Binding constants (Kds) were calculated with a standard doseresponse curve using the Hill equation:

$$\text{Response} = \text{Background} + \left(\frac{\text{Signal} - \text{Background}}{1 + (Kd^{Hill\ Slope} / Dose^{Hill\ Slope})}\right)$$

The Hill Slope was set to −1.
Curves were fitted using a non-linear least square fit with the Levenberg-Marquardt algorithm.

Ion Channel Assays
Cell Handling—Cell lines were expanded from freezer stocks according to standard procedures. Cells were seeded in a total volume of 20 μL into black-walled, clear-bottom, Poly-D-lysine coated 384-well microplates and incubated at 37° C. for the appropriate time prior to testing.

Dye Loading—Assays were performed in 1× Dye Loading Buffer consisting of 1× Dye, and 2.5 mM Probenicid when applicable. Probenicid was prepared fresh. Cells were loaded with dye prior to testing. Cells were incubated for 30-60 minutes at 37° C.

Agonist/Opener Format—For agonist determination, cells were incubated with sample to induce response. Intermediate dilution of sample stocks was performed to generate 2-5× sample in assay buffer. 10-25 μL of 2-5× sample was added to cells and incubated at 37° C. or room temperature for 30 minutes. Final assay vehicle concentration was 1%.

Antagonist/Blocker Format—For antagonist determination, cells were pre-incubated with sample. Intermediate dilution of sample stocks was performed to generate 2-5× sample in assay buffer. After dye loading, cells were removed from the incubator and 10-25 μL 2-5× sample was added to cells in the presence of $EC_{80}$ agonist when appropriate. Cells were incubated for 30 minutes at room temperature in the dark to equilibrate plate temperature. Vehicle concentration was 1%.

Signal Detection—Compound activity was measured on a FLIPR Tetra (MDS).

Data Analysis—Compound activity was analyzed using CBIS data analysis suite (ChemInnovation, CA). For agonist mode assays, percentage activity was calculated using the following formula: % Activity=100%×(mean RLU of test sample−mean RLU of vehicle control)/(mean MAX control ligand−mean RLU of vehicle control). For antagonist percentage inhibition was calculated using the following formula: % Inhibition=100%×(1−(mean RLU of test sample−mean RLU of vehicle control)/(mean RLU of $EC_{80}$ control−mean RLU of vehicle control)). For Primary screens, percent response was capped at 0% or 100% where calculated percent response returned a negative value or a value greater than 100, respectively.

Transporter Assays
Cell Handling—Cell lines were expanded from freezer stocks according to standard procedures. Cells were seeded in a total volume of 25 μL into black-walled, clear-bottom, Poly-D-lysine coated 384-well microplates and incubated at 37° C. for the appropriate time prior to testing.

Blocker/Antagonist Format—After cell plating and incubation, media was removed and 25 μL of 1× compound in 1×HBSS/0.1% BAS was added. Compounds were incubated with cells at 37° C. for 30 minutes.

Dye Loading—Assays were performed in 1× Dye Loading Buffer consisting of 1× Dye, 1×HBSS/20 mM Hepes. After compound incubation, 25 μL of 1× dye was added to wells. Cells were incubated for 30-60 minutes at 37° C.

Signal Detection—After dye incubation, microplates were transferred to a PerkinElmer Envision™ instrument for fluorescence signal detection.

Data Analysis—Compound activity was analyzed using CBIS data analysis suite (ChemInnovation, CA). For blocker mode assays, percentage inhibition was calculated using the following formula: % Inhibition=100%×(1−(mean RLU of test sample−mean RLU of vehicle control)/(mean RLU of positive control−mean RLU of vehicle control)). For Primary screens, percent response was capped at 0% or 100% where calculated percent response returned a negative value or a value greater than 100, respectively.

Enzymatic Assays
Enzyme Preparations—Enzyme preparations were sourced from various vendors-AChE (R&D Systems), COX1 and COX2 (BPS Bioscience), MAOA (Sigma), PDE3A and PDE4D2 (Signal Chem).

Enzyme Activity Assays—Enzymatic assays determine the enzymatic activity by measuring either the consumption of substrate or production of product over time. Different detection methods were used in each enzymatic assay to measure the concentrations of substrates and products. AChE: Enzyme and test compound were preincubated for 15 minutes at room temp before substrate addition. Acetylthiocholine and DTNB were added and incubated at room temperature for 30 minutes. Signal was detected by measuring absorbance at 405 nm. COX1 & COX2: Enzyme stocks were diluted in Assay Buffer (40 mM Tris-HCl, 1×PBS, 0.5 mM Phenol, 0.01% Tween-20+100 nM Hematin) and allowed to equilibrate with compounds at room temperature for 30 minutes (binding incubation). Arachidonic acid (1.7 µM) and Ampliflu Red (2.5 µM) were prepared and dispensed into a reaction plate. Plates were read immediately on a fluorimeter with the emission detection at 590 nm and excitation wavelength 544 nm. MAOA: Enzyme and test compound were preincubated for 15 minutes at 37° C. before substrate addition. The reaction was initiated by addition of kynuramine and incubated at 37° C. for 30 minutes. The reaction was terminated by addition of NaOH. The amount of 4-hydroquioline formed was determined through spectrofluorimetric readout with the emission detection at 380 nm and excitation wavelength 310 nm. PDE3A & PDE4D2: Enzyme and test compound were preincubated for 15 minutes at room temp before substrate addition. cAMP substrate (at a concentration equal to $EC_{80}$) was added and incubated at room temperature for 30 minutes. Enzyme reaction was terminated by addition of 9 mM IBMX. Signal was detected using the HitHunter® cAMP detection kit.

Signal Detection—For each assay, microplates were transferred to a PerkinElmer Envision™ instrument and readout as described.

Data Analysis—Compound activity was analyzed using CBIS data analysis suite (ChemInnovation, CA). For enzyme activity assays, percentage inhibition was calculated using the following formula: % Inhibition=100%×(1−(mean RLU of test sample−mean RLU of vehicle control)/(mean RLU of positive control−mean RLU of vehicle control)). For Primary screens, percent response was capped at 0% or 100% where calculated percent response returned a negative value or a value greater than 100, respectively.

Results of the Off Target Selectivity Assays

Both SRR G-1 and RSS G-1 were tested for selectivity against potential off targets in 78 assays in a dose response format at concentrations up to 10 µM. SRR G-1 only had a measurable $IC_{50}$ or $EC_{50}$ on Cannabinoid receptor 1 at 2.5 µM, HTR2B at 8.2 µM, OPRD1 at 0.87 µM, and OPRM1 at 6.68 µM. RSS G-1 only had a measurable $IC_{50}$ or $EC_{50}$ on Cannabinoid receptor 1 at 3.1 µM, ADRA2A at 2.07 µM, HTR1A at 2.1 µM, and AR at 4.76 µM.

What is claimed is:

1. A compound, of the formula:

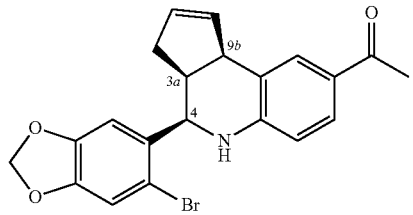

1-((3aS,4R,9bR)-4-(6-bromobenzo[d][1,3]dioxol-5-yl)-3a,4,5,9b-tetrahydro-3H-cyclopenta[c]quinolin-8-yl)ethan-1-one

SSR-G-1 or a pharmaceutically acceptable salt thereof,
wherein the compound comprises a crystalline Form A characterized by an XRPD pattern having peaks expressed in degrees 2θ (±0.20) at about 5.75, about 20.54, about 20.71, about 21.25, and about 21.86,
wherein the crystalline Form A has a melt onset of about 176° C.,
wherein the crystalline Form A is anhydrous,
wherein the crystalline Form A exhibits low hygroscopicity, and
wherein the crystalline Form A exhibits a calculated density of about 1.485 g $cm^{-3}$.

2. The compound of claim 1, wherein the crystalline Form A has a melt onset of about 176° C.

3. The compound of claim 1, wherein the crystalline Form A is anhydrous.

4. The compound of claim 1, wherein the crystalline Form A exhibits low hygroscopicity.

5. The compound of claim 1, wherein the crystalline Form A exhibits a calculated density of about 1.485 g $cm^{-3}$.

6. The compound of claim 1, wherein the crystalline Form A exhibits a solubility of less than about 2 mg/mL in water.

7. The compound of claim 1, wherein the crystalline Form A is further characterized by an XRPD pattern having peaks expressed in degrees 2θ (±0.20) at about 5.75, about 9.56, about 10.53, about 17.03, about 20.54, about 20.71, about 21.25, about 21.86, about 24.67, and about 28.06.

8. The compound of claim 1, wherein the crystalline Form A is further characterized by an XRPD pattern having peaks expressed in degrees 2θ (±0.20) at about 5.75, about 9.56, about 10.53, about 10.81, about 13.02, about 14.66, about 14.79, about 16.23, about 17.03, about 20.54, about 20.71, about 21.25, about 21.86, about 24.67, and about 28.06.

9. The compound of claim 1, wherein the compound is a pharmaceutically acceptable salt.

10. The compound of claim 9, wherein the pharmaceutically acceptable salt is formed with an acid selected from the group consisting of benzenesulfonic acid, (+)-(1S)-camphor-10-sulfonic acid, and naphthalene-2-sulfonic acid.

11. The compound of claim 1, wherein the compound is a free base.

* * * * *